(12) United States Patent
Giffin et al.

(10) Patent No.: US 12,012,462 B2
(45) Date of Patent: Jun. 18, 2024

(54) CHIMERIC RECEPTORS TO DLL3 AND METHODS OF USE THEREOF

(71) Applicants: AMGEN INC., Thousand Oaks, CA (US); KiTe Pharma, Inc., Santa Monica, CA (US)

(72) Inventors: Michael John Giffin, Newbury Park, CA (US); Melissa Thomas, Palo Alto, CA (US); Christopher Murawsky, Roberts Creek (CA); Ryan B. Case, Alameda, CA (US); Lawren Wu, Foster City, CA (US); Jed J. Wiltzius, Winchester, MA (US); Ruben Alvarez Rodriguez, Los Angeles, CA (US); Jun Feng, Los Angeles, CA (US)

(73) Assignee: Amgen Inc., Thousand Oaks, CA (US)

( * ) Notice: Subject to any disclaimer, the term of this patent is extended or adjusted under 35 U.S.C. 154(b) by 670 days.

(21) Appl. No.: 17/046,731

(22) PCT Filed: Apr. 10, 2019

(86) PCT No.: PCT/US2019/026840
§ 371 (c)(1),
(2) Date: Oct. 9, 2020

(87) PCT Pub. No.: WO2019/200007
PCT Pub. Date: Oct. 17, 2019

(65) Prior Publication Data
US 2021/0163621 A1 Jun. 3, 2021

Related U.S. Application Data

(60) Provisional application No. 62/655,725, filed on Apr. 10, 2018.

(51) Int. Cl.
| | | |
|---|---|---|
| *C07K 16/30* | (2006.01) | |
| *A61K 39/00* | (2006.01) | |
| *A61P 35/00* | (2006.01) | |
| *C07K 14/705* | (2006.01) | |
| *C12N 15/86* | (2006.01) | |

(52) U.S. Cl.
CPC .............. *C07K 16/30* (2013.01); *A61P 35/00* (2018.01); *C07K 14/70517* (2013.01); *C07K 14/70521* (2013.01); *C12N 15/86* (2013.01); *A61K 2039/505* (2013.01); *C07K 2317/565* (2013.01); *C07K 2317/622* (2013.01); *C12N 2740/15041* (2013.01)

(58) Field of Classification Search
None
See application file for complete search history.

(56) References Cited

U.S. PATENT DOCUMENTS

| | | |
|---|---|---|
| 5,827,642 A | 10/1998 | Riddell et al. |
| 5,830,462 A | 11/1998 | Crabtree et al. |
| 5,834,266 A | 11/1998 | Crabtree et al. |
| 5,869,337 A | 2/1999 | Crabtree et al. |
| 6,040,177 A | 3/2000 | Riddell et al. |
| 6,165,787 A | 12/2000 | Crabtree et al. |
| 6,319,494 B1 | 11/2001 | Capon et al. |
| 6,797,514 B2 | 9/2004 | Berenson et al. |
| 6,867,041 B2 | 3/2005 | Berenson et al. |
| 6,905,874 B2 | 6/2005 | Berenson et al. |
| 7,741,465 B1 | 6/2010 | Eshhar et al. |
| 8,436,183 B2 | 5/2013 | Holt et al. |
| 8,486,693 B2 | 7/2013 | Park et al. |
| 9,024,028 B2 | 5/2015 | Li et al. |
| 9,944,690 B2 | 4/2018 | Spencer et al. |
| 10,428,142 B2 | 10/2019 | Jarjour et al. |
| 10,934,346 B2 | 3/2021 | Foster et al. |
| 2003/0105000 A1* | 6/2003 | Pero ..................... C07K 1/047 514/19.3 |
| 2018/0044415 A1* | 2/2018 | Escarpe ............. C07K 16/2815 |

FOREIGN PATENT DOCUMENTS

| | | |
|---|---|---|
| WO | 2012/079000 A1 | 6/2012 |
| WO | 2012/129514 A1 | 9/2012 |
| WO | 2014/127261 A1 | 8/2014 |
| WO | 2015/090229 A1 | 6/2015 |
| WO | 2015/120096 A2 | 8/2015 |
| WO | 2016/138038 A1 | 9/2016 |
| WO | 2017/021349 A1 | 2/2017 |
| WO | WO-2017021349 A1 * | 2/2017 ........ A61K 39/00113 |
| WO | WO-2017173410 A1 * | 10/2017 ............. A61K 35/17 |

OTHER PUBLICATIONS

Rudikoff et al. (PNAS USA, 1982, 79: 1979-1983) (Year: 1982).*
Coleman et al. (Research in Immunology, 1994; 145(1): 33-36) (Year: 1994).*
Burgess et al. (J of Cell Bio. 111:2129-2138, 1990) (Year: 1990).*
Ibragimova and Wade (Biophysical Journal, Oct. 1999, vol. 77, pp. 2191-2198) (Year: 1999).*
Almagro & Fransson, Frontiers in Bioscience 2008; 13:1619-33 (Year: 2008).*
Prazma and Tedder (Immunology Letters 2008, 115: 1-8) (Year: 2008).*
Jena et al. (Blood Aug. 19, 2010 116(7): 1035-1044) (Year: 2010).*
Gura (Science, 1997, 278:1041-1042) (Year: 1997).*
Kaiser (Science, 2006, 313: 1370) (Year: 2006).*
Byers et al., Phase 1 study of AMG 119, a chimeric antigen receptor (CAR) T cell therapy targeting DLL3, in patients with relapsed/refractory small cell lung cancer (SCLC), Journal of Clinical Oncology (2019), 37(15):1-3 Retrieved from the Internet: URL:https://ascopubs.org/doi/abs/10.1200/JCO.2019.37.15 suppl.TPS8576?af=R [retrieved on Jun. 11, 2019] the whole document.
(Continued)

*Primary Examiner* — Peter J Reddig
(74) *Attorney, Agent, or Firm* — Susan E. Lingenfelter

(57) ABSTRACT

Antigen binding molecules, chimeric receptors, and engineered immune cells to DLL3 are disclosed in accordance with the invention. The invention further relates to vectors, compositions, and methods of treatment and/or detection using the DLL3 antigen binding molecules and engineered immune cells.

14 Claims, 12 Drawing Sheets

Specification includes a Sequence Listing.

(56) References Cited

OTHER PUBLICATIONS

Giffin et al., Targeting DLL3 with AMG 757, a BiTE Antibody Construct, and AMG 119, a CAR-T, for the Treatment of SCLC, Abstracts (2018), Retrieved from the Internet: URL:https://www.jto.org/article/S1556-0864(18)32784-9/pdf [retrieved on Jun. 11, 2019] the whole document.
Saunders et al., A DLL3-targeted antibody-drug conjugate eradicates high-grade pulmonary neuroendocrine tumor-initiating cells in vivo, Science Translational Medicine (2015), 7(302):1-15.
Enstone et al., The Economic Burden of Small Cell Lung Cancer: A Systematic Review of the Literature, PharmacoEconomics-Open (2017), 2:125-139.
Bunn et al., Small Cell Lung Cancer: Can Recent Advanced in Biology and Molecular Biology be Translated into Improved Outcomes?, J. Thoracic Oncology (2016), 11(4):453-474.
Siegel et al., Cancer Statistics, CA Cancer J. Clin. (2016), 66:7-30, DOI: 10.3222/caac.21332.
Geffers et al., Divergent Functions and Distant Localization of the Notch Ligands DLL1 and DLL3 in vivo, J. Cell Biol. (2007), 178(3):465-476.
Hombach et al., OX40 Costimulation by a Chimeric Antigen Receptor Abrogates CD28 and IL-2 Induced IL-10 Secretion by Redirected CD4 T Cells, Oncoimmunology (2012), 1(4):458-466.
Guedan et al., ICOS-Based Chimeric Antigen Receptors Program Bipolar TH17/TH1 Cells, Blood (2014), 124(7).
Shen et al., Chimeric Antigen Receptor Containing ICOS Signaling Domain Mediates Specific and Efficient Antitumor Effect of T Cells Against EGFRvIII Expressing Glioma, Journal of Hematology & Oncology (2013), 6(33):1-7.
Song et al., Pro-Survival Signaling via CD27 Costimulation Drives Effective CAR T-Cell Therapy, Oncoimmunology (2012), 1(4):547-549.
Eshhar et al., Tumor-Specific T-Bodies: Towards Clinical Application, Cancer Immunol. Immunotherapy (1997) 45:131-136.
Krause et al., Antigen-Dependent CD28 Signaling Slectively Enhances Survival and Proliferation in Genetically Modified Activated Human Primary T Lymphocytes, J. Exp. Med. (1998), 188(4):619-626.
Finney et al., Chimeric Receptors Providing Both Primary and Costimulatory Signaling in T Cells from a Single Gene Product, Journal of Immunology (1998) 161:2791-2797.
Song et al., CD27 Costimulation Augments the Survival and Antitumor Activity of Redirected Human T Cells In Vivo, Blood (2012), 119:696-706.
Kalos et al., T Cells with Chimeric Antigen Receptors Have Potent Antitumor Effects and Can Establish Memory in Patients with Advanced Leukemia, Sci. Transl. Med. (2011), 3(95):1-11.
Porter et al., Chimeric Antigen Receptor-Modified T Cells in Chronic Lymphoid Leukemia, N. Engl. J. Med. (2011), 365:725-733.
Gross et al., Therapeutic Potential of T Cell Chimeric Antigen Receptors (CARs) in Cancer Treatment: Counteracting Off-Tumor Toxicities for Safe CAR T Cell Therapy, Annu. Rev. Pharmacol. Toxicol. (2016), 56:59-83.
Kabat et al., (Seqs of Proteins of Immunological Interest (NIH, Bethesda, MD (1987 and 1991).
Chothia et al., Canonical Structures for the Hypervariable Regions of Immunoglobulins, J. Mol. Biol. (1987), 196:901-917.
Chothia et al., Confirmations of Immunoglobulin Hypervariable Regions, Nature (1989) 342:877-883.
MacCallum et al., Antibody-Antigen Interactions: Contact Analysis and Binding Site Topography, J. Mol. Biol. (1996), 262:732-745.
Martin et al., Structural Families in Loops of Homologous Proteins: Automatic Classification, Modeling and Application to Antibodies, J. Mol. Biol. (1996), 263:800-815.
Stahli et al., Distinction of Epitopes by Monoclonal Antibodies, Methods in Enzymology (1983), 92:242-253.
Kirkland et al., Analysis of the Fine Specificity and Cross-Reactivity of Monoclonal Anti-Lipid A Antibodies, J. Immunol. (1986), 137:3614-3619.
Morel et al., Monoclonal Antibodies to Bovine Serum Albumin: Affinity and Specificity Determinations, Molec. Immunol. (1988), 25(1):7-15.
Cheung et al., Epitope-Specific Antibody Response to the Surface Antigen of Duck Hepatitis B Virus in Infected Ducks, Virology (1990), 176:546-552.
Moldenhauer et al., Identity of HML-1 Antigen on Intestinal Intraepithelial T Cells and of B-Ly7 Antigen on Hairy Cell Leukaemia, Scand. J. Immunol. (1990), 32:77-82.
Wu et al., Remote Control of Therapeutic T Cells Through a Small Molecule-Gated Chimeric Receptor, Science (2014) 350(6258):1-9.
Fegan et al., Chemically Controlled Protein Assembly: Techniques and Applications, Chem. Rev. (2010), 110:3315-3336.
Hombach et al., Tumor-Specific T Cell Activation by Recombinant Immunoreceptors: CD3ζ Signaling and CD28 Costimulation are Simultaneously Required for Efficient IL-2 Secretion and Can be Integrated Into One Combined CD28/CD3ζ Signaling Receptor Molecule, Journal of Immunol. (2001), 167:6123-6131.
Lovelock et al., Prevention of Freezing Damage to Living Cells by Dimethyl Sulphoxide, Nature (1959), 183:1394-1395.
Rinfret, A., Factors Affecting the Erythrocyte During Rapid Freezing and Thawing, Ann N Y Acad Sci. Apr. 13, 1960:85:576-94.
Sloviter et al., Recovery and Transfusion of Human Erythrocytes After Freezing in Polyglycol Solutions, Nature (1962),196:899-900.
Graham et al., A New Technique for the Assay of Infectivity of Human Adenovirus 5 DNA, Virology (1973), 52:456-467.
Chu et al., SV40 DNA Transfection of Cells in Suspension: Analysis of the Efficiency of Transcription and Translation of T-Antigen, Gene (1981), 13:197-202.
Devereux et al., A Comprehensive Set of Sequence Analysis Porograms for the VAX, Nucl. Acid. Res. (1984), 12(1):387-395.
Dayhoff et al., A Model of Evolutionary Change in Proteins, Atlas of Protein Sequence and Structure (1978), 5:345-352.
Henikoff et al., Amino Acid Substitution Matrices from Protein Blocks, Proc. Natl. Acad. Sci. U.S.A. (1992), 89:10915-10919.
Kyte et al., A Simple Method for Displaying the Hydropathic Character of a Protein, J. Molecular Biology (1982), 157:105-131.
Fauchere, J., Elements for the Rational Design of Peptide Drugs, Advances in Drug Research (1986), 15:29-69.
Veber & Freidinger, The Design of Metabolically-Stable Peptide Analogs, TINS (1985), 392.
Evans et al., Design of Nonpeptidal Ligands for a Peptide Receptor: Cholecystokinin Antagonists, J. Med. Chem. (1987), 30:1229-1239.

* cited by examiner

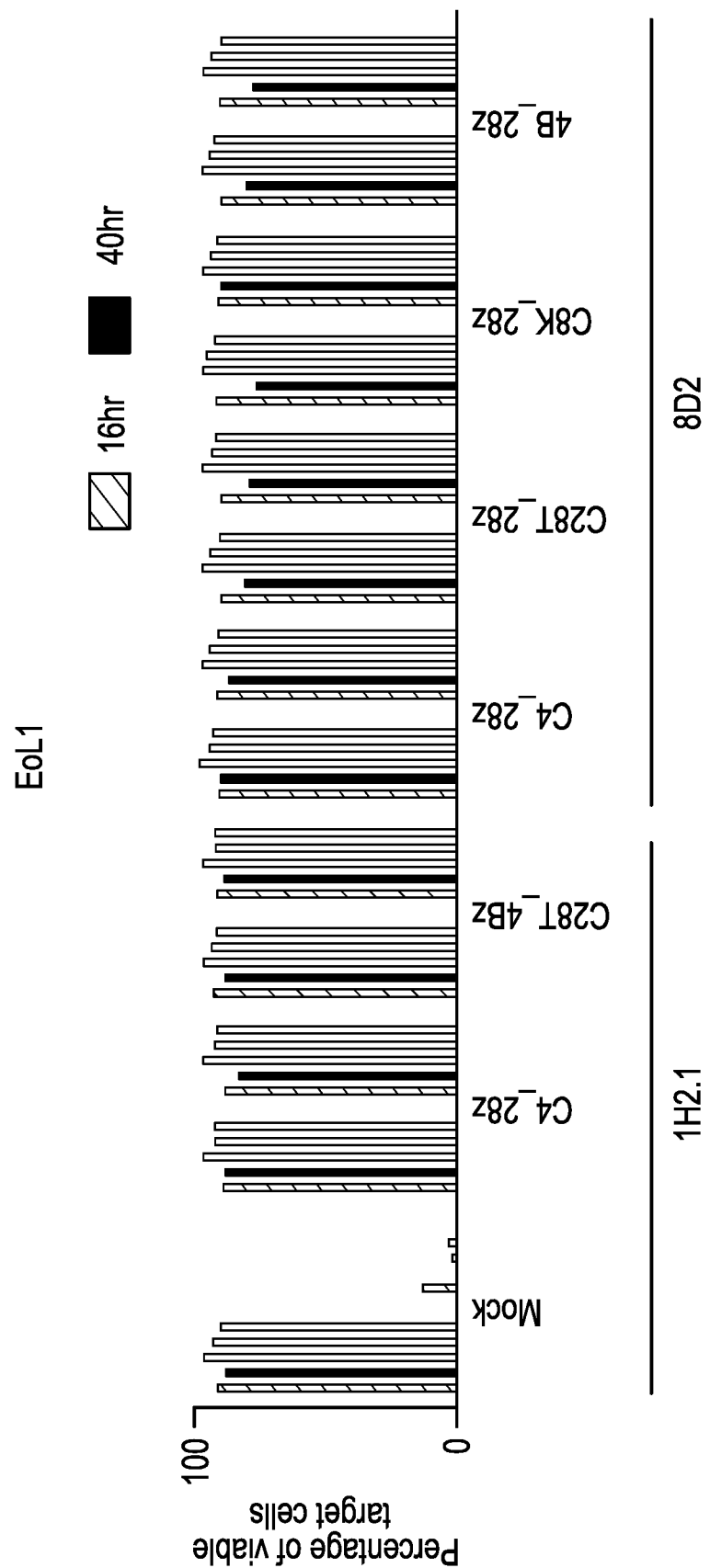

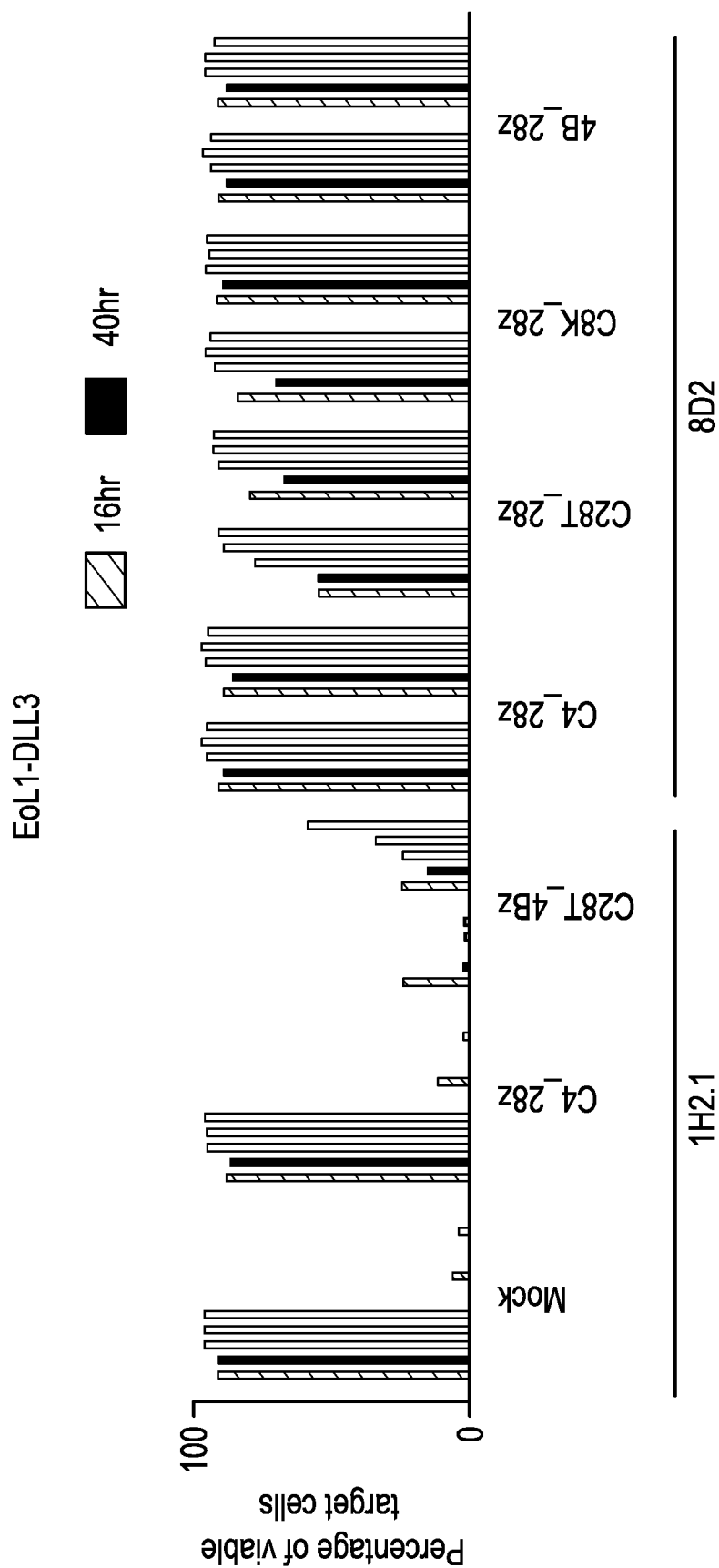

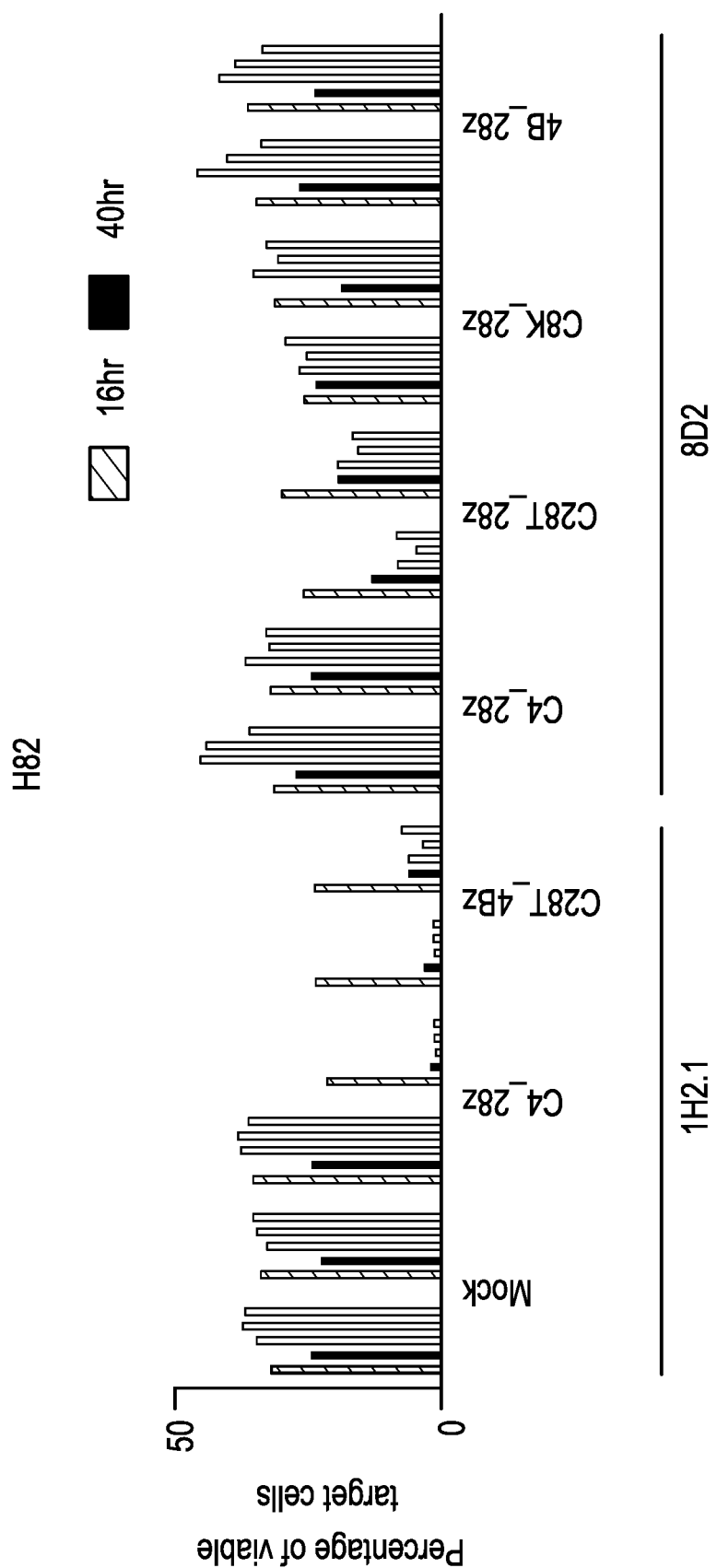

SEQUENCE LISTING

```
<160> NUMBER OF SEQ ID NOS: 70

<210> SEQ ID NO 1
<211> LENGTH: 294
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
cttgataatg aaaagtcaaa cggaacaatc attcacgtga agggcaagca cctctgtccg      60
tcacccttgt tccctggtcc atccaagcca ttctgggtgt tggtcgtagt gggtggagtc     120
ctcgcttgtt actctctgct cgtcaccgtg gcttttataa tcttctgggt tagatccaaa     180
agaagccgcc tgctccatag cgattacatg aatatgactc cacgccgccc tggccccaca     240
aggaaacact accagcctta cgcaccacct agagatttcg ctgcctatcg gagc           294

<210> SEQ ID NO 2
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Leu Asp Asn Glu Lys Ser Asn Gly Thr Ile Ile His Val Lys Gly Lys
1               5                   10                  15
```

```
His Leu Cys Pro Ser Pro Leu Phe Pro Gly Pro Ser Lys Pro Phe Trp
             20                  25                  30

Val Leu Val Val Val Gly Gly Val Leu Ala Cys Tyr Ser Leu Leu Val
         35                  40                  45

Thr Val Ala Phe Ile Ile Phe Trp Val Arg Ser Lys Arg Ser Arg Leu
     50                  55                  60

Leu His Ser Asp Tyr Met Asn Met Thr Pro Arg Arg Pro Gly Pro Thr
 65                  70                  75                  80

Arg Lys His Tyr Gln Pro Tyr Ala Pro Pro Arg Asp Phe Ala Ala Tyr
                 85                  90                  95

Arg Ser

<210> SEQ ID NO 3
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cttgataatg aaaagtcaaa cggaacaatc attcacgtga agggcaagca cctctgtccg      60
tcacccttgt tccctggtcc atccaagcca                                      90

<210> SEQ ID NO 4
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Leu Asp Asn Glu Lys Ser Asn Gly Thr Ile Ile His Val Lys Gly Lys
 1               5                  10                  15

His Leu Cys Pro Ser Pro Leu Phe Pro Gly Pro Ser Lys Pro
             20                  25                  30

<210> SEQ ID NO 5
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ttctgggtgt tggtcgtagt gggtggagtc ctcgcttgtt actctctgct cgtcaccgtg      60
gcttttataa tcttctgggt t                                               81

<210> SEQ ID NO 6
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6
```

```
Phe Trp Val Leu Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 7
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7

```
agatccaaaa gaagccgcct gctccatagc gattacatga atatgactcc acgccgccct      60
ggccccacaa ggaaacacta ccagccttac gcaccaccta gagatttcgc tgcctatcgg     120
agc                                                                   123
```

<210> SEQ ID NO 8
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 9
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
agggtgaagt tttccagatc tgcagatgca ccagcgtatc agcagggcca gaaccaactg      60
tataacgagc tcaacctggg acgcagggaa gagtatgacg ttttggacaa gcgcagagga     120
cgggaccctg agatgggtgg caaaccaaga cgaaaaaacc cccaggaggg tctctataat     180
gagctgcaga aggataagat ggctgaagcc tattctgaaa taggcatgaa aggagagcgg     240
agaaggggaa aagggcacga cggttttgtac cagggactca gcactgctac gaaggatact     300
tatgacgctc tccacatgca agccctgcca cctagg                               336
```

<210> SEQ ID NO 10
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
attgaggtga tgtatccacc gccttacctg gataacgaaa agagtaacgg taccatcatt    60
cacgtgaaag gtaaacacct gtgtccttct cccctcttcc ccgggccatc aaagccc      117

<210> SEQ ID NO 12
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 13
<211> LENGTH: 288
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13
gctgcagcat tgagcaactc aataatgtat tttagtcact tgtaccagt gttcttgccg     60 gctaagccta ctaccacacc cgctccacgg ccacctaccc cagctcctac catcgcttca   120
cagcctctgt ccctgcgccc agaggcttgc cgaccggccg caggggcgc tgttcatacc    180 agaggactgg atttcgcctg cgatatctat atctgggcac ccctggccgg aacctgcggc   240
gtactcctgc tgtccctggt catcacgctc tattgtaatc acaggaac    288

<210> SEQ ID NO 14
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ala Ala Ala Leu Ser Asn Ser Ile Met Tyr Phe Ser His Phe Val Pro
1               5                   10                  15

Val Phe Leu Pro Ala Lys Pro Thr Thr Thr Pro Ala Pro Arg Pro Pro
            20                  25                  30

Thr Pro Ala Pro Thr Ile Ala Ser Gln Pro Leu Ser Leu Arg Pro Glu
        35                  40                  45

Ala Cys Arg Pro Ala Ala Gly Gly Ala Val His Thr Arg Gly Leu Asp
    50                  55                  60

Phe Ala Cys Asp Ile Tyr Ile Trp Ala Pro Leu Ala Gly Thr Cys Gly
65                  70                  75                  80

Val Leu Leu Leu Ser Leu Val Ile Thr Leu Tyr Cys Asn His Arg Asn
                85                  90                  95

<210> SEQ ID NO 15
<211> LENGTH: 141
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
cgcttttccg tcgttaagcg ggggagaaaa aagctgctgt acattttcaa acagccgttt    60
atgaggccgg tccaaacgac tcaggaagag gacggctgct cctgccgctt tcctgaggag    120
gaggagggcg ggtgcgaact g                                              141

<210> SEQ ID NO 16
<211> LENGTH: 47
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 17
<211> LENGTH: 1449
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 17

```
atggcactcc cgtaactgc tctgctgctg ccgttggcat tgctcctgca cgccgcacgc       60
ccgcaggtgc aactgcagga aagcgggccc ggtctggtga agccctcaga acgctctcc      120
ctcacctgta cagtctctgg cgattcaatc tcttcatatt actggacgtg gatcaggcag     180
cctcccggca agggactgga gtggatcgga tatatctact atagtggcac cactaactat     240
aatccttccc tgaaaagccg ggtgacaatc tctgttgaca cctccaagag ccagttcagc     300
ctgaaactct ccagtgtgac agccgccgat acagccgtgt attactgtgc ctctatcgct     360
gtgcgcgggt tcttttttga ttattgggc aggggacac tggtgaccgt tagcagcggg       420
ggaggagggt ccggtggcgg cggcagcgga ggcggggggtt cagaaattgt actgacccag    480
tcccccggca cgctctctct ctccccaggg gaaagggcaa cccttagctg ccgggcgagc     540
cagagcgtga gttcctccta cctcgcgtgg tatcagcaga agcctggaca ggctcccaga     600
ctgctgattt acggggcttc tacgagagcc accggcatac ctgataggtt ctctggctcc     660
gggtctggga ccgactttac tcttacaatc agcagacttg agcctgaaga cttcgctgtg     720
tattattgtc aacaatacgg aacgtccccc cttacctttg gtggcgggac aaaagtggaa     780
attaagaggg ccgctgccct tgataatgaa aagtcaaacg gaacaatcat tcacgtgaag     840
ggcaagcacc tctgtccgtc acccttgttc cctggtccat ccaagccatt ctgggtgttg     900
gtcgtagtgg gtggagtcct cgcttgttac tctctgctcg tcaccgtggc ttttataatc     960
ttctggggttc gcttttccgt cgttaagcgg gggagaaaaa agctgctgta cattttcaaa   1020
cagccgttta tgaggccggt ccaaacgact caggaagaag acggctgctc ctgccgcttt   1080
cctgaggagg aggagggcgg gtgcgaactg agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaaggggaa aagggcacga cggttttgtac   1380
cagggactca gcactgctac gaaggatact tatgacgctc tccacatgca agccctgcca   1440
cctaggtaa                                                             1449
```

<210> SEQ ID NO 18
<211> LENGTH: 482
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 18

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Asp
        35                  40                  45

Ser Ile Ser Ser Tyr Tyr Trp Thr Trp Ile Arg Gln Pro Pro Gly Lys
    50                  55                  60
```

```
Gly Leu Glu Trp Ile Gly Tyr Ile Tyr Tyr Ser Gly Thr Thr Asn Tyr
 65                  70                  75                  80

Asn Pro Ser Leu Lys Ser Arg Val Thr Ile Ser Val Asp Thr Ser Lys
                 85                  90                  95

Ser Gln Phe Ser Leu Lys Leu Ser Ser Val Thr Ala Ala Asp Thr Ala
            100                 105                 110

Val Tyr Tyr Cys Ala Ser Ile Ala Val Arg Gly Phe Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Gly Thr Leu Ser Leu Ser Pro Gly Glu Arg Ala Thr Leu Ser
                165                 170                 175

Cys Arg Ala Ser Gln Ser Val Ser Ser Ser Tyr Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Asp Arg Phe Ser Gly Ser Gly Ser Gly Thr
210                 215                 220

Asp Phe Thr Leu Thr Ile Ser Arg Leu Glu Pro Glu Asp Phe Ala Val
225                 230                 235                 240

Tyr Tyr Cys Gln Gln Tyr Gly Thr Ser Pro Leu Thr Phe Gly Gly Gly
                245                 250                 255

Thr Lys Val Glu Ile Lys Arg Ala Ala Ala Leu Asp Asn Glu Lys Ser
            260                 265                 270

Asn Gly Thr Ile Ile His Val Lys Gly Lys His Leu Cys Pro Ser Pro
        275                 280                 285

Leu Phe Pro Gly Pro Ser Lys Pro Phe Trp Val Leu Val Val Val Gly
290                 295                 300

Gly Val Leu Ala Cys Tyr Ser Leu Leu Val Thr Val Ala Phe Ile Ile
305                 310                 315                 320

Phe Trp Val Arg Phe Ser Val Val Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg
```

<210> SEQ ID NO 19
<211> LENGTH: 1431
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

```
atggcactcc ccgtaactgc tctgctgctg ccgttggcat tgctcctgca cgccgcacgc      60
ccgcaggtgc aactgcagga aagcgggccc ggtctggtga agccctcaga aacgctctcc     120
ctcacctgta cagtctctgg cgattcaatc tcttcatatt actggacgtg gatcaggcag     180
cctcccggca agggactgga gtggatcgga tatatctact atagtggcac cactaactat     240
aatccttccc tgaaaagccg ggtgacaatc tctgttgaca cctccaagag ccagttcagc     300
ctgaaactct ccagtgtgac agccgccgat acagccgtgt attactgtgc ctctatcgct     360
gtgcgcgggt tctttttttga ttattgggggc caggggacac tggtgaccgt tagcagcggg     420
ggaggagggt ccggtggcgg cggcagcgga ggcgggggtt cagaaattgt actgacccag     480
tccccccggca cgctctctct ctccccaggg gaaagggcaa cccttagctg ccgggcgagc     540
cagagcgtga gttcctccta cctcgcgtgg tatcagcaga agcctggaca ggctcccaga     600
ctgctgattt acggggcttc tacgagagcc accggcatac tgataggtt ctctggctcc     660
gggtctggga ccgactttac tcttacaatc agcagacttg agcctgaaga cttcgctgtg     720
tattattgtc aacaatacgg aacgtccccc cttaccttttg gtggcgggac aaaagtggaa     780
attaagaggg ccgctgccct tgataatgaa aagtcaaacg gaacaatcat tcacgtgaag     840
ggcaagcacc tctgtccgtc acccttgttc cctggtccat ccaagccatt ctgggtgttg     900
gtcgtagtgg gtggagtcct cgcttgttac tctctgctcg tcaccgtggc ttttataatc     960
ttctgggtta gatccaaaag aagccgcctg ctccatagcg attacatgaa tatgactcca    1020
cgccgccctg gccccacaag gaaacactac cagccttacg caccacctag agatttcgct    1080
gcctatcgga gccgagtgaa atttttctaga tcagctgatg ctcccgccta tcagcaggga    1140
cagaatcaac tttacaatga gctgaacctg ggtcgcagag aagagtacga cgttttggac    1200
aaacgccggg gccgagatcc tgagatgggg gggaagccga aaggaagaa tcctcaagaa    1260
ggcctgtaca acgagcttca aaaagacaaa atggctgagg cgtactctga gatcggcatg    1320
aagggcgagc ggagacgagg caagggtcac gatggcttgt atcagggcct gagtacagcc    1380
acaaaggaca cctatgacgc cctccacatg caggcactgc ccccacgcta g              1431
```

<210> SEQ ID NO 20
<211> LENGTH: 476
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Asp
              35                  40                  45

Ser Ile Ser Ser Tyr Tyr Trp Thr Trp Ile Arg Gln Pro Pro Gly Lys
 50                  55                  60

Gly Leu Glu Trp Ile Gly Tyr Ile Tyr Tyr Ser Gly Thr Thr Asn Tyr
 65              70                  75                  80

Asn Pro Ser Leu Lys Ser Arg Val Thr Ile Ser Val Asp Thr Ser Lys
                 85                  90                  95

Ser Gln Phe Ser Leu Lys Leu Ser Ser Val Thr Ala Ala Asp Thr Ala
            100                 105                 110

Val Tyr Tyr Cys Ala Ser Ile Ala Val Arg Gly Phe Phe Phe Asp Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Glu Ile Val Leu Thr Gln
145                 150                 155                 160

Ser Pro Gly Thr Leu Ser Leu Ser Pro Gly Glu Arg Ala Thr Leu Ser
                165                 170                 175

Cys Arg Ala Ser Gln Ser Val Ser Ser Ser Tyr Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Asp Arg Phe Ser Gly Ser Gly Ser Gly Thr
    210                 215                 220

Asp Phe Thr Leu Thr Ile Ser Arg Leu Glu Pro Glu Asp Phe Ala Val
225                 230                 235                 240

Tyr Tyr Cys Gln Gln Tyr Gly Thr Ser Pro Leu Thr Phe Gly Gly Gly
                245                 250                 255

Thr Lys Val Glu Ile Lys Arg Ala Ala Ala Leu Asp Asn Glu Lys Ser
            260                 265                 270

Asn Gly Thr Ile Ile His Val Lys Gly Lys His Leu Cys Pro Ser Pro
        275                 280                 285

Leu Phe Pro Gly Pro Ser Lys Pro Phe Trp Val Leu Val Val Val Gly
    290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
                325                 330                 335

Asn Met Thr Pro Arg Arg Pro Gly Pro Thr Arg Lys His Tyr Gln Pro
            340                 345                 350

Tyr Ala Pro Pro Arg Asp Phe Ala Ala Tyr Arg Ser Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr

Tyr Asp Ala Leu His Met Gln Ala Leu Pro Pro Arg
465 470 475

<210> SEQ ID NO 21
<211> LENGTH: 1458
<212> TYPE: DNA
<213> ORGANISM: Artificial Sequence
<220> FEATURE:
<221> NAME/KEY: source
<223> OTHER INFORMATION: /note="Description of Artificial Sequence:
  Synthetic polynucleotide"

<400> SEQUENCE: 21

| | | | | | |
|---|---|---|---|---|---|
| atggcactcc | ccgtaactgc | tctgctgctg | ccgttggcat | tgctcctgca | cgccgcacgc | 60 |
| ccgcaggtcc | agctggtgca | gtctggggca | gaggtgaaac | ggccgggtgc | aagcgtgaag | 120 |
| gtgtcctgca | aagcctctgg | ctatacccttt | actgggtact | atatgcactg | ggttcggcag | 180 |
| gcgccaggac | agggtcttga | gtggatgggt | tggattgatc | caaactctgg | cgatacaaat | 240 |
| tacgcacaga | aattccaggg | ccgcgtgacg | atgactcgag | acacttccat | atccaccgcc | 300 |
| tatatggaag | tgaatagact | ccggtctgac | gacactgctg | tctattactg | tgcaagggat | 360 |
| cccaaccggc | ggagttggta | ttacggaatg | gatgtctggg | cccagggtac | taccgtcacg | 420 |
| gtgtcttctg | gcggcggggg | ctcaggagga | ggaggcagcg | gtggaggagg | cagcgatatt | 480 |
| cagatgacac | aaagcccttc | tagtctctcc | gcaagcgttg | gcgaccgcgt | gaccattacg | 540 |
| tgtcaggctt | cacaagatat | tcgaaactac | ctgaactggt | atcagcagaa | gcccggcaaa | 600 |
| gcacctaagc | tgctgattta | tgacgctagc | aaccttgaga | ctggcgtccc | ctccagattt | 660 |
| tccggcagcg | gctcaggcac | cgactttact | tttaccatct | ccacactcca | gccagaagat | 720 |
| attgcaacgt | attactgcca | acattatgat | aacctgcctt | tgaccttcgg | aggtggcacc | 780 |
| aaggtagaga | tcagaagagc | cgctgcccctt | gataatgaaa | agtcaaacgg | aacaatcatt | 840 |
| cacgtgaagg | gcaagcacct | ctgtccgtca | cccttgttcc | ctggtccatc | caagccattc | 900 |
| tgggtgttgg | tcgtagtggg | tggagtcctc | gcttgttact | ctctgctcgt | caccgtggct | 960 |
| tttataatct | tctgggttcg | cttttccgtc | gttaagcggg | ggagaaaaaa | gctgctgtac | 1020 |
| attttcaaac | agccgtttat | gaggccggtc | caaacgactc | aggaagaaga | cggctgctcc | 1080 |
| tgccgctttc | ctgaggagga | ggagggcggg | tgcgaactga | gggtgaagtt | ttccagatct | 1140 |
| gcagatgcac | cagcgtatca | gcagggccag | aaccaactgt | ataacgagct | caacctggga | 1200 |
| cgcagggaag | agtatgacgt | tttggacaag | cgcagaggac | gggaccctga | gatgggtggc | 1260 |
| aaaccaagac | gaaaaaaccc | ccaggagggt | ctctataatg | agctgcagaa | ggataagatg | 1320 |
| gctgaagcct | attctgaaat | aggcatgaaa | ggagagcgga | gaaggggaaa | agggcacgac | 1380 |
| ggtttgtacc | agggactcag | cactgctacg | aaggatactt | atgacgctct | ccacatgcaa | 1440 |
| gccctgccac | ctaggtaa | | | | | 1458 |

<210> SEQ ID NO 22
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
  Synthetic polypeptide"

<400> SEQUENCE: 22

-continued

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Arg Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asp Pro Asn Ser Gly Asp Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Val Asn Arg Leu Arg Ser Asp Asp Thr
            100                 105                 110

Ala Val Tyr Tyr Cys Ala Arg Asp Pro Asn Arg Arg Ser Trp Tyr Tyr
        115                 120                 125

Gly Met Asp Val Trp Ala Gln Gly Thr Thr Val Thr Val Ser Ser Gly
    130                 135                 140

Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Gln Asp Ile Arg Asn Tyr Leu Asn
            180                 185                 190

Trp Tyr Gln Gln Lys Pro Gly Lys Ala Pro Lys Leu Leu Ile Tyr Asp
        195                 200                 205

Ala Ser Asn Leu Glu Thr Gly Val Pro Ser Arg Phe Ser Gly Ser Gly
    210                 215                 220

Ser Gly Thr Asp Phe Thr Phe Thr Ile Ser Thr Leu Gln Pro Glu Asp
225                 230                 235                 240

Ile Ala Thr Tyr Tyr Cys Gln His Tyr Asp Asn Leu Pro Leu Thr Phe
                245                 250                 255

Gly Gly Gly Thr Lys Val Glu Ile Arg Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Phe Ser Val Val Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
```

420                 425                 430
Asn Glu Leu Gln Lys Asp Lys Met Ala Glu Ala Tyr Ser Glu Ile Gly
            435                 440                 445

Met Lys Gly Glu Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 23
<211> LENGTH: 1440
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
atggcactcc ccgtaactgc tctgctgctg ccgttggcat tgctcctgca cgccgcacgc      60
ccgcaggtcc agctggtgca gtctggggca gaggtgaaac ggccgggtgc aagcgtgaag     120
gtgtcctgca agcctctggc tatacccttt actgggtact atatgcactg gttcgcag       180
gcgccaggac agggtcttga gtggatgggt tggattgatc caaactctgg cgatacaaat    240
tacgcacaga aattccaggg ccgcgtgacg atgactcgag acacttccat atccaccgcc    300
tatatggaag tgaatagact ccggtctgac gacactgctg tctattactg tgcaagggat    360
cccaaccggc ggagttggta ttacggaatg gatgtctggg cccagggtac taccgtcacg    420
gtgtcttctg gcggcggggg ctcaggagga ggaggcagcg gtggaggagg cagcgatatt    480
cagatgacac aaagcccttc tagtctctcc gcaagcgttg gcgaccgcgt gaccattacg    540
tgtcaggctt cacaagatat tcgaaactac ctgaactggt atcagcagaa gcccggcaaa    600
gcacctaagc tgctgattta tgacgctagc aaccttgaga ctggcgtccc ctccagattt    660
tccggcagcg gctcaggcac cgactttact tttaccatct ccacactcca gccagaagat    720
attgcaacgt attactgcca acattatgat aacctgcctt tgaccttcgg aggtggcacc    780
aaggtagaga tcagaagagc cgctgcccct gataatgaaa agtcaaacgg aacaatcatt    840
cacgtgaagg gcaagcacct ctgtccgtca cccttgttcc ctggtccatc caagccattc    900
tgggtgttgg tcgtagtggg tggagtcctc gcttgttact ctctgctcgt caccgtggct    960
tttataatct tctgggttag atccaaaaga agccgcctgc tccatagcga ttacatgaat   1020
atgactccac gccgcccctgg ccccacaagg aaacactacc agccttacgc accacctaga   1080
gatttcgctg cctatcggag ccgagtgaaa ttttctagat cagctgatgc tcccgcctat   1140
cagcagggac agaatcaact ttacaatgag ctgaacctgg gtcgcagaga agagtacgac   1200
gtttggaca acgccggggg ccgagatcct gagatggggg ggaagccgag aaggaagaat   1260
cctcaagaag gcctgtacaa cgagcttcaa aaagacaaaa tggctgaggc gtactctgag   1320
atcggcatga gggcgagcg gagacgaggc aagggtcacg atggcttgta tcagggcctg   1380
agtacagcca caaaggacac ctatgacgcc ctccacatgc aggcactgcc cccacgctag   1440

<210> SEQ ID NO 24
<211> LENGTH: 479
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 24
```

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Arg Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asp Pro Asn Ser Gly Asp Thr Asn
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Val Asn Arg Leu Arg Ser Asp Asp Thr
            100                 105                 110

Ala Val Tyr Tyr Cys Ala Arg Asp Pro Asn Arg Arg Ser Trp Tyr Tyr
        115                 120                 125

Gly Met Asp Val Trp Ala Gln Gly Thr Thr Val Thr Val Ser Ser Gly
    130                 135                 140

Gly Gly Gly Ser Gly Gly Gly Ser Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Gln Asp Ile Arg Asn Tyr Leu Asn
            180                 185                 190

Trp Tyr Gln Gln Lys Pro Gly Lys Ala Pro Lys Leu Leu Ile Tyr Asp
        195                 200                 205

Ala Ser Asn Leu Glu Thr Gly Val Pro Ser Arg Phe Ser Gly Ser Gly
    210                 215                 220

Ser Gly Thr Asp Phe Thr Phe Thr Ile Ser Thr Leu Gln Pro Glu Asp
225                 230                 235                 240

Ile Ala Thr Tyr Tyr Cys Gln His Tyr Asp Asn Leu Pro Leu Thr Phe
                245                 250                 255

Gly Gly Gly Thr Lys Val Glu Ile Arg Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
            405                 410                 415

Arg Arg Lys Asn Pro Gln Glu Gly Leu Tyr Asn Glu Leu Gln Lys Asp
        420                 425                 430

Lys Met Ala Glu Ala Tyr Ser Glu Ile Gly Met Lys Gly Glu Arg Arg
    435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465             470                 475

<210> SEQ ID NO 25
<211> LENGTH: 1437
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
atggcactcc ccgtaactgc tctgctgctg ccgttggcat tgctcctgca cgccgcacgc      60
ccgcaagtgc agttggtgca gtctggagct gaagtgaaga aaccaggcgc tagcgtcaaa     120
gtgagctgta aggcctcagg ttacacgttt actgggtact atatgcattg ggtcaggcaa     180
gccccctggc agggcctcga gtggatgggc tggattaatc ctaacagcgg ggacacaagc     240
tatgcccaac gcttcctggg cagagtaaca atgacacggg atacaagtat aacaccgtc     300
catatggaac tctctcggct cggctcagat gataccgcgg tttattactg tgctagggag     360
gacgactcct cttggtatgg cagcttcgat tattgggggc agggaacccct ggtgacagtc     420
tcatctggtg gagggggctc cgggggtggg ggcagcggag gggaggttc tgatatacag     480
atgactcaga gtccctcaag cttgagtgcc agtgtaggcg accgggtgac gataacctgt     540
agggcttcac agggaatcag aaattatctg ggttggtacc agcagaagcc aggaaaggca     600
cctaaaagac ttatttacgc cgcatcctcc ttgcagtccg gcgtgccatc aaaattttct     660
gggagcggct ctggaaccga gttcaccctc acgatctcca gcctccagcc cgaggacttt     720
gccacctact attgcctgca gcacgatagt gatctgcgaa cttttgggca aggcactaaa     780
gtggaaatta gagagccgc tgcccttgat aatgaaaagt caaacggaac aatcattcac     840
gtgaagggca agcacctctg tccgtcaccc ttgttccctg tccatccaa gccattctgg     900
gtgttggtcg tagtgggtgg agtcctcgct tgttactctc tgctcgtcac cgtggctttt     960
ataatcttct gggttagatc caaaagaagc cgcctgctcc atagcgatta catgaatatg    1020
actccacgcc gccctggccc cacaaggaaa cactaccagc cttacgcacc acctagagat    1080
ttcgctgcct atcggagccg agtgaaattt tctagatcag ctgatgctcc cgcctatcag    1140
cagggacaga tcaacttta caatgagctg aacctgggtc gcagagaaga gtacgacgtt    1200
ttggacaaac gccggggccg agatcctgag atggggggga agccgagaag gaagaatcct    1260
caagaaggcc tgtacaacga gcttcaaaaa gacaaaatgg ctgaggcgta ctctgagatc    1320
ggcatgaagg gcgagcggag acgaggcaag ggtcacgatg gcttgtatca gggcctgagt    1380
acagccacaa aggacaccta tgacgcccctc cacatgcagg cactgccccc acgctag     1437

```
<210> SEQ ID NO 26
<211> LENGTH: 478
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26
```

Met Ala Leu Pro Val Thr Ala Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Gly Tyr Tyr Met His Trp Val Arg Gln Ala Pro Gly Gln
        50                  55                  60

Gly Leu Glu Trp Met Gly Trp Ile Asn Pro Asn Ser Gly Asp Thr Ser
65                  70                  75                  80

Tyr Ala Gln Arg Phe Leu Gly Arg Val Thr Met Thr Arg Asp Thr Ser
                85                  90                  95

Ile Asn Thr Val His Met Glu Leu Ser Arg Leu Gly Ser Asp Asp Thr
            100                 105                 110

Ala Val Tyr Tyr Cys Ala Arg Glu Asp Asp Ser Ser Trp Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Gly Ile Arg Asn Tyr Leu Gly Trp
            180                 185                 190

Tyr Gln Gln Lys Pro Gly Lys Ala Pro Lys Arg Leu Ile Tyr Ala Ala
        195                 200                 205

Ser Ser Leu Gln Ser Gly Val Pro Ser Lys Phe Ser Gly Ser Gly Ser
    210                 215                 220

Gly Thr Glu Phe Thr Leu Thr Ile Ser Ser Leu Gln Pro Glu Asp Phe
225                 230                 235                 240

Ala Thr Tyr Tyr Cys Leu Gln His Asp Ser Asp Leu Arg Thr Phe Gly
                245                 250                 255

Gln Gly Thr Lys Val Glu Ile Lys Arg Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
                450                 455                 460

Asp Thr Tyr Asp Ala Leu His Met Gln Ala Leu Pro Pro Arg
465                 470                 475

<210> SEQ ID NO 27
<211> LENGTH: 1455
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

| | | | | | |
|---|---|---|---|---|---|
| atggcactcc | ccgtaactgc | tctgctgctg | ccgttggcat | tgctcctgca | cgccgcacgc | 60 |
| ccgcaagtgc | agttggtgca | gtctggagct | gaagtgaaga | accaggcgc | tagcgtcaaa | 120 |
| gtgagctgta | aggcctcagg | ttacacgttt | actgggtact | atatgcattg | ggtcaggcaa | 180 |
| gcccctggcc | agggcctcga | gtggatgggc | tggattaatc | ctaacagcgg | ggacacaagc | 240 |
| tatgcccaac | gcttcctggg | cagagtaaca | atgacacggg | atacaagtat | aacaccgtc | 300 |
| catatggaac | tctctcggct | cggctcagat | gataccgcgg | tttattactg | tgctagggag | 360 |
| gacgactcct | cttggtatgg | cagcttcgat | tattggggc | agggaaccct | ggtgacagtc | 420 |
| tcatctggtg | gaggggctc | cggggtggg | ggcagcggag | ggggaggttc | tgatatacag | 480 |
| atgactcaga | gtccctcaag | cttgagtgcc | agtgtaggcg | accgggtgac | gataacctgt | 540 |
| agggcttcac | agggaatcag | aaattatctg | ggttggtacc | agcagaagcc | aggaaaggca | 600 |
| cctaaaagac | ttatttacgc | cgcatcctcc | ttgcagtccg | gcgtgccatc | aaaatttct | 660 |
| gggagcggct | ctggaaccga | gttcacccctc | acgatctcca | gcctccagcc | cgaggacttt | 720 |
| gccacctact | attgcctgca | gcacgatagt | gatctgcgaa | cttttgggca | aggcactaaa | 780 |
| gtggaaatta | agagagccgc | tgcccttgat | aatgaaaagt | caaacggaac | aatcattcac | 840 |
| gtgaagggca | agcacctctg | tccgtcaccc | ttgttccctg | gtccatccaa | gccattctgg | 900 |
| gtgttggtcg | tagtgggtgg | agtcctgctt | tgttactctc | tgctcgtcac | cgtggctttt | 960 |
| ataatcttct | gggttcgctt | ttccgtcgtt | aagcggggga | gaaaaagct | gctgtacatt | 1020 |
| ttcaaacagc | cgtttatgag | gccggtccaa | acgactcagg | aagaagacgg | ctgctcctgc | 1080 |
| cgctttcctg | aggaggagga | gggcgggtgc | gaactgaggg | tgaagttttc | cagatctgca | 1140 |
| gatgcaccag | cgtatcagca | gggccagaac | caactgtata | acgagctcaa | cctgggacgc | 1200 |
| agggaagagt | atgacgtttt | ggacaagcgc | agaggacggg | accctgagat | gggtggcaaa | 1260 |
| ccaagacgaa | aaaccccca | ggagggtctc | tataatgagc | tgcagaagga | taagatggct | 1320 |
| gaagcctatt | ctgaaatagg | catgaaagga | gagcggagaa | ggggaaaagg | gcacgacggt | 1380 | ttgtaccagg gactcagcac tgctacgaag gatacttatg acgctctcca catgcaagcc    1440 ctgccaccta ggtaa                                                    1455

<210> SEQ ID NO 28
<211> LENGTH: 484
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Gly Tyr Tyr Met His Trp Val Arg Gln Ala Pro Gly Gln
    50                  55                  60

Gly Leu Glu Trp Met Gly Trp Ile Asn Pro Asn Ser Gly Asp Thr Ser
65                  70                  75                  80

Tyr Ala Gln Arg Phe Leu Gly Arg Val Thr Met Thr Arg Asp Thr Ser
                85                  90                  95

Ile Asn Thr Val His Met Glu Leu Ser Arg Leu Gly Ser Asp Asp Thr
            100                 105                 110

Ala Val Tyr Tyr Cys Ala Arg Glu Asp Asp Ser Ser Trp Tyr Gly Ser
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Gly Ile Arg Asn Tyr Leu Gly Trp
            180                 185                 190

Tyr Gln Gln Lys Pro Gly Lys Ala Pro Lys Arg Leu Ile Tyr Ala Ala
        195                 200                 205

Ser Ser Leu Gln Ser Gly Val Pro Ser Lys Phe Ser Gly Ser Gly Ser
    210                 215                 220

Gly Thr Glu Phe Thr Leu Thr Ile Ser Ser Leu Gln Pro Glu Asp Phe
225                 230                 235                 240

Ala Thr Tyr Tyr Cys Leu Gln His Asp Ser Asp Leu Arg Thr Phe Gly
                245                 250                 255

Gln Gly Thr Lys Val Glu Ile Lys Arg Ala Ala Ala Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Phe Ser Val Val Lys Arg Gly Arg Lys Lys
                325                 330                 335

```
Leu Leu Tyr Ile Phe Lys Gln Pro Phe Met Arg Pro Val Gln Thr Thr
                340                 345                 350

Gln Glu Glu Asp Gly Cys Ser Cys Arg Phe Pro Glu Glu Glu Glu Gly
            355                 360                 365

Gly Cys Glu Leu Arg Val Lys Phe Ser Arg Ser Ala Asp Ala Pro Ala
370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 29
<211> LENGTH: 618
<212> TYPE: PRT
<213> ORGANISM: Homo sapiens

<400> SEQUENCE: 29

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
                20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220
```

Ser Pro Glu His Gly Phe Cys Glu Gln Pro Gly Cys Arg Cys Leu
225                 230                 235                 240

Glu Gly Trp Thr Gly Pro Leu Cys Thr Val Pro Val Ser Thr Ser Ser
        245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
        450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
        515                 520                 525

Leu Ala Gly Thr Pro Glu Pro Ser Val His Ala Leu Pro Asp Ala Leu
530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
            595                 600                 605

Pro Tyr Pro Ser Ser Ile Leu Ser Val Lys
        610                 615

<210> SEQ ID NO 30
<211> LENGTH: 587

<212> TYPE: PRT
<213> ORGANISM: Homo sapiens

<400> SEQUENCE: 30

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400
```

Ala Asn Gly Gly Thr Cys Val Glu Gly Gly Ala His Arg Cys Ser
            405                 410                 415

Cys Ala Leu Gly Phe Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
            450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Leu Pro Pro Ala
            485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
            515                 520                 525

Leu Ala Gly Thr Pro Glu Pro Ser Val His Ala Leu Pro Asp Ala Leu
            530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
            565                 570                 575

Ile Ser Ala Pro Ser Ile Tyr Ala Arg Glu Ala
            580                 585

```
<210> SEQ ID NO 31
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
atggcactcc ccgtaactgc tctgctgctg ccgttggcat tgctcctgca cgccgcacgc    60
ccg                                                                 63

<210> SEQ ID NO 32
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32
```

Met Ala Leu Pro Val Thr Ala Leu Leu Leu Pro Leu Ala Leu Leu Leu
1               5                   10                  15

His Ala Ala Arg Pro
            20

```
<210> SEQ ID NO 33
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 33
ggcggtggag gctccggagg gggggctct ggcggagggg gctcc         45

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
gggtctacat ccggctccgg gaagcccgga agtggcgaag gtagtacaaa gggg    54

<210> SEQ ID NO 36
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Ser Thr Ser Gly Ser Gly Lys Pro Gly Ser Gly Glu Gly Ser Thr
1               5                   10                  15

Lys Gly

<210> SEQ ID NO 37
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
aagcggggga gaaaaaagct gctgtacatt ttcaaacagc cgtttatgag gccggtccaa    60
acgactcagg aagaagacgg ctgctcctgc cgctttcctg aggaggagga gggcgggtgc    120
gaactg                                                              126

<210> SEQ ID NO 38
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 39
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 40
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40
caggtgcaac tgcaggaaag cgggcccggt ctggtgaagc cctcagaaac gctctccctc      60
acctgtacag tctctggcga ttcaatctct tcatattact ggacgtggat caggcagcct    120
cccggcaagg gactggagtg gatcggatat atctactata gtggcaccac taactataat    180
ccttccctga aaagccgggt gacaatctct gttgacacct ccaagagcca gttcagcctg    240
aaactctcca gtgtgacagc cgccgataca gccgtgtatt actgtgcctc tatcgctgtg    300
cgcgggttct ttttgatta ttggggccag gggacactgg tgaccgttag cagc           354

<210> SEQ ID NO 41
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Tyr
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys

```
                50                  55                  60
Ser Arg Val Thr Ile Ser Val Asp Thr Ser Lys Ser Gln Phe Ser Leu
 65                  70                  75                  80

Lys Leu Ser Ser Val Thr Ala Ala Asp Thr Ala Val Tyr Tyr Cys Ala
                 85                  90                  95

Ser Ile Ala Val Arg Gly Phe Phe Phe Asp Tyr Trp Gly Gln Gly Thr
            100                 105                 110

Leu Val Thr Val Ser Ser
        115

<210> SEQ ID NO 42
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Tyr Tyr Trp Thr
 1               5

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Tyr Ile Tyr Tyr Ser Gly Thr Thr Asn Tyr Asn Pro Ser Leu Lys Ser
 1               5                  10                  15

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ile Ala Val Arg Gly Phe Phe Phe Asp Tyr
 1               5                  10

<210> SEQ ID NO 45
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
gaaattgtac tgacccagtc ccccggcacg ctctctctct ccccagggga agggcaacc      60 cttagctgcc gggcgagcca gagcgtgagt tcctcctacc tcgcgtggta tcagcagaag    120
cctggacagg ctcccagact gctgatttac ggggcttcta cgagagccac cggcatacct    180
gataggttct ctggctccgg gtctgggacc gactttactc ttacaatcag cagacttgag    240
```

```
cctgaagact tcgctgtgta ttattgtcaa caatacggaa cgtccccct taccttggt      300 ggcgggacaa aagtggaaat taagagg                                        327
```

<210> SEQ ID NO 46
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Leu Thr Phe Gly Gly Gly Thr Lys Val Glu Ile Lys Arg
            100                 105
```

<210> SEQ ID NO 47
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Arg Ala Ser Gln Ser Val Ser Ser Ser Tyr Leu Ala
1               5                   10
```

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

```
Gly Ala Ser Thr Arg Ala Thr
1               5
```

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gln Gln Tyr Gly Thr Ser Pro Leu Thr
1               5

<210> SEQ ID NO 50
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
caggtccagc tggtgcagtc tggggcagag gtgaaacggc cgggtgcaag cgtgaaggtg     60
tcctgcaaag cctctggcta tacctttact gggtactata tgcactgggt tcggcaggcg    120
ccaggacagg gtcttgagtg gatgggttgg attgatccaa actctggcga tacaaattac    180
gcacagaaat tccagggccg cgtgacgatg actcgagaca cttccatatc caccgcctat    240
atggaagtga atagactccg gtctgacgac actgctgtct attactgtgc aagggatccc    300
aaccggcgga gttggtatta cggaatggat gtctgggccc agggtactac cgtcacggtg    360
tcttct                                                               366
```

<210> SEQ ID NO 51
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asp Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Val Asn Arg Leu Arg Ser Asp Asp Thr Ala Val Tyr Tyr Cys
                85                  90                  95

Ala Arg Asp Pro Asn Arg Arg Ser Trp Tyr Tyr Gly Met Asp Val Trp
            100                 105                 110

Ala Gln Gly Thr Thr Val Thr Val Ser Ser
        115                 120

<210> SEQ ID NO 52
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Gly Tyr Tyr Met His
1               5

<210> SEQ ID NO 53
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Trp Ile Asp Pro Asn Ser Gly Asp Thr Asn Tyr Ala Gln Lys Phe Gln
1               5                   10                  15

Gly

<210> SEQ ID NO 54
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Pro Asn Arg Arg Ser Trp Tyr Tyr Gly Met Asp Val
1               5                   10

<210> SEQ ID NO 55
<211> LENGTH: 735
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
caggtccagc tggtgcagtc tggggcagag gtgaaacggc cgggtgcaag cgtgaaggtg      60
tcctgcaaag cctctggcta tacctttact gggtactata tgcactgggt tcggcaggcg     120
ccaggacagg gtcttgagtg gatgggttgg attgatccaa actctggcga tacaaattac     180
gcacagaaat tccagggccg cgtgacgatg actcgagaca cttccatatc caccgcctat     240
atggaagtga atagactccg gtctgacgac actgctgtct attactgtgc aagggatccc     300
aaccggcgga gttggtatta cggaatggat gtctgggccc agggtactac cgtcacggtg     360
tcttctggcg gcggggggctc aggaggagga ggcagcggtg gaggaggcag cgatattcag     420
atgacacaaa gcccttctag tctctccgca agcgttggcg accgcgtgac cattacgtgt     480
caggcttcac aagatattcg aaactacctg aactggtatc agcagaagcc cggcaaagca     540
cctaagctgc tgatttatga cgctagcaac cttgagactg gcgtcccctc cagattttcc     600
ggcagcggct caggcaccga ctttactttt accatctcca cactccagcc agaagatatt     660
gcaacgtatt actgccaaca ttatgataac ctgcctttga ccttcggagg tggcaccaag     720
gtagagatca gaaga                                                      735

<210> SEQ ID NO 56
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Thr Leu Gln Pro
65                  70                  75                  80

Glu Asp Ile Ala Thr Tyr Tyr Cys Gln His Tyr Asp Asn Leu Pro Leu
                85                  90                  95

Thr Phe Gly Gly Gly Thr Lys Val Glu Ile Arg Arg
            100                 105

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Ala Ser Gln Asp Ile Arg Asn Tyr Leu Asn
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asp Ala Ser Asn Leu Glu Thr
1               5

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln His Tyr Asp Asn Leu Pro Leu Thr Phe
1               5                   10

<210> SEQ ID NO 60
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

```
caagtgcagt tggtgcagtc tggagctgaa gtgaagaaac caggcgctag cgtcaaagtg      60
agctgtaagg cctcaggtta cacgtttact gggtactata tgcattgggt caggcaagcc     120
cctggccagg gcctcgagtg gatgggctgg attaatccta acagcgggga cacaagctat     180
gcccaacgct tcctgggcag agtaacaatg acacgggata caagtattaa caccgtccat     240 atgaactct ctcggctcgg ctcagatgat accgcggttt attactgtgc tagggaggac     300
gactcctctt ggtatggcag cttcgattat tgggggcagg gaaccctggt gacagtctca     360
tct                                                                    363
```

<210> SEQ ID NO 61
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asp Thr Ser Tyr Ala Gln Arg Phe
    50                  55                  60

Leu Gly Arg Val Thr Met Thr Arg Asp Thr Ser Ile Asn Thr Val His
65                  70                  75                  80

Met Glu Leu Ser Arg Leu Gly Ser Asp Asp Thr Ala Val Tyr Tyr Cys
                85                  90                  95

Ala Arg Glu Asp Asp Ser Ser Trp Tyr Gly Ser Phe Asp Tyr Trp Gly
            100                 105                 110

Gln Gly Thr Leu Val Thr Val Ser Ser
        115                 120
```

<210> SEQ ID NO 62
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

```
Gly Tyr Tyr Met His
1               5
```

<210> SEQ ID NO 63
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

```
Trp Ile Asn Pro Asn Ser Gly Asp Thr Ser Tyr Ala Gln Arg Phe Leu
1               5                   10                  15

Gly
```

<210> SEQ ID NO 64
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

```
Glu Asp Asp Ser Ser Trp Tyr Gly Ser Phe Asp Tyr
1               5                   10
```

<210> SEQ ID NO 65
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
gatatacaga tgactcagag tccctcaagc ttgagtgcca gtgtaggcga ccgggtgacg      60
ataacctgta gggcttcaca gggaatcaga aattatctgg gttggtacca gcagaagcca     120
ggaaaggcac ctaaaagact tatttacgcc gcatcctcct tgcagtccgg cgtgccatca     180
aaattttctg ggagcggctc tggaaccgag ttcaccctca cgatctccag cctccagccc     240
gaggactttg ccacctacta ttgcctgcag cacgatagtg atctgcgaac ttttgggcaa     300
ggcactaaag tggaaattaa gaga                                            324
```

<210> SEQ ID NO 66
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asp Ser Asp Leu Arg
                85                  90                  95

Thr Phe Gly Gln Gly Thr Lys Val Glu Ile Lys Arg
            100                 105
```

-continued

```
<210> SEQ ID NO 67
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Arg Ala Ser Gln Gly Ile Arg Asn Tyr Leu Gly
1               5                   10

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Ala Ser Ser Leu Gln Ser
1               5

<210> SEQ ID NO 69
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Leu Gln His Asp Ser Asp Leu Arg Thr Phe
1               5                   10

<210> SEQ ID NO 70
<211> LENGTH: 6762
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
ctgacgcgcc ctgtagcggc gcattaagcg cggcgggtgt ggtggttacg cgcagcgtga       60
ccgctacact tgccagcgcc ctagcgcccg ctcctttcgc tttcttccct tcctttctcg      120
ccacgttcgc cggctttccc cgtcaagctc taaatcgggg gctcccttta gggttccgat      180
ttagtgcttt acggcacctc gaccccaaaa aacttgatta gggtgatggt tcacgtagtg      240
ggccatcgcc ctgatagacg gttttcgcc ctttgacgtt ggagtccacg ttctttaata      300
gtggactctt gttccaaact ggaacaacac tcaaccctat ctcggtctat tcttttgatt      360
tataagggat tttgccgatt tcggcctatt ggttaaaaaa tgagctgatt taacaaaaat      420
ttaacgcgaa ttttaacaaa atattaacgc ttacaatttg ccattcgcca ttcaggctgc      480
gcaactgttg ggaagggcga tcggtgcggg cctcttcgct attacgccag ctggcgaaag      540
ggggatgtgc tgcaaggcga ttaagttggg taacgccagg gttttcccag tcacgacgtt      600
gtaaaacgac ggccagtgaa ttgtaatacg actcactata gggcgacccg gggatggcgc      660
gccagtaatc aattacgggg tcattagttc atagcccata tatggagttc cgcgttacat      720
```

```
aacttacggt aaatggcccg cctggctgac cgcccaacga cccccgccca ttgacgtcaa    780
taatgacgta tgttcccata gtaacgccaa tagggacttt ccattgacgt caatgggtgg    840
agtatttacg gtaaactgcc cacttggcag tacatcaagt gtatcatatg ccaagtacgc    900
cccctattga cgtcaatgac ggtaaatggc ccgcctggca ttatgcccag tacatgacct    960
tatgggactt tcctacttgg cagtacatct acgtattagt catcgctatt accatgctga   1020
tgcggttttg gcagtacatc aatgggcgtg gatagcggtt tgactcacgg ggatttccaa   1080
gtctccaccc cattgacgtc aatgggagtt tgttttggca ccaaaatcaa cgggactttc   1140
caaaatgtcg taacaactcc gccccattga cgcaaatggg cggtaggcgt gtacggtggg   1200
aggtctatat aagcagagct ggtttagtga accggggtct ctctggttag accagatctg   1260
agcctgggag ctctctggct aactagggaa cccactgctt aagcctcaat aaagcttgcc   1320
ttgagtgctt caagtagtgt gtgcccgtct gttgtgtgac tctggtaact agagatccct   1380 cagaccccttt tagtcagtgt ggaaaatctc tagcagtggc gcccgaacag ggacttgaaa   1440
gcgaaaggga accagagga gctctctcga cgcaggactc ggcttgctga agcgcgcacg   1500
gcaagaggcg aggggcggcg actggtgagt acgccaaaaa ttttgactag cggaggctag   1560
aaggagagag atgggtgcga gagcgtcagt attaagcggg ggagaattag atcgcgatgg   1620
gaaaaaattc ggttaaggcc agggggaaag aaaaaatata aattaaaaca tatagtatgg   1680
gcaagcaggg agctagaacg attcgcagtt aatcctggcc tgttagaaac atcagaaggc   1740
tgtagacaaa tactgggaca gctacaacca tcccttcaga caggatcaga gaacttaga   1800 tcattatata atacagtagc aaccctctat tgtgtgcatc aaaggataga gataaaagac   1860
accaaggaag ctttagacaa gatagaggaa gagcaaaaca aaagtaagac caccgcacag   1920
caagccgccg ctgatcttca gacctggagg aggagatatg agggacaatt ggagaagtga   1980
attatataaa tataaagtag taaaaattga accattagga gtagcaccca ccaaggcaaa   2040
gagaagagtg gtgcagagag aaaaaagagc agtgggaata ggagctttgt tccttgggtt   2100
cttgggagca gcaggaagca ctatgggcgc agcgtcaatg acgctgacgg tacaggccag   2160
acaattattg tctggtatag tgcagcagca gaacaatttg ctgagggcta ttgaggcgca   2220
acagcatctg ttgcaactca cagtctgggg catcaagcag ctccaggcaa gaatcctggc   2280
tgtggaaaga tacctaaagg atcaacagct cctggggatt tggggttgct ctggaaaact   2340
catttgcacc actgctgtgc cttggaatgc tagttggagt aataaatctc tggaacagat   2400
ttggaatcac acgacctgga tggagtggga cagagaaatt aacaattaca aagcttaat   2460 acactcctta attgaagaat cgcaaaacca gcaagaaaag aatgaacaag aattattgga   2520
attagataaa tgggcaagtt tgtggaattg gtttaacata acaaattggc tgtggtatat   2580
aaaattattc ataatgatag taggaggctt ggtaggttta agaatagttt tgctgtact   2640 ttctatagtg aatagagtta ggcagggata ttcaccatta tcgtttcaga cccacctccc   2700
aaccccgagg ggacccgaca ggcccgaagg aatagaagaa gaaggtggag agagagacag   2760
agacagatcc attcgattag tgaacggatc tcgacggtat cggttaactt ttaaaagaaa   2820
agggggattg gggggtaca gtgcagggga agaatagta gacataatag caacagacat   2880
acaaactaaa gaattacaaa aacaaattac aaaattcaaa attttatcgc gatcgcggaa   2940
tgaaagaccc cacctgtagg tttggcaagc tagcttaagt aacgccattt tgcaaggcat   3000
ggaaaataca taactgagaa tagagaagtt cagatcaagg ttaggaacag agagacagca   3060
```

```
gaatatgggc caaacaggat atctgtggta agcagttcct gccccggctc agggccaaga    3120
acagatggtc cccagatgcg gtcccgccct cagcagtttc tagagaacca tcagatgttt    3180
ccagggtgcc ccaaggacct gaaaatgacc ctgtgcctta tttgaactaa ccaatcagtt    3240
cgcttctcgc ttctgttcgc gcgcttctgc tccccgagct caataaaaga gcccacaacc    3300
cctcactcgg cgcgccagtc cttcgaagta gatctttgtc gatcctacca tccactcgac    3360
acacccgcca gcggccgctg ccaagcttcc gagctctcga attaattcac ggtacccacc    3420
atggcctagg gagactagtc gaatcgatat caacctctgg attacaaaat tgtgaaaga    3480
ttgactggta ttcttaacta tgttgctcct tttacgctat gtggatacgc tgctttaatg    3540
cctttgtatc atgctattgc ttcccgtatg gctttcattt tctcctcctt gtataaatcc    3600
tggttgctgt ctctttatga ggagttgtgg cccgttgtca ggcaacgtgg cgtggtgtgc    3660
actgtgtttg ctgacgcaac ccccactggt tggggcattg ccaccacctg tcagctcctt    3720
tccgggactt tcgctttccc cctcccgtatt gccacggcgg aactcatcgc cgcctgcctt    3780
gcccgctgct ggacaggggc tcggctgttg ggcactgaca attccgtggt gttgtcgggg    3840
aagctgacgt ccttttcatg gctgctcgcc tgtgttgcca cctggattct gcgcgggacg    3900
tccttctgct acgtccctttc ggccctcaat ccagcggacc ttccttcccg cggcctgctg    3960
ccggctctgc ggcctcttcc gcgtcttcgc cttcgccctc agacgagtcg gatctccctt    4020
tgggccgcct cccccgcctgg ttaattaaag taccttaaag accaatgact acaaggcag    4080
ctgtagatct tagccacttt ttaaaagaaa aggggggact ggaagggcga attcactccc    4140
aacgaagaca agatctgctt tttgcttgta ctgggtctct ctggttagac cagatctgag    4200
cctgggagct ctctggctaa ctagggaacc cactgcttaa gcctcaataa agcttgcctt    4260
gagtgcttca agtagtgtgt gcccgtctgt tgtgtgactc tggtaactag agatccctca    4320
gacccttttta gtcagtgtgg aaaatctcta gcaggcatgc cagacatgat aagatacatt    4380
gatgagtttg gacaaaccac aactagaatg cagtgaaaaa aatgctttat ttgtgaaatt    4440
tgtgatgcta ttgctttatt tgtaaccatt ataagctgca ataaacaagt taacaacaac    4500
aattgcattc attttatgtt tcaggttcag ggggaggtgt gggaggtttt ttggcgcgcc    4560
atcgtcgagg ttcccttttag tgagggttaa ttgcgagctt ggcgtaatca tggtcatagc    4620
tgtttcctgt gtgaaattgt tatccgctca caattccaca acaatacga gccgaagca    4680
taaagtgtaa agcctggggt gcctaatgag tgagctaact cacattaatt gcgttgcgct    4740
cactgcccgc tttccagtcg ggaaacctgt cgtgccagct gcattaatga atcggccaac    4800
gcgcggggag aggcggtttg cgtattgggc gctcttccgc ttcctcgctc actgactcgc    4860
tgcgctcggt cgttcggctg cggcgagcgg tatcagctca ctcaaaggcg gtaatacggt    4920
tatccacaga atcaggggat aacgcaggaa agaacatgtg agcaaaaggc cagcaaaagg    4980
ccaggaaccg taaaaaggcc gcgttgctgg cgttttttcca taggctccgc cccctgacg    5040
agcatcacaa aaatcgacgc tcaagtcaga ggtggcgaaa cccgacagga ctataaagat    5100
accaggcgtt tcccctggaa gctccctcg tgcgctctcc tgttccgacc ctgccgctta    5160
ccggatacct gtccgccttt ctcccttcgg aagcgtggc gctttctcat agctcacgct    5220
gtaggtatct cagttcggtg taggtcgttc gctccaagct gggctgtgtg cacgaacccc    5280
ccgttcagcc cgaccgctgc gccttatccg gtaactatcg tcttgagtcc aacccggtaa    5340
gacacgactt atcgccactg gcagcagcca ctggtaacag gattagcaga gcgaggtatg    5400
taggcggtgc tacagagttc ttgaagtggt ggcctaacta cggctacact agaagaacag    5460
```

```
tatttggtat ctgcgctctg ctgaagccag ttaccttcgg aaaaagagtt ggtagctctt    5520
gatccggcaa acaaaccacc gctggtagcg gtggtttttt tgtttgcaag cagcagatta    5580
cgcgcagaaa aaaaggatct caagaagatc ctttgatctt ttctacgggg tctgacgctc    5640
agtggaacga aaactcacgt taagggattt tggtcatgag attatcaaaa aggatcttca    5700
cctagatcct tttaaattaa aaatgaagtt ttaaatcaat ctaaagtata tatgagtaaa    5760
cttggtctga cagttaccaa tgcttaatca gtgaggcacc tatctcagcg atctgtctat    5820
ttcgttcatc catagttgcc tgactccccg tcgtgtagat aactacgata cgggagggct    5880
taccatctgg ccccagtgct gcaatgatac cgcgagaccc acgctcaccg gctccagatt    5940
tatcagcaat aaaccagcca gccggaaggg ccgagcgcag aagtggtcct gcaactttat    6000
ccgcctccat ccagtctatt aattgttgcc gggaagctag agtaagtagt tcgccagtta    6060
atagtttgcg caacgttgtt gccattgcta caggcatcgt ggtgtcacgc tcgtcgtttg    6120
gtatggcttc attcagctcc ggttcccaac gatcaaggcg agttacatga tcccccatgt    6180
tgtgcaaaaa agcggttagc tccttcggtc ctccgatcgt tgtcagaagt aagttggccg    6240
cagtgttatc actcatggtt atggcagcac tgcataattc tcttactgtc atgccatccg    6300
taagatgctt ttctgtgact ggtgagtact caaccaagtc attctgagaa tagtgtatgc    6360
ggcgaccgag ttgctcttgc ccggcgtcaa tacgggataa taccgcgcca catagcagaa    6420
ctttaaaagt gctcatcatt ggaaaacgtt cttcggggcg aaaactctca aggatcttac    6480
cgctgttgag atccagttcg atgtaaccca ctcgtgcacc caactgatct tcagcatctt    6540
ttactttcac cagcgtttct gggtgagcaa aacaggaag gcaaaatgcc gcaaaaaagg    6600
gaataagggc gacacggaaa tgttgaatac tcatactctt cctttttcaa tattattgaa    6660
gcatttatca gggttattgt ctcatgagcg gatacatatt tgaatgtatt tagaaaaata    6720
aacaaatagg ggttccgcgc acatttcccc gaaaagtgcc ac                      6762
```

CHIMERIC RECEPTORS TO DLL3 AND METHODS OF USE THEREOF

CROSS-REFERENCE TO RELATED APPLICATIONS

This application is a National Stage application under 35 U.S.C. § 371 of International Application No. PCT/US2019/026840, having an international filing date of Apr. 10, 2019, which claims the benefit of U.S. Provisional Patent Application No. 62/655,725, filed Apr. 10, 2018, all of which are incorporated herein by reference in their entirety for all purposes.

SEQUENCE LISTING

The instant application contains a Sequence Listing which has been submitted electronically in ASCII format and is hereby incorporated by reference in its entirety. Said ASCII copy, created on Apr. 10, 2019, is named A-2249-WO-PCT_SL.txt and is 86,327 bytes in size.

BACKGROUND OF THE INVENTION

Small cell lung cancer (SCLC) accounts for roughly 15% of all lung cancer cases diagnosed, but is an aggressive form of lung carcinoma (Enstone et al., (2017) Pharmacoecon Open doi: 10.1007/s41669-017-0045-0; Bunn et al. (2016) J Thorac Oncol; 11:453-74; Siegel et al., (2016) CA Cancer J Clin; 66:7-30). Delta-like 3 (DLL3) is a member of the Delta/Serrate/Lag-2 family of ligands for the Notch receptor and is thought to play a role in Notch signaling. DLL3 is an inhibitory ligand of the Notch signaling pathway normally expressed exclusively on intracellular membranes (Geffers et al. (2007) J Cell Biol; 178:465-76.). Representative DLL3 protein orthologs include, but are not limited to, human (Accession Nos. NP_058637 and NP 982353), chimpanzee (Accession No. XP_003316395), mouse (Accession No. NP_031892), and rat (Accession No. NP_446118). In humans, the DLL3 gene consists of 8 exons spanning 9.5 kBp located on chromosome 19q13. Alternate splicing within the last exon gives rise to two processed transcripts, one of 2389 bases (Accession No. NM_016941) and one of 2052 bases (Accession No. NM_203486). The former transcript encodes a 618 amino acid protein (Accession No. NP_058637; SEQ ID NO:29), whereas the latter encodes a 587 amino acid protein (Accession No. NP_982353; SEQ ID NO:30), In certain cancers, such as SCLC, DLL3 has been found to be expressed on the cell surface, making it a highly tumor-selective cell surface protein (Saunders et al. (2015) Sci Transl Med; 7:302ra136.).

Engineered immune cells have been shown to possess desired qualities in therapeutic treatments, particularly in oncology. Two main types of engineered immune cells are those that contain chimeric antigen receptors (termed "CARs" or "CAR-Ts") and T-cell receptors ("TCRs"). These engineered cells are engineered to endow them with antigen specificity while retaining or enhancing their ability to recognize and kill a target cell. Chimeric antigen receptors may comprise, for example, (i) an antigen-specific component ("antigen binding molecule"), (ii) one or more costimulatory domains, and (iii) one or more activating domains. Each domain may be heterogeneous, that is, comprised of sequences derived from different protein chains. Chimeric antigen receptor-expressing immune cells (such as T cells) may be used in various therapies, including cancer therapies. It will be appreciated that costimulating polypeptides as defined herein may be used to enhance the activation of CAR-expressing cells against target antigens, and therefore increase the potency of adoptive immunotherapy.

T cells can be engineered to possess specificity to one or more desired targets. For example, T cells can be transduced with DNA or other genetic material encoding an antigen binding molecule, such as one or more single chain variable fragment ("scFv") of an antibody, in conjunction with one or more signaling molecules, and/or one or more activating domains, such as CD3 zeta.

In addition to the CAR-T cells' ability to recognize and destroy the targeted cells, successful T cell therapy benefits from the CAR-T cells' ability to persist and maintain the ability to proliferate in response to antigen.

A need exists to identify novel and improved therapies for treating DLL3 related diseases and disorders.

SUMMARY OF THE INVENTION

The invention relates to engineered immune cells (such as CARs or TCRs), antigen binding molecules (including but not limited to, antibodies, scFvs, heavy and/or light chains, and CDRs of these antigen binding molecules) with specificity to DLL3.

Chimeric antigen receptors of the invention typically comprise: (i) a DLL3 specific antigen binding molecule, (ii) one or more costimulatory domain, and (iii) one or more activating domain. It will be appreciated that each domain may be heterogeneous, thus comprised of sequences derived from different protein chains.

In some embodiments, the invention relates to a chimeric antigen receptor comprising an antigen binding molecule that specifically binds to DLL3, wherein the antigen binding molecule comprises at least one of: (a) a variable heavy chain CDR1 comprising an amino acid sequence differing from that of SEQ ID NO:42 or SEQ ID NO:52 or SEQ ID NO:62 by not more than 3, 2, 1, or 0 amino acid residues; (b) a variable heavy chain CDR2 comprising an amino acid sequence differing from that of SEQ ID NO:43 or SEQ ID NO:53 or SEQ ID NO:63 by not more than 3, 2, 1, or 0 amino acid residues; (c) a variable heavy chain CDR3 comprising an amino acid sequence differing from that of 44 or SEQ ID NO:54 or SEQ ID NO:64 by not more than 3, 2, 1, or 0 amino acid residues; (d) a variable light chain CDR1 comprising an amino acid sequence differing from that of SEQ ID NO:47 or SEQ ID NO:57 or SEQ ID NO:67 by not more than 3, 2, 1, or 0 amino acid residues; (e) a variable light chain CDR2 comprising an amino acid sequence differing from that of SEQ ID NO:48 or SEQ ID NO:58 or SEQ ID NO:68 by not more than 3, 2, 1, or 0 amino acid residues; (f) a variable light chain CDR3 comprising an amino acid sequence differing from that of SEQ ID:49 or SEQ ID NO:59 or SEQ ID NO:69 by not more than 3, 2, 1, or 0 amino acid residues.

In other embodiments, the chimeric antigen receptor further comprises at least one costimulatory domain. In further embodiments, the chimeric antigen receptor further comprises at least one activating domain.

In certain embodiments the costimulatory domain is a signaling region of CD28, CD28T, CD8, OX-40, 4-1BB/CD137, CD2, CD7, CD27, CD30, CD40, Programmed Death-1 (PD-1), inducible T cell costimulator (ICOS), lymphocyte function-associated antigen-1 (LFA-1, CDl-la/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In some embodiments, the costimulatory domain is derived from 4-1BB. In other embodiments, the costimulatory domain is derived from CD28 or CD28T. In other embodiments, the costimulatory domain is derived from CD8. In other embodiments, the costimulatory domain is derived from OX40. See also Hombach et al., Oncoimmunology. 2012 Jul. 1; 1(4): 458-466. In still other embodiments, the costimulatory domain comprises ICOS as described in Guedan et al., Aug. 14, 2014; Blood: 124 (7) and Shen et al., Journal of Hematology & Oncology (2013) 6:33. In still other embodiments, the costimulatory domain comprises CD27 as described in Song et al., Oncoimmunology. 2012 Jul. 1; 1(4): 547-549.

In certain embodiments, the CD28 costimulatory domain comprises SEQ ID NO:2, SEQ ID NO:4, SEQ ID NO:6, or SEQ ID NO:8. In additional embodiments, the CD8 costimulatory domain comprises SEQ ID NO:14. In additional embodiments, the 4-1BB costimulatory domain comprises SEQ ID NO:16. In additional embodiments, the costimulatory domain is a CD28 costimulatory domain which comprises a sequence that differs at no more than 10, 9, 8, 7, 6, 5, 4, 3, 2, 1, or 0 amino acid residues from the sequence of SEQ ID NO: 2, SEQ ID NO: 4. In further embodiments, the activating domain comprises CD3, CD3 zeta, or CD3 zeta having the sequence set forth in SEQ ID NO: 10. In additional embodiments, the CD3 zeta comprises a sequence that differs at no more than 10, 9, 8, 7, 6, 5, 4, 3, 2, 1, or 0 amino acid residues from the sequence of SEQ ID NO: 10.

In other embodiments, the invention relates to a chimeric antigen receptor wherein the costimulatory domain comprises SEQ ID NO:2 and the activating domain comprises SEQ ID NO:10.

The invention further relates to polynucleotides encoding the chimeric antigen receptors, and vectors comprising the polynucleotides. The vector can be, for example, a retroviral vector, a DNA vector, a plasmid, a RNA vector, an adenoviral vector, an adenovirus associated vector, a lentiviral vector, or any combination thereof. The invention further relates to immune cells comprising the vectors. In some embodiments, the lentiviral vector is a pGAR vector.

Exemplary immune cells include, but are not limited to T cells, tumor infiltrating lymphocytes (TILs), NK cells, TCR-expressing cells, dendritic cells, or NK-T cells. The T cells can be autologous, allogeneic, or heterologous. In other embodiments, the invention relates to pharmaceutical compositions comprising the immune cells of described herein.

In certain embodiments, the invention relates to antigen binding molecules (and chimeric antigen receptors comprising these molecules) comprising at least one of:
(a) a VH region differing from the amino acid sequence of the VH region of 1H2.1 by no more than 10, 9, 8, 7, 6, 5, 4, 3, 2, 1, or 0 amino acid residues and a VL region differing from the amino acid sequence of the VL region of 1H2.1 by no more than 10, 9, 8, 7, 6, 5, 4, 3, 2, 1, or 0 amino acid residues;
(b) a VH region differing from the amino acid sequence of the VH region of 8D2 by no more than 10, 9, 8, 7, 6, 5, 4, 3, 2, 1, or 0 amino acid residues and a VL region differing from the amino acid sequence of the VL region of 8D2 by no more than 10, 9, 8, 7, 6, 5, 4, 3, 2, 1, or 0 amino acid residues;
(c) a VH region differing from the amino acid sequence of the VH region of 6B2 by no more than 10, 9, 8, 7, 6, 5, 4, 3, 2, 1, or 0 amino acid residues and a VL region differing from the amino acid sequence of the VL region of 6B2 by no more than 10, 9, 8, 7, 6, 5, 4, 3, 2, 1, or 0 amino acid residues;
and wherein the VH and VL region or regions are linked by at least one linker.

In other embodiments, the invention relates to antigen binding molecules (and chimeric antigen receptors comprising these molecules) wherein the linker comprises at least one of the scFv G4S linker and the scFv Whitlow linker.

In other embodiments, the invention relates to vectors encoding the polypeptides of the invention and to immune cells comprising these polypeptides. Preferred immune cells include T cells, tumor infiltrating lymphocytes (TILs), NK cells, TCR-expressing cells, dendritic cells, or NK-T cells. The T cells may be autologous, allogeneic, or heterologous.

In other embodiments, the invention relates to isolated polynucleotides encoding a chimeric antigen receptor (CAR) or T cell receptor (TCR) comprising an antigen binding molecule that specifically binds to DLL3, wherein the antigen binding molecule comprises a variable heavy (VH) chain CDR3 comprising an amino acid sequence of SEQ ID NO:44 or SEQ ID NO:54 or SEQ ID NO:64. The polynucleotides may further comprise an activating domain. In preferred embodiments, the activating domain is CD3, more preferably CD3 zeta, more preferably the amino acid sequence set forth in SEQ ID NO:9.

In other embodiments, the invention includes a costimulatory domain, such as CD28, CD28T, OX40, CD8, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-ld, ITGAE, CD103, ITGAL, CD1-la, LFA-1, ITGAM, CD1-1b, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. Preferred costimulatory domains are recited hereinbelow.

In further embodiments, the invention relates to isolated polynucleotides encoding a chimeric antigen receptor (CAR) or T cell receptor (TCR), wherein said CAR or TCR comprises an antigen binding molecule that specifically binds to DLL3, and wherein the antigen binding molecule comprises a variable light ($V_L$) chain CDR3 comprising an amino acid sequence selected from SEQ ID NO:47, SEQ ID NO:57 and SEQ ID NO:67. The polynucleotide can further comprise an activating domain. The polynucleotide can further comprise a costimulatory domain.

In other embodiments, the invention relates to isolated polynucleotides encoding a chimeric antigen receptor (CAR) or T cell receptor (TCR) comprising an antigen binding molecule that specifically binds to DLL3, wherein the antigen binding molecule heavy chain comprises CDR1 (SEQ ID NO:42), CDR2 (SEQ ID NO:43), and CDR3 (SEQ ID NO:44) and the antigen binding molecule light chain comprises CDR1 (SEQ ID NO:47), CDR2 (SEQ ID NO:48), and CDR3 (SEQ ID NO:49).

In other embodiments, the invention relates to isolated polynucleotides encoding a chimeric antigen receptor (CAR) or T cell receptor (TCR) comprising an antigen binding molecule that specifically binds to DLL3, wherein the antigen binding molecule heavy chain comprises CDR1 (SEQ ID NO:52), CDR2 (SEQ ID NO:53), and CDR3 (SEQ ID NO:54) and the antigen binding molecule light chain comprises CDR1 (SEQ ID NO:57), CDR2 (SEQ ID NO:58), and CDR3 (SEQ ID NO:59).

In other embodiments, the invention relates to isolated polynucleotides encoding a chimeric antigen receptor (CAR) or T cell receptor (TCR) comprising an antigen binding molecule that specifically binds to DLL3, wherein the antigen binding molecule heavy chain comprises CDR1 (SEQ ID NO:62), CDR2 (SEQ ID NO:63), and CDR3 (SEQ ID NO:64) and the antigen binding molecule light chain comprises CDR1 (SEQ ID NO:67), CDR2 (SEQ ID NO:68), and CDR3 (SEQ ID NO:69).

The invention further relates to antigen binding molecules to DLL3 comprising at least one variable heavy chain CDR3 or variable light chain CDR3 sequence as set forth herein. The invention further relates to antigen binding molecules to DLL3 comprising at least one variable heavy chain CDR1, CDR2, and CDR3 sequences as described herein. The invention further relates to antigen binding molecules to DLL3 comprising at least one variable light chain CDR1, CDR2, and CDR3 sequences as described herein. The invention further relates to antigen binding molecules to DLL3 comprising both variable heavy chain CDR1, CDR2, CDR3, and variable light chain CDR1, CDR2, and CDR3 sequences as described herein.

Additional heavy and light chain variable domains and CDR polynuelcotide and amino acid sequences suitable for use in DLL3-binding molecules according to the present invention are found in U.S. Provisional Application No. 62/199,944, filed on Jul. 31, 2015.

The invention further relates to methods of treating a disease or disorder in a subject in need thereof comprising administering to the subject the antigen binding molecules, the CARs, TCRs, polynucleotides, vectors, cells, or compositions according to the invention. Suitable diseases for treatment include, but are not limited to, adrenal, liver, kidney, bladder, breast, gastric, ovarian, cervical, uterine, esophageal, colorectal, prostate (e.g., prostate adenocarcinoma), pancreatic, lung (both small cell and non-small cell), thyroid, carcinomas, sarcomas, glioblastomas, head and neck tumors, large cell neuroendocrine carcinoma (LCNEC), medullary thyroid cancer, glioblastoma, neuroendocrine prostate cancer, (NEPC), high-grade gastroenteropancreatic cancer (GEP) and malignant melanoma.

BRIEF DESCRIPTION OF THE FIGURES

FIG. 2A-C, depicts cytolytic activity of lentivirus-transduced CAR T cells from healthy donors.

DETAILED DESCRIPTION OF THE INVENTION

Figure 1A:
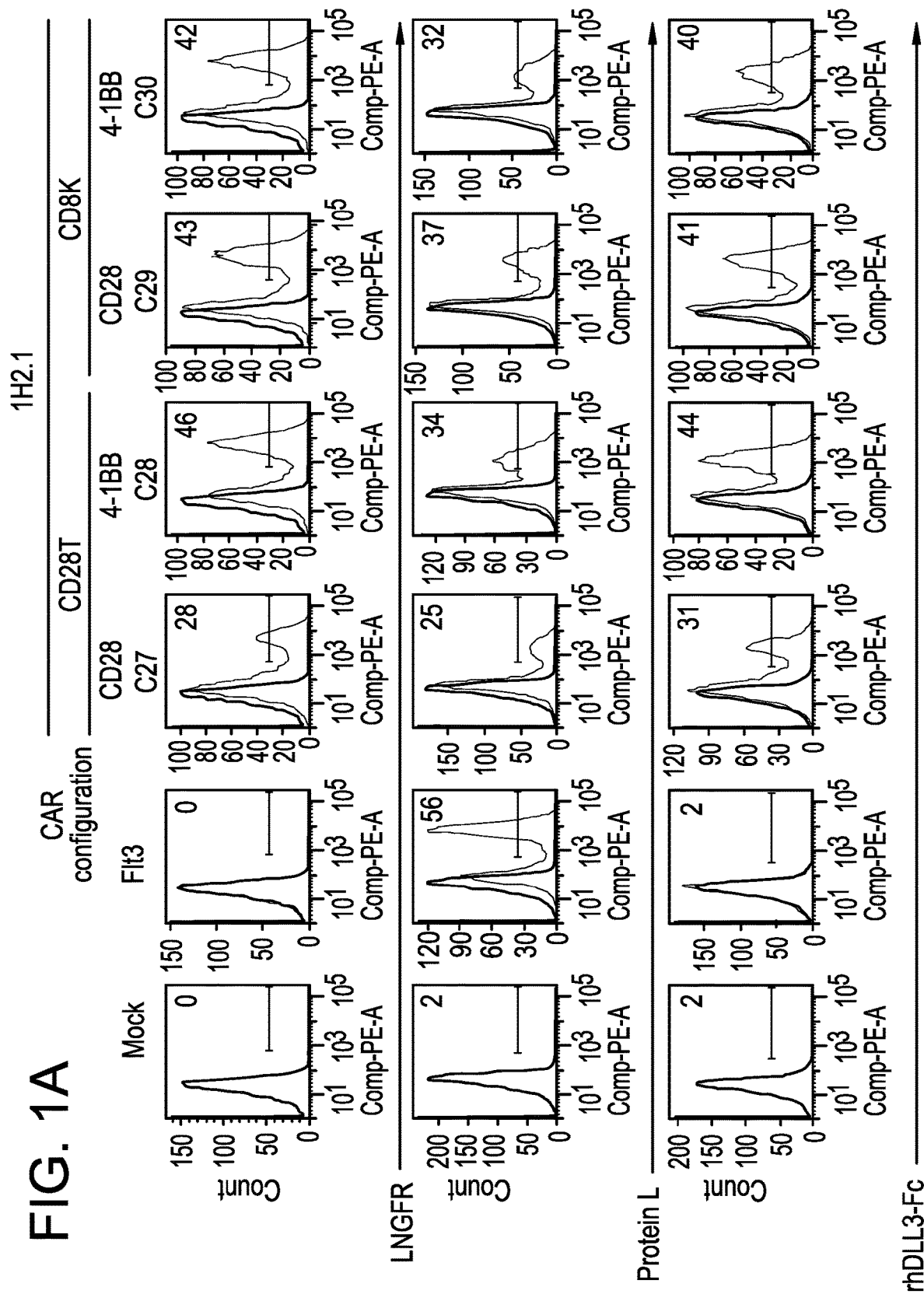
FIG. 1A-B, depicts expression of DLL3 CARs in T cells from a healthy donor.

It will be appreciated that chimeric antigen receptors (CARs or CAR-Ts) and T cell receptors (TCRs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

CARs can be engineered to bind to an antigen (such as a cell-surface antigen) by incorporating an antigen binding molecule that interacts with that targeted antigen. Preferably, the antigen binding molecule is an antibody fragment thereof, and more preferably one or more single chain antibody fragment ("scFv"). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are preferred for use in chimeric antigen receptors because they can be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

Costimulatory Domains. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33

(2011), and Gross et al., Annu. Rev. Pharmacol. Toxicol. 56:59-83 (2016). For example, CD28 is a costimulatory protein found naturally on T-cells. The complete native amino acid sequence of CD28 is described in NCBI Reference Sequence: NP_006130.1. The complete native CD28 nucleic acid sequence is described in NCBI Reference Sequence: NM_006139.1.

Certain CD28 domains have been used in chimeric antigen receptors. In accordance with the invention, it has now been found that a novel CD28 extracellular domain, termed "CD28T", unexpectedly provides certain benefits when utilized in a CAR construct.

The nucleotide sequence of the CD28T molecule, including the extracellular CD28T domain, and the CD28 transmembrane and intracellular domains is set forth in SEQ ID NO:1:

CTTGATAATGAAAAGTCAAACGGAACAATCATTCACGTGAAGGGCAAGCAC

CTCTGTCCGTCACCCTTGTTCCCTGGTCCATCCAAGCCATTCTGGGTGTTG

GTCGTAGTGGGTGGAGTCCTCGCTTGTTACTCTCTGCTCGTCACCGTGGCT

TTTATAATCTTCTGGGTTAGATCCAAAAGAAGCCGCCTGCTCCATAGCGAT

TACATGAATATGACTCCACGCCGCCCTGGCCCCACAAGGAAACACTACCAG

CCTTACGCACCACCTAGAGATTTCGCTGCCTATCGGAGC

The corresponding amino acid sequence is set forth in SEQ ID NO:2:

LDNEKSNGTI IHVKGKHLCPSPLFPGPSKPFWVLVVVGGVLACYSLLVTVA

FIIFWVRSK RSRLLHSDYM NMTPRRPGPT RKHYQPYAPP RDFAAYRS

The nucleotide sequence of the extracellular portion of CD28T is set forth in SEQ ID NO:3:

CTTGATAATGAAAAGTCAAACGGAACAATCATTCACGTGAAGGGCAAGCAC

CTCTGTCCGTCACCCTTGTTCCCTGGTCCATCCAAGCCA

The corresponding amino acid sequence of the CD28T extracellular domain is set forth in

SEQ ID NO: 4:
LDNEKSNGTI IHVKGKHLCP SPLFPGPSKP

The nucleotide sequence of the CD28 transmembrane domain is set forth in SEQ ID NO:5):

TTCTGGGTGTTGGTCGTAGTGGGTGGAGTCCTCGCTTGTTACTCTCTGCTC

GTCACCGTGGCTTTTATAATCTTCTGGGTT

The amino acid sequence of the CD28 transmembrane domain is set forth in

SEQ ID NO: 6:
FWVLVVVGGV LACYSLLVTV AFIIFWV

The nucleotide sequence of the CD28 intracellular signaling domain is set forth in SEQ ID NO:7:

AGATCCAAAAGAAGCCGCCTGCTCCATAGCGATTACATGAATATGACTCCA

CGCCGCCCTGGCCCCACAAGGAAACACTACCAGCCTTACGCACCACCTAGA

GATTTCGCTGCCTATCGGAGC

The amino acid sequence of the CD28 intracellular signaling is set forth in

SEQ ID NO: 8:
RSKRSRLLHSDYNINMTPRRPGPTRKHYQPYAPPRDFAAYRS

Additional CD28 sequences suitable for use in the invention include the CD28 nucleotide sequence set forth in SEQ ID NO:11:

ATTGAGGTGATGTATCCACCGCCTTACCTGGATAACGAAAAGAGTAACGGT

ACCATCATTCACGTGAAAGGTAAACACCTGTGTCCTTCTCCCCTCTTCCCC

GGGCCATCAAAGCCC

The corresponding amino acid sequence is set forth in SEQ ID NO:12:

IEVMYPPPYLD-NEKSNGTIIHVKGKHLCPSPLFPGPSKP

Other suitable extracellular or transmembrane sequences can be derived from CD8. The nucleotide sequence of a suitable CD8 extracellular and transmembrane domain is set forth in SEQ ID NO:13:

GCTGCAGCATTGAGCAACTCAATAATGTATTTTAGTCACTTTGTACCAGTG

TTCTTGCCGGCTAAGCCTACTACCACACCCGCTCCACGGCCACCTACCCCA

GCTCCTACCATCGCTTCACAGCCTCTGTCCCTGCGCCCAGAGGCTTGCCGA

CCGGCCGCAGGGGGCGCTGTTCATACCAGAGGACTGGATTTCGCCTGCGAT

ATCTATATCTGGGCACCCCTGGCCGGAACCTGCGGCGTACTCCTGCTGTCC

CTGGTCATCACGCTCTATTGTAATCACAGGAAC

The corresponding amino acid sequence is set forth in SEQ ID NO:14:

AAALSNSIMYFSHFVPVFLPAKPTTTPAPRPPTPAPTIASQPLSLRPEACR

PAAGGAVHTRGLDFACDIYIWAPLAGTCGVLLLSLVITLYCNHRN

Other suitable intracellular signaling sequences can be derived from 41-BB. The nucleotide sequence of a suitable 41-BB intracellular signaling domain is set forth in SEQ ID NO:15:

CGCTTTTCCGTCGTTAAGCGGGGAGAAAAAAGCTGCTGTACATTTTCAA

ACAGCCGTTTATGAGGCCGGTCCAAACGACTCAGGAAGAGGACGGCTGCT

CCTGCCGCTTTCCTGAGGAGGAGGAGGGCGGGTGCGAACTG

The corresponding amino acid sequence is set forth in SEQ ID NO:16:

RFSVVKRGRKKLLYIFKQPFMRPVQTTQEEDGCSCRFPEEEEGGCEL

Suitable costimulatory domains within the scope of the invention can be derived from, among other sources, CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CDla/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof.

Activating Domains.

CD3 is an element of the T cell receptor on native T cells, and has been shown to be an important intracellular activating element in CARs. In a preferred embodiment, the CD3 is CD3 zeta, the nucleotide sequence of which is set forth in SEQ ID NO:9:

AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG

The corresponding amino acid of intracellular CD3 zeta is set forth in SEQ ID NO:10:

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

Domain Orientation

Structurally, it will appreciated that these domains correspond to locations relative to the immune cell. Thus, these domains can be part of the (i) "hinge" or extracellular (EC) domain (EC), (ii) the transmembrane (TM) domain, and/or (iii) the intracellular (cytoplasmic) domain (IC). The intracellular component frequently comprises in part a member of the CD3 family, preferably CD3 zeta, which is capable of activating the T cell upon binding of the antigen binding molecule to its target. In one embodiment, the hinge domain is typically comprised of at least one costimulatory domain as defined herein.

It will also be appreciated that the hinge region may also contain some or all of a member of the immunoglobulin family such as IgG1, IgG2, IgG3, IgG4, IgA, IgD, IgE, IgM, or fragment thereof.

Exemplary CAR constructs in accordance with the invention are set forth in Table 1.

TABLE 1

| Construct Name | scFv | Costimulatory Domain | Activating Domain |
| --- | --- | --- | --- |
| 1H2.1 CD28T | 1H2.1 | CD28T | CD3 zeta |
| 1H2.1 4-1BB | 1H2.1 | 4-1BB | CD3 zeta |
| 8D2 CD28T | 8D2 | CD28T | CD3 zeta |
| 8D2 4-1BB | 8D2 | 4-1BB | CD3 zeta |
| 6B2 CD28T | 6B2 | CD28T | CD3 zeta |
| 6B2 4-1BB | 6B2 | 4-1BB | CD3 zeta |

Domains Relative to the Cell

It will be appreciated that relative to the cell bearing the receptor, the engineered T cells of the invention comprise an antigen binding molecule (such as an scFv), an extracellular domain (which may comprise a "hinge" domain), a transmembrane domain, and an intracellular domain. The intracellular domain comprises at least in part an activating domain, preferably comprised of a CD3 family member such as CD3 zeta, CD3 epsilon, CD3 gamma, or portions thereof. It will further be appreciated that the antigen binding molecule (e.g., one or more scFvs) is engineered such that it is located in the extracellular portion of the molecule/construct, such that it is capable of recognizing and binding to its target or targets.

Extracellular Domain. The extracellular domain is beneficial for signaling and for an efficient response of lymphocytes to an antigen. Extracellular domains of particular use in this invention may be derived from (i.e., comprise) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CDl-la/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDl lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The extracellular domain may be derived either from a natural or from a synthetic source.

As described herein, extracellular domains often comprise a hinge portion. This is a portion of the extracellular domain, sometimes referred to as a "spacer" region. A variety of hinges can be employed in accordance with the invention, including costimulatory molecules as discussed above, as well as immunoglobulin (Ig) sequences or other suitable molecules to achieve the desired special distance from the target cell. In some embodiments, the entire extracellular region comprises a hinge region. In some embodiments, the hinge region comprises CD28T, or the EC domain of CD28.

Transmembrane Domain. The CAR can be designed to comprise a transmembrane domain that is fused to the extracellular domain of the CAR. It can similarly be fused to the intracellular domain of the CAR. In one embodiment, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (i.e. comprise) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CDl-la/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDllc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

Optionally, short linkers may form linkages between any or some of the extracellular, transmembrane, and intracellular domains of the CAR.

In one embodiment, the transmembrane domain in the CAR of the invention is a CD8 transmembrane domain. In one embodiment, the CD8 transmembrane domain comprises the transmembrane portion of the nucleic acid sequence of SEQ ID NO:13. In another embodiment, the CD8 transmembrane domain comprises the nucleic acid sequence that encodes the transmembrane amino acid sequence contained within SEQ ID NO:14.

In certain embodiments, the transmembrane domain in the CAR of the invention is the CD28 transmembrane domain. In one embodiment, the CD28 transmembrane domain comprises the nucleic acid sequence of SEQ ID NO:5. In one embodiment, the CD28 transmembrane domain comprises the nucleic acid sequence that encodes the amino acid sequence of SEQ ID NO:6. In another embodiment, the CD28 transmembrane domain comprises the amino acid sequence of SEQ ID NO:6.

Intracellular (Cytoplasmic) Domain. The intracellular (cytoplasmic) domain of the engineered T cells of the invention can provide activation of at least one of the normal effector functions of the immune cell. Effector function of a T cell, for example, may be cytolytic activity or helper activity including the secretion of cytokines.

It will be appreciated that suitable intracellular molecules include (i.e., comprise), but are not limited to CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CDl-la/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDl ld, ITGAE, CD103, ITGAL, CDl la, LFA-1, ITGAM, CDl lb, ITGAX, CDllc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In a preferred embodiment, the cytoplasmic domain of the CAR can be designed to comprise the CD3 zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region.

The cytoplasmic signaling sequences within the cytoplasmic signaling portion of the CAR of the invention may be linked to each other in a random or specified order.

In one preferred embodiment, the cytoplasmic domain is designed to comprise the signaling domain of CD3 zeta and the signaling domain of CD28. In another embodiment, the cytoplasmic domain is designed to comprise the signaling domain of CD3 zeta and the signaling domain of 4-1BB, wherein the cytoplasmic CD28 comprises the nucleic acid sequence set forth in SEQ ID NO:15 and the amino acid sequence set forth in SEQ ID NO:16. In another embodiment, the cytoplasmic domain in the CAR of the invention is designed to comprise a portion of CD28 and CD3 zeta, wherein the cytoplasmic CD28 comprises the nucleic acid sequence set forth in SEQ ID NO:7 and the amino acid sequence set forth in SEQ ID NO:8. The CD3 zeta nucleic acid sequence is set forth in SEQ ID NO:9, and the amino acid sequence is set forth in SEQ ID NO:8.

It will be appreciated that one preferred orientation of the CARs in accordance with the invention comprises an antigen binding domain (such as scFv) in tandem with a costimulatory domain and an activating domain. The costimulatory domain can comprise one or more of an extracellular portion, a transmembrane portion, and an intracellular portion. It will be further appreciated that multiple costimulatory domains can be utilized in tandem.

In some embodiments, nucleic acids are provided comprising a promoter operably linked to a first polynucleotide encoding an antigen binding molecule, at least one costimulatory molecule, and an activating domain.

In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

Figure 7:
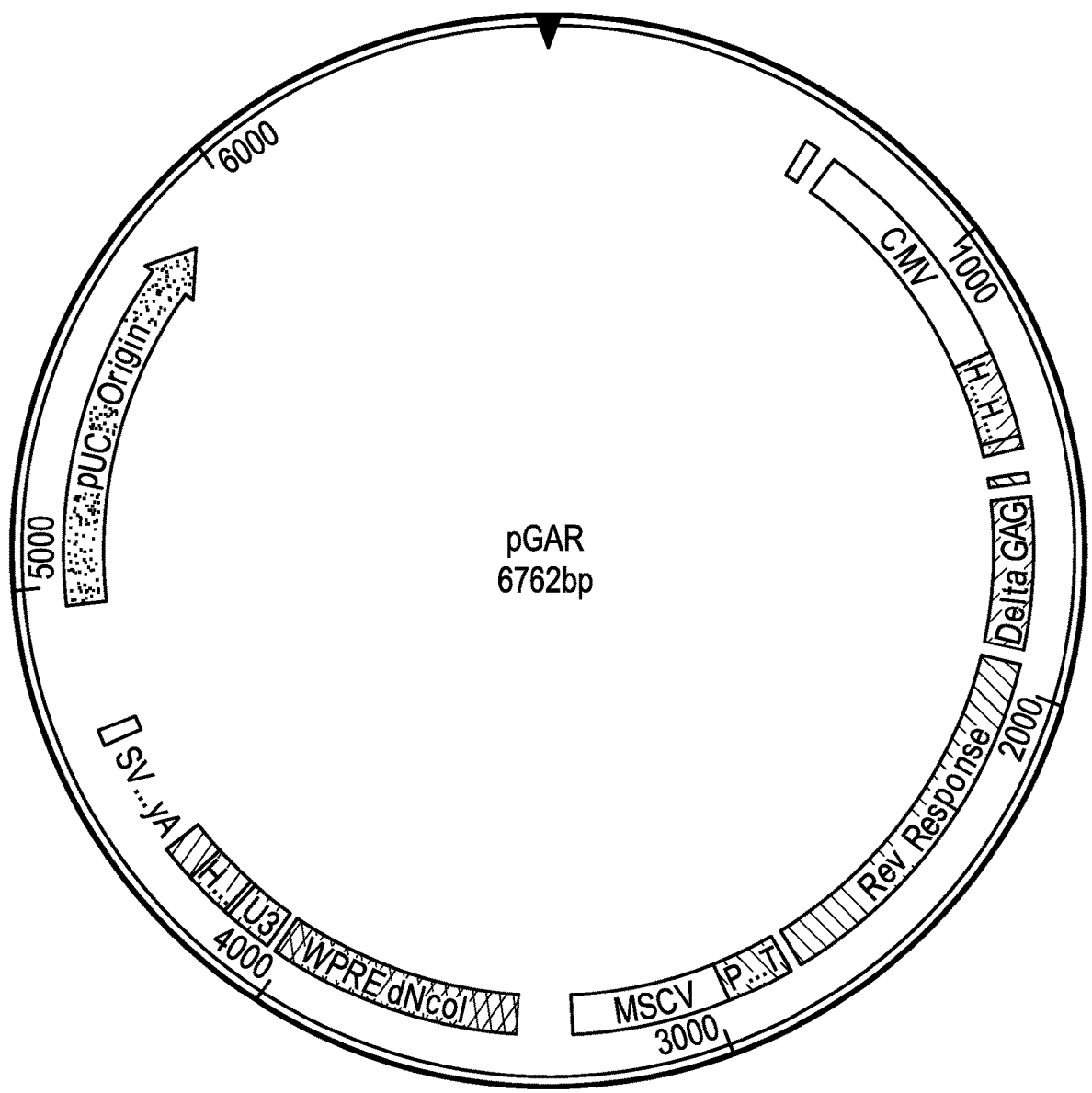
FIG. 7, depicts the pGAR vector map.

The invention further relates to isolated polynucleotides encoding the chimeric antigen receptors, and vectors comprising the polynucleotides. Any vector known in the art can be suitable for the present invention. In some embodiments, the vector is a viral vector. In some embodiments, the vector is a retroviral vector (such as pMSVG1), a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector (such as pGAR), or any combination thereof. The pGAR vector map is shown in FIG. 7. The pGAR sequence is as follows:

(SEQ ID NO: 70)
```
CTGACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGG
TTCACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCTCG
GTCTATTCTTTTGATTTATAAGGGATTTTGCCGATTTCGGCCTATTGGTTAAAAAATG
AGCTGATTTAACAAAAATTTAACGCGAATTTTAACAAAATATTAACGCTTACAATTT
GCCATTCGCCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATTGTAATAC
GACTCACTATAGGGCGACCCGGGGATGGCGCGCCAGTAATCAATTACGGGGTCATT
AGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAAC
TGCCCACTTGGCAGTACATCAAGTGTATCATATGCCAAGTACGCCCCCTATTGACGT
CAATGACGGTAAATGGCCCGCCTGGCATTATGCCCAGTACATGACCTTATGGGACTT
TCCTACTTGGCAGTACATCTACGTATTAGTCATCGCTATTACCATGCTGATGCGGTTT
TGGCAGTACATCAATGGGCGTGGATAGCGGTTTGACTCACGGGGATTTCCAAGTCTC
CACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTG
GGAGGTCTATATAAGCAGAGCTGGTTTAGTGAACCGGGGTCTCTCTGGTTAGACCAG
ATCTGAGCCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTCTGGTAACT
AGAGATCCCTCAGACCCTTTTAGTCAGTGTGGAAAATCTCTAGCAGTGGCGCCCGAA
CAGGGACTTGAAAGCGAAAGGGAAACCAGAGGAGCTCTCTCGACGCAGGACTCGG
CTTGCTGAAGCGCGCACGGCAAGAGGCGAGGGGCGGCGACTGGTGAGTACGCCAA
AAATTTTGACTAGCGGAGGCTAGAAGGAGAGAGATGGGTGCGAGAGCGTCAGTATT
AAGCGGGGGAGAATTAGATCGCGATGGGAAAAAATTCGGTTAAGGCCAGGGGGAA
```

-continued

```
AGAAAAAATATAAATTAAAACATATAGTATGGGCAAGCAGGGAGCTAGAACGATTC
GCAGTTAATCCTGGCCTGTTAGAAACATCAGAAGGCTGTAGACAAATACTGGGACA
GCTACAACCATCCCTTCAGACAGGATCAGAAGAACTTAGATCATTATATAATACAGT
AGCAACCCTCTATTGTGTGCATCAAAGGATAGAGATAAAAGACACCAAGGAAGCTT
TAGACAAGATAGAGGAAGAGCAAAACAAAAGTAAGACCACCGCACAGCAAGCCGC
CGCTGATCTTCAGACCTGGAGGAGGAGATATGAGGGACAATTGGAGAAGTGAATTA
TATAAATATAAAGTAGTAAAAATTGAACCATTAGGAGTAGCACCCACCAAGGCAAA
GAGAAGAGTGGTGCAGAGAGAAAAAAGAGCAGTGGGAATAGGAGCTTTGTTCCTTG
GGTTCTTGGGAGCAGCAGGAAGCACTATGGGCGCAGCGTCAATGACGCTGACGGTA
CAGGCCAGACAATTATTGTCTGGTATAGTGCAGCAGCAGAACAATTTGCTGAGGGCT
ATTGAGGCGCAACAGCATCTGTTGCAACTCACAGTCTGGGGCATCAAGCAGCTCCA
GGCAAGAATCCTGGCTGTGGAAAGATACCTAAAGGATCAACAGCTCCTGGGGATTT
GGGGTTGCTCTGGAAAACTCATTTGCACCACTGCTGTGCCTTGGAATGCTAGTTGGA
GTAATAAATCTCTGGAACAGATTTGGAATCACACGACCTGGATGGAGTGGGACAGA
GAAATTAACAATTACACAAGCTTAATACACTCCTTAATTGAAGAATCGCAAAACCA
GCAAGAAAAGAATGAACAAGAATTATTGGAATTAGATAAATGGGCAAGTTTGTGGA
ATTGGTTTAACATAACAAATTGGCTGTGGTATATAAAATTATTCATAATGATAGTAG
GAGGCTTGGTAGGTTTAAGAATAGTTTTTGCTGTACTTTCTATAGTGAATAGAGTTA
GGCAGGGATATTCACCATTATCGTTTCAGACCCACCTCCCAACCCCGAGGGGACCCG
ACAGGCCCGAAGGAATAGAAGAAGAAGGTGGAGAGAGAGACAGAGACAGATCCAT
TCGATTAGTGAACGGATCTCGACGGTATCGGTTAACTTTTAAAAGAAAAGGGGGGA
TTGGGGGGTACAGTGCAGGGGAAAGAATAGTAGACATAATAGCAACAGACATACA
AACTAAAGAATTACAAAAACAAATTACAAAATTCAAAATTTTATCGCGATCGCGGA
ATGAAAGACCCCACCTGTAGGTTTGGCAAGCTAGCTTAAGTAACGCCATTTTGCAAG
GCATGGAAAATACATAACTGAGAATAGAGAAGTTCAGATCAAGGTTAGGAACAGAG
AGACAGCAGAATATGGGCCAAACAGGATATCTGTGGTAAGCAGTTCCTGCCCCGGC
TCAGGGCCAAGAACAGATGGTCCCCAGATGCGGTCCCGCCCTCAGCAGTTTCTAGA
GAACCATCAGATGTTTCCAGGGTGCCCCAAGGACCTGAAAATGACCCTGTGCCTTAT
TTGAACTAACCAATCAGTTCGCTTCTCGCTTCTGTTCGCGCGCTTCTGCTCCCCGAGC
TCAATAAAAGAGCCCACAACCCCTCACTCGGCGCGCCAGTCCTTCGAAGTAGATCTT
TGTCGATCCTACCATCCACTCGACACACCCGCCAGCGGCCGCTGCCAAGCTTCCGAG
CTCTCGAATTAATTCACGGTACCCACCATGGCCTAGGGAGACTAGTCGAATCGATAT
CAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCG
TATGGCTTTCATTTTCTCCTCCTTGTATAAATCCTGGTTGCTGTCTCTTTATGAGGAGT
TGTGGCCCGTTGTCAGGCAACGTGGCGTGGTGTGCACTGTGTTTGCTGACGCAACCC
CCACTGGTTGGGGCATTGCCACCACCTGTCAGCTCCTTTCCGGGACTTTCGCTTTCCC
CCTCCCTATTGCCACGGCGGAACTCATCGCCGCCTGCCTTGCCCGCTGCTGGACAGG
GGCTCGGCTGTTGGGCACTGACAATTCCGTGGTGTTGTCGGGGAAGCTGACGTCCTT
TTCATGGCTGCTCGCCTGTGTTGCCACCTGGATTCTGCGCGGGACGTCCTTCTGCTAC
```

-continued

```
GTCCCTTCGGCCCTCAATCCAGCGGACCTTCCTTCCCGCGGCCTGCTGCCGGCTCTGC

GGCCTCTTCCGCGTCTTCGCCTTCGCCCTCAGACGAGTCGGATCTCCCTTTGGGCCGC

CTCCCCGCCTGGTTAATTAAAGTACCTTTAAGACCAATGACTTACAAGGCAGCTGTA

GATCTTAGCCACTTTTTAAAAGAAAAGGGGGGACTGGAAGGGCGAATTCACTCCCA

ACGAAGACAAGATCTGCTTTTTGCTTGTACTGGGTCTCTCTGGTTAGACCAGATCTG

AGCCTGGGAGCTCTCTGGCTAACTAGGGAACCCACTGCTTAAGCCTCAATAAAGCTT

GCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGGCATGCCAGACATGA

TAAGATACATTGATGAGTTTGGACAAACCACAACTAGAATGCAGTGAAAAAAATGC

TTTATTTGTGAAATTTGTGATGCTATTGCTTTATTTGTAACCATTATAAGCTGCAATA

AACAAGTTAACAACAACAATTGCATTCATTTTATGTTTCAGGTTCAGGGGGAGGTGT

GGGAGGTTTTTTGGCGCGCCATCGTCGAGGTTCCCTTTAGTGAGGGTTAATTGCGAG

CTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAACCT

GTCGTGCCAGCTGCATTAATGAATCGGCCAACGCGCGGGAGAGGCGGTTTGCGTA

TTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACAC

TAGAAGAACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGT

TTGCAAGCAGCAGATTACGCGCAGAAAAAAAGGATCTCAAGAAGATCCTTTGATCT

TTTCTACGGGGTCTGACGCTCAGTGGAACGAAAACTCACGTTAAGGGATTTTGGTCA

TGAGATTATCAAAAGGATCTTCACCTAGATCCTTTTAAATTAAAAATGAAGTTTTA

AATCAATCTAAAGTATATATGAGTAAACTTGGTCTGACAGTTACCAATGCTTAATCA

GTGAGGCACCTATCTCAGCGATCTGTCTATTTCGTTCATCCATAGTTGCCTGACTCCC

CGTCGTGTAGATAACTACGATACGGGAGGGCTTACCATCTGGCCCCAGTGCTGCAAT

GATACCGCGAGACCCACGCTCACCGGCTCCAGATTTATCAGCAATAAACCAGCCAG

CCGGAAGGGCCGAGCGCAGAAGTGGTCCTGCAACTTTATCCGCCTCCATCCAGTCTA

TTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATT

CAGCTCCGGTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCCGCAGTGTT
```

-continued

```
ATCACTCATGGTTATGGCAGCACTGCATAATTCTCTTACTGTCATGCCATCCGTAAG

ATGCTTTTCTGTGACTGGTGAGTACTCAACCAAGTCATTCTGAGAATAGTGTATGCG

GCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGA

TCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGC

CGCAAAAAGGGAATAAGGGCGACACGGAAATGTTGAATACTCATACTCTTCCTTTT

TCAATATTATTGAAGCATTTATCAGGGTTATTGTCTCATGAGCGGATACATATTTGA

ATGTATTTAGAAAAATAAACAAATAGGGGTTCCGCGCACATTTCCCCGAAAAGTGC

CAC
```

Suitable additional exemplary vectors include e.g., pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

In some embodiments, the engineered immune cell is a T cell, tumor infiltrating lymphocyte (TIL), NK cell, TCR-expressing cell, dendritic cell, or NK-T cell. In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, or polyplexes.

In some embodiments, chimeric antigen receptors are expressed in the engineered immune cells that comprise the nucleic acids of the present application. These chimeric antigen receptors of the present application may comprise, in some embodiments, (i) an antigen binding molecule (such as an scFv), (ii) a transmembrane region, and (iii) a T cell activation molecule or region.

Antigen Binding Molecules

Antigen binding molecules are within the scope of the invention.

An "antigen binding molecule" as used herein means any protein that binds a specified target antigen. In the instant application, the specified target antigen is the DLL3 protein or fragment thereof. Antigen binding molecules include, but are not limited to antibodies and binding parts thereof, such as immunologically functional fragments. Peptibodies (i.e., Fc fusion molecules comprising peptide binding domains) are another example of suitable antigen binding molecules.

In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to DLL3. In further embodiments, the antigen binding molecule is an antibody of fragment thereof, including one or more of the complementarity determining regions (CDRs) thereof. In further embodiments, the antigen binding molecule is a single chain variable fragment (scFv).

The term "immunologically functional fragment" (or "fragment") of an antigen binding molecule is a species of antigen binding molecule comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding molecules, including intact antibodies, for binding to a given epitope. In some embodiments, the fragments are neutralizing fragments. In some embodiments, the fragments can block or reduce the activity of DLL3. In one aspect, such a fragment will retain at least one CDR present in the full-length light or heavy chain, and in some embodiments will comprise a single heavy chain and/or light chain or portion thereof. These fragments can be produced by recombinant DNA techniques, or can be produced by enzymatic or chemical cleavage of antigen binding molecules, including intact antibodies.

Immunologically functional immunoglobulin fragments include, but are not limited to, scFv fragments, Fab fragments (Fab', F(ab')$_2$, and the like), one or more CDR, a diabody (heavy chain variable domain on the same polypeptide as a light chain variable domain, connected via a short peptide linker that is too short to permit pairing between the two domains on the same chain), domain antibodies, and single-chain antibodies. These fragments can be derived from any mammalian source, including but not limited to human, mouse, rat, camelid or rabbit. As will be appreciated by one of skill in the art, an antigen binding molecule can include non-protein components.

Variants of the antigen binding molecules are also within the scope of the invention, e.g., variable light and/or variable heavy chains that each have at least 70-80%, 80-85%, 85-90%, 90-95%, 95-97%, 97-99%, or above 99% identity to the amino acid sequences of the sequences described herein. In some instances, such molecules include at least one heavy chain and one light chain, whereas in other instances the variant forms contain two identical light chains and two identical heavy chains (or subparts thereof). A skilled artisan will be able to determine suitable variants of the antigen binding molecules as set forth herein using well-known techniques. In certain embodiments, one skilled in the art can identify suitable areas of the molecule that may be changed without destroying activity by targeting regions not believed to be important for activity.

In certain embodiments, the polypeptide structure of the antigen binding molecules is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding molecule comprises or consists of avimers.

In some embodiments, an antigen binding molecule to DLL3 is administered alone. In other embodiments, the antigen binding molecule to DLL3 is administered as part of a CAR, TCR, or other immune cell. In such immune cells, the antigen binding molecule to DLL3 can be under the control of the same promoter region, or a separate promoter. In certain embodiments, the genes encoding protein agents and/or an antigen binding molecule to DLL3 can be in separate vectors.

The invention further provides for pharmaceutical compositions comprising an antigen binding molecule to DLL3 together with a pharmaceutically acceptable diluent, carrier, solubilizer, emulsifier, preservative and/or adjuvant. In certain embodiments, pharmaceutical compositions will include more than one different antigen binding molecule to DLL3. In certain embodiments, pharmaceutical compositions will include more than one antigen binding molecule to DLL3 wherein the antigen binding molecules to DLL3 bind more than one epitope. In some embodiments, the various antigen binding molecules will not compete with one another for binding to DLL3.

In other embodiments, the pharmaceutical composition can be selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, a therapeutic composition can be in the form of a pyrogen-free, parenterally acceptable aqueous solution comprising a desired antigen binding molecule to DLL3, with or without additional therapeutic agents, in a pharmaceutically acceptable vehicle. In certain embodiments, a vehicle for parenteral injection is sterile distilled water in which an antigen binding molecule to DLL3, with or without at least one additional therapeutic agent, is formulated as a sterile, isotonic solution, properly preserved. In certain embodiments, the preparation can involve the formulation of the desired molecule with polymeric compounds (such as polylactic acid or polyglycolic acid), beads or liposomes that can provide for the controlled or sustained release of the product which can then be delivered via a depot injection. In certain embodiments, implantable drug delivery devices can be used to introduce the desired molecule.

In some embodiments, the antigen binding molecule is used as a diagnostic or validation tool. The antigen binding molecule can be used to assay the amount of DLL3 present in a sample and/or subject. In some embodiments, the diagnostic antigen binding molecule is not neutralizing. In some embodiments, the antigen binding molecules disclosed herein are used or provided in an assay kit and/or method for the detection of DLL3 in mammalian tissues or cells in order to screen/diagnose for a disease or disorder associated with changes in levels of DLL3. The kit can comprise an antigen binding molecule that binds DLL3, along with means for indicating the binding of the antigen binding molecule with DLL3, if present, and optionally DLL3 protein levels.

The antigen binding molecules will be further understood in view of the definitions and descriptions below.

An "Fc" region comprises two heavy chain fragments comprising the CH1 and CH2 domains of an antibody. The two heavy chain fragments are held together by two or more disulfide bonds and by hydrophobic interactions of the CH3 domains.

A "Fab fragment" comprises one light chain and the CH1 and variable regions of one heavy chain. The heavy chain of a Fab molecule cannot form a disulfide bond with another heavy chain molecule. A "Fab'" fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule. An "F(ab')$_2$ fragment" contains two light chains and two heavy chains containing a portion of the constant region between the CH1 and CH2 domains, such that an interchain disulfide bond is formed between the two heavy chains. An F(ab')$_2$ fragment thus is composed of two Fab' fragments that are held together by a disulfide bond between the two heavy chains.

The "Fv region" comprises the variable regions from both the heavy and light chains, but lacks the constant regions.

"Single chain variable fragment" ("scFv", also termed "single-chain antibody") refers to Fv molecules in which the heavy and light chain variable regions have been connected by a flexible linker to form a single polypeptide chain, which forms an antigen binding region. See PCT application WO88/01649 and U.S. Pat. Nos. 4,946,778 and 5,260,203, the disclosures of which are incorporated by reference in their entirety.

A "bivalent antigen binding molecule" comprises two antigen binding sites. In some instances, the two binding sites have the same antigen specificities. Bivalent antigen binding molecules can be bispecific. A "multispecific antigen binding molecule" is one that targets more than one antigen or epitope. A "bispecific," "dual-specific" or "bifunctional" antigen binding molecule is a hybrid antigen binding molecule or antibody, respectively, having two different antigen binding sites. The two binding sites of a bispecific antigen binding molecule will bind to two different epitopes, which can reside on the same or different protein targets.

An antigen binding molecule is said to "specifically bind" its target antigen when the dissociation constant ($K_d$) is $\sim 1 \times 10^{-7}$ M. The antigen binding molecule specifically binds antigen with "high affinity" when the $K_d$ is $1\text{-}5 \times 10^{-9}$ M, and with "very high affinity" when the $K_d$ is $1\text{-}5 \times 10^{-10}$ M. In one embodiment, the antigen binding molecule has a $K_d$ of $10^{-9}$ M. In one embodiment, the off-rate is $<1 \times 10^{-5}$. In other embodiments, the antigen binding molecules will bind to human DLL3 with a $K_d$ of between about $10^{-7}$ M and $10^{-13}$ M, and in yet another embodiment the antigen binding molecules will bind with a $K_d$ $1.0\text{-}5 \times 10^{-10}$.

An antigen binding molecule is said to be "selective" when it binds to one target more tightly than it binds to a second target.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding molecule as defined herein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be chimeric, that is, different portions of the antibody can be derived from two different antibodies as described further below. The antigen binding molecules, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates") and fragments thereof, respectively.

The variable regions typically exhibit the same general structure of relatively conserved framework regions (FR) joined by the 3 hypervariable regions (i.e., "CDRs"). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3. The assignment of amino acids to each domain is typically in accordance with the definitions of Kabat (Seqs of Proteins of Immunological Interest (NIH, Bethesda, MD (1987 and 1991)), or Chothia (J. Mol. Biol., 196:901-917 (1987); Chothia et al., Nature, 342:878-883 (1989)). Various methods of analysis can be employed to identify or approximate the CDR regions, including not only Kabat or Chothia, but also the AbM definition.

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, CH1, CH2, and CH3.

The $V_H$ domain is at the amino-terminus of the polypeptide, and the $C_H$ domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable region of an antibody typically determines specificity of a particular antibody for its target.

Variability is not evenly distributed throughout the variable domains of antibodies; it is concentrated in sub-domains of each of the heavy and light chain variable regions. These subdomains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDRH1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding site is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding site. H3, for example, can be as short as two amino acid residues or greater than 26 amino acids.

The term "neutralizing" refers to an antigen binding molecule, scFv, or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding molecule that prevents the protein to which it is bound from performing a biological function.

The term "target" or "antigen" refers to a molecule or a portion of a molecule capable of being bound by an antigen binding molecule. In certain embodiments, a target can have one or more epitopes.

The term "compete" when used in the context of antigen binding molecules that compete for the same epitope means competition between antigen binding molecules as determined by an assay in which the antigen binding molecule (e.g., antibody or immunologically functional fragment thereof) being tested prevents or inhibits (e.g., reduces) specific binding of a reference antigen binding molecule to an antigen. Numerous types of competitive binding assays can be used to determine if one antigen binding molecule competes with another, for example: solid phase direct or indirect radioimmunoassay (RIA), solid phase direct or indirect enzyme immunoassay (EIA), sandwich competition assay (Stahli et al., 1983, Methods in Enzymology 9:242-253); solid phase direct biotin-avidin EIA (Kirkland et al., 1986, J. Immunol. 137:3614-3619), solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82). The term "epitope" includes any determinant capable of being bound by an antigen binding molecule, such as an scFv, antibody, or immune cell of the invention. An epitope is a region of an antigen that is bound by an antigen binding molecule that targets that antigen, and when the antigen is a protein, includes specific amino acids that directly contact the antigen binding molecule.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used.

In accordance with the invention, on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

Methods of Treatment

Using adoptive immunotherapy, native T cells can be (i) removed from a patient, (ii) genetically engineered to express a chimeric antigen receptor (CAR) that binds to at least one tumor antigen (iii) expanded ex vivo into a larger population of engineered T cells, and (iv) reintroduced into the patient. See e.g., U.S. Pat. Nos. 7,741,465, and 6,319, 494, Eshhar et al. (Cancer Immunol, supra); Krause et al. (supra); Finney et al. (supra). After the engineered T cells are reintroduced into the patient, they mediate an immune response against cells expressing the tumor antigen. See e.g., Krause et al., J. Exp. Med., Volume 188, No. 4, 1998 (619-626). This immune response includes secretion of IL-2 and other cytokines by T cells, the clonal expansion of T cells recognizing the tumor antigen, and T cell-mediated specific killing of target-positive cells. See Hombach et al., Journal of Immun. 167: 6123-6131 (2001).

In some aspects, the invention therefore comprises a method for treating or preventing a condition associated with undesired and/or elevated DLL3 levels in a patient, comprising administering to a patient in need thereof an effective amount of at least one isolated antigen binding molecule, CAR, or TCR disclosed herein.

Methods are provided for treating diseases or disorders, including cancer. In some embodiments, the invention relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR), or a T cell receptor (TCR). In some embodiments, the target cell is a tumor cell. In some aspects, the invention comprises a method for treating or preventing a malignancy, said method comprising administering to a subject in need thereof an effective amount of at least one isolated antigen binding molecule described herein. In some aspects, the invention comprises a method for treating or preventing a malignancy, said method comprising administering to a subject in need thereof an effective amount of at least one immune cell, wherein the immune cell comprises at least one chimeric antigen receptor, T cell receptor, and/or isolated antigen binding molecule as described herein.

In some aspects, the invention comprises a pharmaceutical composition comprising at least one antigen binding molecule as described herein and a pharmaceutically acceptable excipient. In some embodiments, the pharmaceutical composition further comprises an additional active agent.

The antigen binding molecules, CARs, TCRs, immune cells, and the like of the invention can be used to treat myeloid diseases including but not limited to adrenal, liver, kidney, bladder, breast, gastric, ovarian, cervical, uterine, esophageal, colorectal, prostate (e.g., prostate adenocarcinoma), pancreatic, lung (both small cell and non-small cell), thyroid, carcinomas, sarcomas, glioblastomas, head and neck tumors, large cell neuroendocrine carcinoma (LCNEC), medullary thyroid cancer, glioblastoma, neuroendocrine prostate cancer, (NEPC), high-grade gastroenteropancreatic cancer (GEP) and malignant melanoma.

It will be appreciated that target doses for CAR+/CAR-T+/TCR+ cells can range from $1\times10^6$-$2\times10^{10}$ cells/kg, preferably $2\times10^6$ cells/kg, more preferably. It will be appreciated that doses above and below this range may be appropriate for certain subjects, and appropriate dose levels can be determined by the healthcare provider as needed. Additionally, multiple doses of cells can be provided in accordance with the invention.

Also provided are methods for reducing the size of a tumor in a subject, comprising administering to the subject an engineered cell of the present invention to the subject, wherein the cell comprises a chimeric antigen receptor, a T cell receptor, or a T cell receptor based chimeric antigen receptor comprising an antigen binding molecule binds to an antigen on the tumor. In some embodiments, the subject has a solid tumor, or a blood malignancy such as lymphoma or leukemia. In some embodiments, the engineered cell is delivered to a tumor bed. In some embodiments, the cancer is present in the bone marrow of the subject.

In some embodiments, the engineered cells are autologous T cells. In some embodiments, the engineered cells are allogeneic T cells. In some embodiments, the engineered cells are heterologous T cells. In some embodiments, the engineered cells of the present application are transfected or transduced in vivo. In other embodiments, the engineered cells are transfected or transduced ex vivo.

The methods can further comprise administering one or more chemotherapeutic agent. In certain embodiments, the chemotherapeutic agent is a lymphodepleting (preconditioning) chemotherapeutic. Beneficial preconditioning treatment regimens, along with correlative beneficial biomarkers are described in U.S. Provisional patent Applications 62/262, 143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). A preferred dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU;

androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxae), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In other embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab.

Additional therapeutic agents suitable for use in combination with the invention include, but are not limited to, ibrutinib)(Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab)(Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR-containing immune can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept)(ENBREL®), adalimumab (HUIMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In some aspects, the invention comprises an antigen binding molecule that binds to DLL3 with a $K_d$ that is smaller than 100 pM. In some embodiments, the antigen binding molecule binds with a $K_d$ that is smaller than 10 pM. In other embodiments, the antigen binding molecule binds with a $K_d$ that is less than 5 pM.

Methods of Making

A variety of known techniques can be utilized in making the polynucleotides, polypeptides, vectors, antigen binding molecules, immune cells, compositions, and the like according to the invention.

Prior to the in vitro manipulation or genetic modification of the immune cells described herein, the cells may be obtained from a subject. In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T cells can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing. The cells may be washed with PBS. As will be appreciated, a washing step may be used, such as by using a semiautomated flowthrough centrifuge—for example, the Cobe™ 2991 cell processor, the Baxter CytoMate™, or the like. After washing, the cells may be resuspended in a variety of biocompatible buffers, or other saline solution with or without buffer. In certain embodiments, the undesired components of the apheresis sample may be removed.

In certain embodiments, T cells are isolated from PBMCs by lysing the red blood cells and depleting the monocytes, for example, using centrifugation through a PERCOLL™ gradient. A specific subpopulation of T cells, such as CD28+, CD4+, CD8+, CD45RA+, and CD45RO+ T cells can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMCs may be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In certain embodiments, CD4+ T cells are further sorted into subpopulations. For example, CD4+ T helper cells can be sorted into naive, central memory, and effector cells by identifying cell populations that have cell surface antigens.

The immune cells, such as T cells, can be genetically modified following isolation using known methods, or the immune cells can be activated and expanded (or differentiated in the case of progenitors) in vitro prior to being genetically modified. In another embodiment, the immune cells, such as T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, for example, in U.S. Pat. Nos. 6,905,874; 6,867,041; 6,797,514; and PCT WO2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells.

In other embodiments, the T cells may be activated and stimulated to proliferate with feeder cells and appropriate antibodies and cytokines using methods such as those described in U.S. Pat. Nos. 6,040,177; 5,827,642; and WO2012129514, the contents of which are hereby incorporated by reference in their entirety.

Certain methods for making the constructs and engineered immune cells of the invention are described in PCT application PCT/US15/14520, the contents of which are hereby incorporated by reference in their entirety. Additional methods of making the constructs and cells can be found in U.S. provisional patent application No. 62/244,036 the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the invention provides a method of storing genetically engineered cells expressing CARs or TCRs which target a DLL3 protein. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

As used herein, "cryopreserve" refers to the preservation of cells by cooling to sub-zero temperatures, such as (typically) 77 Kelvin or −196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used in accordance with the invention include but are not limited to: dimethyl sulfoxide (DMSO) (Lovelock & Bishop, Nature (1959); 183: 1394-1395; Ashwood-Smith, Nature (1961); 190: 1204-1205), glycerol, polyvinylpyrrolidine (Rinfret, Ann. N.Y. Acad. Sci. (1960); 85: 576), and polyethylene glycol (Sloviter & Ravdin, Nature (1962); 196: 48). The preferred cooling rate is 1°-3° C./minute.

The term, "substantially pure," is used to indicate that a given component is present at a high level. The component is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration. At very high levels (e.g. at levels of more than 90%, of more than 95% or of more than 99%) the component can be regarded as being in "pure form." Biologically active substances of the present invention (including polypeptides, nucleic acid molecules, antigen binding molecules, moieties) can be provided in a form that is substantially free of one or more contaminants with which the substance might otherwise be associated. When a composition is substantially free of a given contaminant, the contaminant will be at a low level (e.g., at a level of less than 10%, less than 5%, or less than 1% on the dry weight/dry weight basis set out above).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells (for example, at least 1 $CD8^+$ central memory T cell and at least 1 $CD4^+$ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen (DLL3), lower numbers of cells, in the range of $10^6$/kilogram ($10^6$-$10^{11}$ per patient) may be administered. CAR treatments may be administered multiple times at dosages within these ranges. The cells may be autologous, allogeneic, or heterologous to the patient undergoing therapy.

The CAR expressing cell populations of the present invention may be administered either alone, or as a pharmaceutical composition in combination with diluents and/or with other components such as IL-2 or other cytokines or cell populations. Pharmaceutical compositions of the present invention may comprise a CAR or TCR expressing cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The pharmaceutical compositions (solutions, suspensions or the like), may include one or more of the following: sterile diluents such as water for injection, saline solution, preferably physiological saline, Ringer's solution, isotonic sodium chloride, fixed oils such as synthetic mono- or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

It will be understood that descriptions herein are exemplary and explanatory only and are not restrictive of the invention as claimed. In this application, the use of the singular includes the plural unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The term "DLL3 activity" includes any biological effect of DLL3. In certain embodiments, DLL3 activity includes the ability of DLL3 to interact or bind to a substrate or receptor.

The term "polynucleotide", "nucleotide", or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphoro-diselenoate, phosphoro-anilothioate, phoshoraniladate and phosphoroamidate.

The term "oligonucleotide" refers to a polynucleotide comprising 200 or fewer nucleotides. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences (signal peptides) and/or fusion partner sequences.

As used herein, "operably linked" means that the components to which the term is applied are in a relationship that allows them to carry out their inherent functions under suitable conditions.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" refers to a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous DNA by a cell. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197.

The term "transduction" refers to the process whereby foreign DNA is introduced into a cell via viral vector. See Jones et al., (1998). Genetics: principles and analysis. Boston: Jones & Bartlett Publ.

The terms "polypeptide" or "protein" refer to a macromolecule having the amino acid sequence of a protein, including deletions from, additions to, and/or substitutions of one or more amino acids of the native sequence. The terms "polypeptide" and "protein" specifically encompass DLL3 antigen binding molecules, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. Useful polypeptide fragments include immunologically functional fragments of antigen binding molecules. Useful fragments include but are not limited to one or more CDR regions, variable domains of a heavy and/or light chain, a portion of other portions of an antibody chain, and the like.

The term "isolated" means (i) free of at least some other proteins with which it would normally be found, (ii) is essentially free of other proteins from the same source, e.g., from the same species, (iii) separated from at least about 50 percent of polynucleotides, lipids, carbohydrates, or other materials with which it is associated in nature, (iv) operably associated (by covalent or noncovalent interaction) with a polypeptide with which it is not associated in nature, or (v) does not occur in nature.

A "variant" of a polypeptide (e.g., an antigen binding molecule, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm").

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

As used herein, the twenty conventional (e.g., naturally occurring) amino acids and their abbreviations follow conventional usage. See Immunology—A Synthesis (2nd Edition, Golub and Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, .gamma.-carboxyglutamate, epsilon-N,N,N-trimethyllysine, e-N-acetyllysine, O-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:

a) hydrophobic: norleucine, Met, Ala, Val, Leu, Ile;

b) neutral hydrophilic: Cys, Ser, Thr, Asn, Gln;

c) acidic: Asp, Glu;

d) basic: His, Lys, Arg;

e) residues that influence chain orientation: Gly, Pro; and f) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the antigen binding molecule, the costimulatory or activating domains of the engineered T cell, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). See Kyte et al., J. Mol. Biol., 157:105-131 (1982). It is known that certain amino acids can be substituted for other amino acids having a similar hydropathic index or score and still retain a similar biological activity. It is also understood in the art that the substitution of like amino acids can be made effectively on the basis of hydrophilicity, particularly where the biologically functional protein or peptide thereby created is intended for use in immunological embodiments, as in the present case. Exemplary amino acid substitutions are set forth in Table 2.

TABLE 2

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule can have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose.

The term "therapeutically effective amount" refers to the amount of a DLL3 antigen binding molecule determined to produce a therapeutic response in a mammal. Such therapeutically effective amounts are readily ascertained by one of ordinary skill in the art.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

The following sequences will further exemplify the invention.

CD28T DNA Extracellular, Transmembrane, Intracellular (SEQ ID NO: 1)
CTTGATAATGAAAAGTCAAACGGAACAATCATTCACGTGAAGGGCAAGC

ACCTCTGTCCGTCACCCTTGTTCCCTGGTCCATCCAAGCCATTCTGGGTGT

TGGTCGTAGTGGGTGGAGTCCTCGCTTGTTACTCTCTGCTCGTCACCGTGG

CTTTTATAATCTTCTGGGTTAGATCCAAAAGAAGCCGCCTGCTCCATAGCG

ATTACATGAATATGACTCCACGCCGCCCTGGCCCCACAAGGAAACACTAC

CAGCCTTACGCACCACCTAGAGATTTCGCTGCCTATCGGAGC

CD28T Extracellular, Transmembrane, Intracellular AA:

(SEQ ID NO: 2)
LDNEKSNGTI IHVKGKHLCP SPLFPGPSKP FWVLVVVGGV

LACYSLLVTV AFIIFWVRSK RSRLLHSDYM NMTPRRPGPT

RKHYQPYAPP RDFAAYRS

CD28T DNA—Extracellular (SEQ ID NO: 3)
CTTGATAATGAAAAGTCAAACGGAACAATCATTCACGTGAAGGGCAAGC

ACCTCTGTCCGTCACCCTTGTTCCCTGGTCCATCCAAGCCA

CD28T AA—Extracellular (SEQ ID NO: 4)
LDNEKSNGTI IHVKGKHLCP SPLFPGPSKP

CD28 DNA Transmembrane Domain (SEQ ID NO: 5)
TTCTGGGTGTTGGTCGTAGTGGGTGGAGTCCTCGCTTGTTACTCTCTGCTC

GTCACCGTGGCTTTTATAATCTTCTGGGTT

CD28 AA Transmembrane Domain:

(SEQ ID NO: 6)
FWVLVVVGGV LACYSLLVTV AFIIFWV

CD28 DNA Intracellular Domain:

(SEQ ID NO: 7)
AGATCCAAAAGAAGCCGCCTGCTCCATAGCGATTACATGAATATGACTCC
ACGCCGCCCTGGCCCCACAAGGAAACACTACCAGCCTTACGCACCACCTA
GAGATTTCGCTGCCTATCGGAGC

CD28 AA Intracellular Domain (SEQ ID NO: 8)
RSKRSRLLHSDYMNMTPRRPGPTRKHYQPYAPPRDFAAYRS

CD3 Zeta DNA (SEQ ID NO: 9)
AGGGTGAAGTTTTCCAGATCTGCAGATGCACCAGCGTATCAGCAGGGCCA
GAACCAACTGTATAACGAGCTCAACCTGGGACGCAGGGAAGAGTATGAC
GTTTTGGACAAGCGCAGAGGACGGGACCCTGAGATGGGTGGCAAACCAA
GACGAAAAAACCCCCAGGAGGGTCTCTATAATGAGCTGCAGAAGGATAA
GATGGCTGAAGCCTATTCTGAAATAGGCATGAAAGGAGAGCGGAGAAGG
GGAAAAGGGCACGACGGTTTGTACCAGGGACTCAGCACTGCTACGAAGG
ATACTTATGACGCTCTCCACATGCAAGCCCTGCCACCTAGG

CD3 Zeta AA (SEQ ID NO: 10)
RVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYD
ALHMQALPPR

CD28 DNA (SEQ ID NO: 11)
ATTGAGGTGATGTATCCACCGCCTTACCTGGATAACGAAAAGAGTAACGGT
ACCATCATTCACGTGAAAGGTAAACACCTGTGTCCTTCTCCCCTCTTCCCC
GGGCCATCAAAGCCC

CD28 AA (SEQ ID NO: 12)
IEVMYPPPYL DNEKSNGTII HVKGKHLCPS PLFPGPSKP

CD8 DNA Extracellular & Transmembrane Domain (SEQ ID NO: 13)
GCTGCAGCATTGAGCAACTCAATAATGTATTTTAGTCACTTTGTACCAGTG
TTCTTGCCGGCTAAGCCTACTACCACACCCGCTCCACGGCCACCTACCCCA
GCTCCTACCATCGCTTCACAGCCTCTGTCCCTGCGCCCAGAGGCTTGCCGA
CCGGCCGCAGGGGGCGCTGTTCATACCAGAGGACTGGATTTCGCCTGCGAT
ATCTATATCTGGGCACCCCTGGCCGGAACCTGCGGCGTACTCCTGCTGTCC
CTGGTCATCACGCTCTATTGTAATCACAGGAAC

CD8 AA Extracellular & Transmembrane Domain (SEQ ID NO: 14)
AAALSNSIMYFSHFVPVFLPAKPTTTPAPRPPTPAPTIASQPLSLRPEACR
PAAGGAVHTRGLDFACDIYIWAPLAGTCGVLLLSLVITLYCNHRN

4-1BB DNA Intracellular Domain (SEQ ID NO: 15)
CGCTTTTCCGTCGTTAAGCGGGGGAGAAAAAAGCTGCTGTACATTTTCAAA
CAGCCGTTTATGAGGCCGGTCCAAACGACTCAGGAAGAGGACGGCTGCTCC
TGCCGCTTTCCTGAGGAGGAGGAGGGCGGGTGCGAACTG

4-1BB AA Intracellular Domain (SEQ ID NO: 16)
RFSVVKRGRKKLLYIFKQPFMRPVQTTQEEDGCSCRFPEEEEGGCEL

Clone 1H2.1 HC DNA (SEQ ID NO: 40)
CAGGTGCAACTGCAGGAAAGCGGGCCCGGTCTGGTGAAGCCCTCAGAAACG
CTCTCCCTCACCTGTACAGTCTCTGGCGATTCAATCTCTTCATATTACTGG
ACGTGGATCAGGCAGCCTCCCGGCAAGGGACTGGAGTGGATCGGATATATC
TACTATAGTGGCACCACTAACTATAATCCTTCCCTGAAAAGCCGGGTGACA
ATCTCTGTTGACACCTCCAAGAGCCAGTTCAGCCTGAAACTCTCCAGTGTG
ACAGCCGCCGATACAGCCGTGTATTACTGTGCCTCTATCGCTGTGCGCGGG
TTCTTTTTTGATTATTGGGGCCAGGGGACACTGGTGACCGTTAGCAGC

Clone 1H2.1 HC AA-CDRs Underlined (SEQ ID NO: 41)
QVQLQESGPGLVKPSETLSLTCTVSGDSIS<u>SYYWT</u>WIRQPPGKGLEWIG<u>YI
YYSGTTNYNPSLKS</u>RVTISVDTSKSQFSLKLSSVTAADTAVYYCAS<u>IAVRG
FFFDY</u>WGQGTLVTVSS

Clone 1H2.1 HC AA CDR1:

(SEQ ID NO: 42)
SYYWT

Clone 1H2.1 HC AA CDR2:

(SEQ ID NO: 43)
YIYYSGTTNYNPSLKS

Clone 1H2.1 HC AA CDR3:

(SEQ ID NO: 44)
IAVRGFFFDY

Clone 1H2.1 LC DNA (SEQ ID NO: 45)
GAAATTGTACTGACCCAGTCCCCCGGCACGCTCTCTCTCTCCCCAGGGGAA
AGGGCAACCCTTAGCTGCCGGGCGAGCCAGAGCGTGAGTTCCTCCTACCTC -continued
GCGTGGTATCAGCAGAAGCCTGGACAGGCTCCCAGACTGCTGATTTACGGG
GCTTCTACGAGAGCCACCGGCATACCTGATAGGTTCTCTGGCTCCGGGTCT
GGGACCGACTTTACTCTTACAATCAGCAGACTTGAGCCTGAAGACTTCGCT
GTGTATTATTGTCAACAATACGGAACGTCCCCCCTTACCTTTGGTGGCGGG
ACAAAAGTGGAAATTAAGAGG Clone 1H2.1 LC AA (CDRs Underlined)

(SEQ ID NO: 46)
EIVLTQSPGTLSLSPGERATLSC<u>RASQSVSSSYLA</u>WYQQKPGQAPRLLIYG
<u>ASTRAT</u>GIPDRFSGSGSGTDFTLTISRLEPEDFAVYYC<u>QQYGTSPLT</u>FGGG
TKVEIKR

Clone 1H2.1 LC CDR1 AA:

(SEQ ID NO: 47)
RASQSVSSSYLA

Clone 1H2.1 LC CDR2 AA:

(SEQ ID NO: 48)
GASTRAT

Clone 1H2.1 LC CDR3 AA:

(SEQ ID NO: 49)
QQYGTSPLT

Clone 8D2 HC DNA (SEQ ID NO: 50)
CAGGTCCAGCTGGTGCAGTCTGGGGCAGAGGTGAAACGGCCGGGTGCAAG
CGTGAAGGTGTCCTGCAAAGCCTCTGGCTATACCTTTACTGGGTACTATA
TGCACTGGGTTCGGCAGGCGCCAGGACAGGGTCTTGAGTGGATGGGTTGG
ATTGATCCAAACTCTGGCGATACAAATTACGCACAGAAATTCCAGGGCCG
CGTGACGATGACTCGAGACACTTCCATATCCACCGCCTATATGGAAGTGA
ATAGACTCCGGTCTGACGACACTGCTGTCTATTACTGTGCAAGGGATCCC
AACCGGCGGAGTTGGTATTACGGAATGGATGTCTGGGCCCAGGGTACTAC
CGTCACGGTGTCTTCT Clone 8D2 HC AA (CDRs Underlined)

(SEQ ID NO: 51)
QVQLVQSGAEVKRPGASVKVSCKASGYTFT<u>GYYMH</u>WVRQAPGQGLEWMGW
<u>IDPNSGDTNYAQKFQG</u>RVTMTRDTSISTAYMEVNRLRSDDTAVYYCAR<u>DP
NRRSWYYGMDV</u>WAQGTTVTSS

Clone 8D2 HC AA CDR1:

(SEQ ID NO: 52)
GYYMH

Clone 8D2 HC AA CDR2:

(SEQ ID NO: 53)
WIDPNSGDTNYAQKFQG

Clone 8D2 HC AA CDR3:

(SEQ ID NO: 54)
DPNRRSWYYGMDV

Clone 8D2 LC DNA (SEQ ID NO: 55)
CAGGTCCAGCTGGTGCAGTCTGGGGCAGAGGTGAAACGGCCGGGTGCAAG
CGTGAAGGTGTCCTGCAAAGCCTCTGGCTATACCTTTACTGGGTACTATA
TGCACTGGGTTCGGCAGGCGCCAGGACAGGGTCTTGAGTGGATGGGTTGG
ATTGATCCAAACTCTGGCGATACAAATTACGCACAGAAATTCCAGGGCCG
CGTGACGATGACTCGAGACACTTCCATATCCACCGCCTATATGGAAGTGA
ATAGACTCCGGTCTGACGACACTGCTGTCTATTACTGTGCAAGGGATCCC
AACCGGCGGAGTTGGTATTACGGAATGGATGTCTGGGCCCAGGGTACTAC
CGTCACGGTGTCTTCTGGCGGCGGGGCTCAGGAGGAGGAGGCAGCGGTG
GAGGAGGCAGCGATATTCAGATGACACAAAGCCCTTCTAGTCTCTCCGCA
AGCGTTGGCGACCGCGTGACCATTACGTGTCAGGCTTCACAAGATATTCG
AAACTACCTGAACTGGTATCAGCAGAAGCCCGGCAAAGCACCTAAGCTGC
TGATTTATGACGCTAGCAACCTTGAGACTGGCGTCCCCTCCAGATTTTCC
GGCAGCGGCTCAGGCACCGACTTTACTTTTACCATCTCCACACTCCAGCC
AGAAGATATTGCAACGTATTACTGCCAACATTATGATAACCTGCCTTTGA
CCTTCGGAGGTGGCACCAAGGTAGAGATCAGAAGA Clone 8D2 LC AA (CDRs Underlined)

(SEQ ID NO: 56)
DIQMTQSPSSLSASVGDRVTITC<u>QASQDIRNYLN</u>WYQQKPGKAPKLLIYD
<u>ASNLET</u>GVPSRFSGSGSGTDFTFTISTLQPEDIATYYC<u>QHYDNLPLT</u>FGG
GTKVEIRR

Clone 8D2 LC AA CDR1:

(SEQ ID NO: 57)
QASQDIRNYLN

Clone 8D2 LC AA CDR2:

(SEQ ID NO: 58)
DASNLET

Clone 8D2 LHC AA CDR3:

(SEQ ID NO: 59)
QHYDNLPLTF

Clone 6B2 HC DNA (SEQ ID NO: 60)
CAAGTGCAGTTGGTGCAGTCTGGAGCTGAAGTGAAGAAACCAGGCGCTAG
CGTCAAAGTGAGCTGTAAGGCCTCAGGTTACACGTTTACTGGGTACTATA
TGCATTGGGTCAGGCAAGCCCCTGGCCAGGGCCTCGAGTGGATGGGCTGG
ATTAATCCTAACAGCGGGGACACAAGCTATGCCCAACGCTTCCTGGGCAG
AGTAACAATGACACGGGATACAAGTATTAACACCGTCCATATGGAACTCT
CTCGGCTCGGCTCAGATGATACCGCGGTTTATTACTGTGCTAGGGAGGAC
GACTCCTCTTGGTATGGCAGCTTCGATTATTGGGGGCAGGGAACCCTGGT
GACAGTCTCATCT Clone 6B2 HC AA (CDRs Underlined)

(SEQ ID NO: 61)
QVQLVQSGAEVKKPGASVKVSCKASGYTFTGYYMHWVRQAPGQGLEWMGW
INPNSGDTSYAQRFLGRVTMTRDTSINTVHMELSRLGSDDTAVYYCAREDD
DSSWYGSFDYWGQGTLVTVSS

Clone 6B2 HC AA CDR1:

(SEQ ID NO: 62)
GYYMH

Clone 6B2 HC AA CDR2:

(SEQ ID NO: 63)
WINPNSGDTSYAQRFLG

Clone 6B2 HC AA CDR3:

(SEQ ID NO: 64)
EDDSSWYGSFDY

Clone 6B2 LC DNA (SEQ ID NO: 65)
GATATACAGATGACTCAGAGTCCCTCAAGCTTGAGTGCCAGTGTAGGCGA
CCGGGTGACGATAACCTGTAGGGCTTCACAGGGAATCAGAAATTATCTGG
GTTGGTACCAGCAGAAGCCAGGAAAGGCACCTAAAAGACTTATTTACGCC
GCATCCTCCTTGCAGTCCGGCGTGCCATCAAAATTTTCTGGGAGCGGCTC
TGGAACCGAGTTCACCCTCACGATCTCCAGCCTCCAGCCCGAGGACTTTG
CCACCTACTATTGCCTGCAGCACGATAGTGATCTGCGAACTTTTGGGCAA
GGCACTAAAGTGGAAATTAAGAGA Clone 6B2 LC AA (CDRs Underlined)

(SEQ ID NO: 66)
DIQMTQSPSSLSASVGDRVTITCRASQGIRNYLGWYQQKPGKAPKRLIYA
ASSLQSGVPSKFSGSGSGTEFTLTISSLQPEDFATYYCLQHDSDLRTFGQ
GTKVEIKR

Clone 6B2 LC AA CDR1:

(SEQ ID NO: 67)
RASQGIRNYLG

Clone 6B2 LC AA CDR2:

(SEQ ID NO: 68)
AASSLQS

Clone 6B2 LC AA CDR3:

(SEQ ID NO: 69)
LQHDSDLRTF

Construct 1H2.1 4-1BB DNA (Signal Sequence in Bold)

(SEQ ID NO: 17)
**ATGGCACTCCCCGTAACTGCTCTGCTGCTGCCGTTGGCATTGCTCCTGCA
CGCCGCACGCCCG**CAGGTGCAACTGCAGGAAAGCGGGCCGGTCTGGTGA
AGCCCTCAGAAACGCTCTCCCTCACCTGTACAGTCTCTGGCGATTCAATC
TCTTCATATTACTGGACGTGGATCAGGCAGCCTCCCGGCAAGGGACTGGA
GTGGATCGGATATATCTACTATAGTGGCACCACTAACTATAATCCTTCCC
TGAAAAGCCGGGTGACAATCTCTGTTGACACCTCCAAGAGCCAGTTCAGC
CTGAAACTCTCCAGTGTGACAGCCGCCGATACAGCCGTGTATTACTGTGC
CTCTATCGCTGTGCGCGGGTTCTTTTTTGATTATTGGGGCCAGGGGACAC
TGGTGACCGTTAGCAGCGGGGAGGAGGGTCCGGTGGCGGCGGCAGCGGA
GGCGGGGGTTCAGAAATTGTACTGACCCAGTCCCCCGGCACGCTCTCTCT
CTCCCCAGGGGAAAGGGCAACCCTTAGCTGCCGGGCGAGCCAGAGCGTGA
GTTCCTCCTACCTCGCGTGGTATCAGCAGAAGCTGGACAGGCTCCCAGA
CTGCTGATTTACGGGCTTCTACGAGAGCCACCGGCATACCTGATAGGTT
CTCTGGCTCCGGGTCTGGGACCGACTTTACTCTTACAATCAGCAGACTTG
AGCCTGAAGACTTCGCTGTGTATTATTGTCAACAATACGGAACGTCCCCC
CTTACCTTTGGTGGCGGGACAAAAGTGGAAATTAAGAGGGCCGCTGCCCT
TGATAATGAAAGTCAAACGGAACAATCATTCACGTGAAGGGCAAGCACC
TCTGTCCGTCACCCTTGTTCCCTGGTCCATCCAAGCCATTCTGGGTGTTG
GTCGTAGTGGGTGGAGTCCTCGCTTGTTACTCTCTGCTCGTCACCGTGGC
TTTTATAATCTTCTGGGTTCGCTTTTCCGTCGTTAAGCGGGGGAGAAAAA
AGCTGCTGTACATTTTCAAACAGCCGTTTATGAGGCCGGTCCAAACGACT
CAGGAAGAAGACGGCTGCTCCTGCCGCTTTCCTGAGGAGGAGGAGGCGG
GTGCGAACTGAGGGTGAAGTTTTCCAGATCTGCAGATGCACCAGCGTATC
AGCAGGGCCAGAACCAACTGTATAACGAGCTCAACCTGGGACGCAGGGAA
GAGTATGACGTTTGGACAAGCGCAGAGGACGGGACCCTGAGATGGGTGG
CAAACCAAGACGAAAAACCCCCAGGAGGGTCTCTATAATGAGCTGCAGA
AGGATAAGATGGCTGAAGCCTATTCTGAAATAGGCATGAAAGGAGAGCGG
AGAAGGGAAAAGGGCACGACGGTTTGTACCAGGGACTCAGCACTGCTAC
GAAGGATACTTATGACGCTCTCCACATGCAAGCCCTGCCACCTAGGTAA

Construct 1H2.1 4-1BB AA (Signal Sequence in Bold; CDRs Underlined)

(SEQ ID NO: 18)
MALPVTALLLPLALLLHAARPQVQLQESGPGLVKPSETLSLTCTVSGDSI
SSYYWTWIRQPPGKGLEWIGYIYYSGTTNYNPSLKSRVTISVDTSKSQFS
LKLSSVTAADTAVYYCASIAVRGFFFDYWGQGTLVTVSSGGGGSGGGGSG
GGGSEIVLTQSPGTLSLSPGERATLSCRASQSVSSSYLAWYQQKPGQAPR
LLIYGASTRATGIPDRFSGSGSGTDFTLTISRLEPEDFAVYYCQQYGTSP
LTFGGGTKVEIKRAAALDNEKSNGTIIHVKGKHLCPSPLFPGPSKPFWVL
VVVGGVLACYSLLVTVAFIIFWVRFSVVKRGRKKLLYIFKQPFMRPVQTT
QEEDGCSCRFPEEEEGGCELRVKFSRSADAPAYQQGQNQLYNELNLGRRE
EYDVLDKRRGRDPEMGGKPRRKNPQEGLYNELQKDKMAEAYSEIGMKGER
RRGKGHDGLYQGLSTATKDTYDALHMQALPPR

Construct 1H2.1 CD28T DNA (Signal Sequence in Bold)

(SEQ ID NO: 19)
**ATGGCACTCCCCGTAACTGCTCTGCTGCTGCCGTTGGCATTGCTCCTGCA
CGCCGCACGCCCG**CAGGTGCAACTGCAGGAAAGCGGGCCCGGTCTGGTGA
AGCCCTCAGAAACGCTCTCCCTCACCTGTACAGTCTCTGGCGATTCAATC
TCTTCATATTACTGGACGTGGATCAGGCAGCCTCCCGGCAAGGGACTGGA
GTGGATCGGATATATCTACTATAGTGGCACCACTAACTATAATCCTTCCC
TGAAAAGCCGGGTGACAATCTCTGTTGACACCTCCAAGAGCCAGTTCAGC
CTGAAACTCTCCAGTGTGACAGCCGCCGATACAGCCGTGTATTACTGTGC
CTCTATCGCTGTGCGCGGGTTCTTTTTTGATTATTGGGGCCAGGGGACAC
TGGTGACCGTTAGCAGCGGGGAGGAGGGTCCGGTGGCGGCGGCAGCGGA
GGCGGGGGTTCAGAAATTGTACTGACCCAGTCCCCCGGCACGCTCTCTCT
CTCCCCAGGGGAAAGGGCAACCCTTAGCTGCCGGGCGAGCCAGAGCGTGA
GTTCCTCCTACCTCGCGTGGTATCAGCAGAAGCCTGGACAGGCTCCCAGA
CTGCTGATTTACGGGCTTCTACGAGAGCCACCGGCATACCTGATAGGTT
CTCTGGCTCCGGGTCTGGGACCGACTTTACTCTTACAATCAGCAGACTTG
AGCCTGAAGACTTCGCTGTGTATTATTGTCAACAATACGGAACGTCCCCC
CTTACCTTTGGTGGCGGGACAAAAGTGGAAATTAAGAGGGCCGCTGCCCT
TGATAATGAAAAGTCAAACGGAACAATCATTCACGTGAAGGGCAAGCACC
TCTGTCCGTCACCCTTGTTCCCTGGTCCATCCAAGCCATTCTGGGTGTTG
GTCGTAGTGGGTGGAGTCCTCGCTTGTTACTCTCTGCTCGTCACCGTGGC
TTTTATAATCTTCTGGGTTAGATCCAAAAGAAGCCGCCTGCTCCATAGCG
ATTACATGAATATGACTCCACGCCGCCCTGGCCCCACAAGGAAACACTAC
CAGCCTTACGCACCACCTAGAGATTTCGCTGCCTATCGGAGCCGAGTGAA
ATTTTCTAGATCAGCTGATGCTCCCGCCTATCAGCAGGGACAGAATCAAC
TTTACAATGAGCTGAACCTGGGTCGCAGAGAAGAGTACGACGTTTTGGAC
AAACGCCGGGGCCGAGATCCTGAGATGGGGGGAAGCCGAGAAGGAAGAA
TCCTCAAGAAGGCCTGTACAACGAGCTTCAAAAAGACAAAATGGCTGAGG

CGTACTCTGAGATCGGCATGAAGGGCGAGCGGAGACGAGGCAAGGGTCAC
GATGGCTTGTATCAGGGCCTGAGTACAGCCACAAAGGACACCTATGACGC
CCTCCACATGCAGGCACTGCCCCCACGCTAG

Construct 1H2.1 CD28T AA (Signal Sequence in Bold; CDRs Underlined)

(SEQ ID NO: 20)
MALPVTALLLPLALLLHAARPQVQLQESGPGLVKPSETLSLTCTVSGDSI
SSYYWTWIRQPPGKGLEWIGYIYYSGTTNYNPSLKSRVTISVDTSKSQFS
LKLSSVTAADTAVYYCASIAVRGFFFDYWGQGTLVTVSSGGGGSGGGGSG
GGGSEIVLTQSPGTLSLSPGERATLSCRASQSVSSSYLAWYQQKPGQAPR
LLIYGASTRATGIPDRFSGSGSGTDFTLTISRLEPEDFAVYYCQQYGTSP
LTFGGGTKVEIKRAAALDNEKSNGTIIHVKGKHLCPSPLFPGPSKPFWVL
VVVGGVLACYSLLVTVAFIIFWVRSKRSRLLHSDYMNMTPRRPGPTRKHY
QPYAPPRDFAAYRSRVKFSRSADAPAYQQGQNQLYNELNLGRREEYDVLD
KRRGRDPEMGGKPRRKNPQEGLYNELQKDKMAEAYSEIGMKGERRRGKGH
DGLYQGLSTATKDTYDALHMQALPPR

Construct 8D2 4-1BB DNA (Signal Sequence in Bold)

(SEQ ID NO: 21)
**ATGGCACTCCCCGTAACTGCTCTGCTGCTGCCGTTGGCATTGCTCCTGCA
CGCCGCACGCCCG**CAGGTCCAGCTGGTGCAGTCTGGGGCAGAGGTGAAAC
GGCCGGGTGCAAGCGTGAAGGTGTCCTGCAAAGCCTCTGGCTATACCTTT
ACTGGGTACTATATGCACTGGGTTCGGCAGGCGCCAGGACAGGGTCTTGA
GTGGATGGGTTGGATTGATCCAAACTCTGGCGATACAAATTACGCACAGA
AATTCCAGGGCCGCGTGACGATGACTCGAGACACTTCCATATCCACCGCC
TATATGGAAGTGAATAGACTCCGGTCTGACGACACTGCTGTCTATTACTG
TGCAAGGGATCCCAACCGGCGGAGTTGGTATTACGGAATGGATGTCTGGG
CCCAGGGTACTACCGTCACGGTGTCTTCTGGCGGCGGGGGCTCAGGAGGA
GGAGGCAGCGGTGGAGGAGGCAGCGATATTCAGATGACACAAAGCCCTTC
TAGTCTCTCCGCAAGCGTTGGCGACCGCGTGACCATTACGTGTCAGGCTT
CACAAGATATTCGAAACTACCTGAACTGGTATCAGCAGAAGCCCGGCAAA
GCACCTAAGCTGCTGATTTATGACGCTAGCAACCTTGAGACTGGCGTCCC
CTCCAGATTTTCCGGCAGCGGCTCAGGCACCGACTTTACTTTTACCATCT
CCACACTCCAGCCAGAAGATATTGCAACGTATTACTGCCAACATTATGAT
AACCTGCCTTTGACCTTCGGAGGTGGCACCAAGGTAGAGATCAGAAGAGC
CGCTGCCCTTGATAATGAAAAGTCAAACGGAACAATCATTCACGTGAAGG
GCAAGCACCTCTGTCCGTCACCCTTGTTCCCTGGTCCATCCAAGCCATTC
TGGGTGTTGGTCGTAGTGGGTGGAGTCCTCGCTTGTTACTCTCTGCTCGT
CACCGTGGCTTTTATAATCTTCTGGGTTCGCTTTTCCGTCGTTAAGCGGG
GGAGAAAAAGCTGCTGTACATTTTCAAACAGCCGTTTATGAGGCCGGTC
CAAACGACTCAGGAAGAAGACGGCTGCTCCTGCCGCTTTCCTGAGGAGGA
GGAGGGCGGGTGCGAACTGAGGGTGAAGTTTTCCAGATCTGCAGATGCAC

CAGCGTATCAGCAGGGCCAGAACCAACTGTATAACGAGCTCAACCTGGGA

CGCAGGGAAGAGTATGACGTTTTGGACAAGCGCAGAGGACGGGACCCTGA

GATGGGTGGCAAACCAAGACGAAAAAACCCCCAGGAGGGTCTCTATAATG

AGCTGCAGAAGGATAAGATGGCTGAAGCCTATTCTGAAATAGGCATGAAA

GGAGAGCGGAGAAGGGGAAAAGGGCACGACGGTTTGTACCAGGGACTCAG

CACTGCTACGAAGGATACTTATGACGCTCTCCACATGCAAGCCCTGCCAC

CTAGGTAA

Construct 8D2 4-1BB AA (Signal Sequence in Bold)

(SEQ ID NO: 22)

MALPVTALLLPLALLLHAARPQVQLVQSGAEVKRPGASVKVSCKASGYTF

TGYYMHWVRQAPGQGLEWMGWIDPNSGDTNYAQKFQGRVTMTRDTSISTA

YMEVNRLRSDDTAVYYCARDPNRRSWYYGMDVWAQGTTVTVSSGGGGSGG

GGSGGGGSDIQMTQSPSSLSASVGDRVTITCQASQDIRNYLNWYQQKPGK

APKLLIYDASNLETGVPSRFSGSGSGTDFTFTISTLQPEDIATYYCQHYD

NLPLTFGGGTKVEIRRAAALDNEKSNGTIIHVKGKHLCPSPLFPGPSKPF

WVLVVVGGVLACYSLLVTVAFIIFWVRFSVVKRGRKKLLYIFKQPFMRPV

QTTQEEDGCSCRFPEEEGGCELRVKFSRSADAPAYQQGQNQLYNELNLG

RREEYDVLDKRRGRDPEMGGKPRRKNPQEGLYNELQKDKMAEAYSEIGMK

GERRRGKGHDGLYQGLSTATKDTYDALHMQALPPR

Construct 8D2 CD28T DNA (Signal Sequence in Bold)

(SEQ ID NO: 23)

ATGGCACTCCCCGTAACTGCTCTGCTGCTGCCGTTGGCATTGCTCCTGCA

CGCCGCACGCCCGCAGGTCCAGCTGGTGCAGTCTGGGGCAGAGGTGAAAC

GGCCGGGTGCAAGCGTGAAGGTGTCCTGCAAAGCCTCTGGCTATACCTTT

ACTGGGTACTATATGCACTGGGTTCGGCAGGCGCCAGGACAGGGTCTTGA

GTGGATGGGTTGGATTGATCCAAACTCTGGCGATACAAATTACGCACAGA

AATTCCAGGGCCGCGTGACGATGACTCGAGACACTTCCATATCCACCGCC

TATATGGAAGTGAATAGACTCCGGTCTGACGACACTGCTGTCTATTACTG

TGCAAGGGATCCCAACCGGCGGAGTTGGTATTACGGAATGGATGTCTGGG

CCCAGGGTACTACCGTCACGGTGTCTTCTGGCGGCGGGGCTCAGGAGGA

GGAGGCAGCGGTGGAGGAGGCAGCGATATTCAGATGACACAAAGCCCTTC

TAGTCTCTCCGCAAGCGTTGGCGACCGCGTGACCATTACGTGTCAGGCTT

CACAAGATATTCGAAACTACCTGAACTGGTATCAGCAGAAGCCCGGCAAA

GCACCTAAGCTGCTGATTTATGACGCTAGCAACCTTGAGACTGGCGTCCC

CTCCAGATTTTCCGGCAGCGGCTCAGGCACCGACTTTACTTTTACCATCT

CCACACTCCAGCCAGAAGATATTGCAACGTATTACTGCCAACATTATGAT

AACCTGCCTTTGACCTTCGGAGGTGGCACCAAGGTAGAGATCAGAAGAGC

CGCTGCCCTTGATAATGAAAAGTCAAACGGAACAATCATTCACGTGAAGG

GCAAGCACCTCTGTCCGTCACCCTTGTTCCCTGGTCCATCCAAGCCATTC

TGGGTGTTGGTCGTAGTGGGTGGAGTCCTCGCTTGTTACTCTCTGCTCGT

CACCGTGGCTTTTATAATCTTCTGGGTTAGATCCAAAAGAAGCCGCCTGC

TCCATAGCGATTACATGAATATGACTCCACGCCGCCCTGGCCCCACAAGG

AAACACTACCAGCCTTACGCACCACCTAGAGATTTCGCTGCCTATCGGAG

CCGAGTGAAATTTTCTAGATCAGCTGATGCTCCCGCCTATCAGCAGGGAC

AGAATCAACTTTACAATGAGCTGAACCTGGGTCGCAGAGAAGAGTACGAC

GTTTTGGACAAACGCCGGGGCCGAGATCCTGAGATGGGGGGAAGCCGAG

AAGGAAGAATCCTCAAGAAGGCCTGTACAACGAGCTTCAAAAAGACAAAA

TGGCTGAGGCGTACTCTGAGATCGGCATGAAGGGCGAGCGGAGACGAGGC

AAGGGTCACGATGGCTTGTATCAGGGCCTGAGTACAGCCACAAAGGACAC

CTATGACGCCCTCCACATGCAGGCACTGCCCCCACGCTAG

Construct 8D2 CD28T AA (Signal Sequence in Bold)

(SEQ ID NO: 24)

MALPVTALLLPLALLLHAARPQVQLVQSGAEVKRPGASVKVSCKASGYTF

TGYYMHWVRQAPGQGLEWMGWIDPNSGDTNYAQKFQGRVTMTRDTSISTA

YMEVNRLRSDDTAVYYCARDPNRRSWYYGMDVWAQGTTVTVSSGGGGSGG

GGSGGGGSDIQMTQSPSSLSASVGDRVTITCQASQDIRNYLNWYQQKPGK

APKLLIYDASNLETGVPSRFSGSGSGTDFTFTISTLQPEDIATYYCQHYD

NLPLTFGGGTKVEIRRAAALDNEKSNGTIIHVKGKHLCPSPLFPGPSKPF

WVLVVVGGVLACYSLLVTVAFIIFWVRSKRSRLLHSDYMNMTPRRPGPTR

KHYQPYAPPRDFAAYRSRVKFSRSADAPAYQQGQNQLYNELNLGRREEYD

VLDKRRGRDPEMGGKPRRKNPQEGLYNELQKDKMAEAYSEIGMKGERRRG

KGHDGLYQGLSTATKDTYDALHMQALPPR

Construct 6B2 CD28T DNA (Signal Sequence in Bold)

(SEQ ID NO: 25)

ATGGCACTCCCCGTAACTGCTCTGCTGCTGCCGTTGGCATTGCTCCTGCA

CGCCGCACGCCCGCAAGTGCAGTTGGTGCAGTCTGGGAGCTGAAGTGAAGA

AACCAGGCGCTAGCGTCAAAGTGAGCTGTAAGGCCTCAGGTTACACGTTT

ACTGGGTACTATATGCATTGGGTCAGGCAAGCCCCTGGCCAGGGCCTCGA

GTGGATGGGCTGGATTAATCCTAACAGCGGGGACACAAGCTATGCCCAAC

GCTTCCTGGGCAGAGTAACAATGACACGGGATACAAGTATTAACACCGTC

CATATGGAACTCTCTCGGCTCGGCTCAGATGATACCGCGGTTTATTACTG

TGCTAGGGAGGACGACTCCTCTTGGTATGGCAGCTTCGATTATTGGGGC

AGGGAACCCTGGTGACAGTCTCATCTGGTGGAGGGGCTCCGGGGGTGGG

GGCAGCGGAGGGGAGGTTCTGATATACAGATGACTCAGAGTCCCTCAAG

CTTGAGTGCCAGTGTAGGCGACCGGGTGACGATAACCTGTAGGGCTTCAC

AGGGAATCAGAAATTATCTGGTTGGTACCAGCAGAAGCCAGGAAAGGCA

CCTAAAAGACTTATTTACGCCGCATCCTCCTTGCAGTCCGGCGTGCCATC

AAAATTTCTGGGAGCGGCTCTGGAACCGAGTTCACCCTCACGATCTCCA

GCCTCCAGCCCGAGGACTTTGCCACCTACTATTGCCTGCAGCACGATAGT

GATCTGCGAACTTTTGGGCAAGGCACTAAAGTGGAAATTAAGAGAGCCGC

-continued

TGCCCTTGATAATGAAAAGTCAAACGGAACAATCATTCACGTGAAGGGCA

AGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCAC

CGTGGCTTTTATAATCTTCTGGGTTAGATCCAAAAGAAGCCGCCTGCTCC

ATAGCGATTACATGAATATGACTCCACGCCGCCCTGGCCCCACAAGGAAA

CACTACCAGCCTTACGCACCACCTAGAGATTTCGCTGCCTATCGGAGCCG

AGTGAAATTTTCTAGATCAGCTGATGCTCCCGCCTATCAGCAGGGACAGA

ATCAACTTTACAATGAGCTGAACCTGGGTCGCAGAGAAGAGTACGACGTT

TTGGACAAACGCCGGGGCCGAGATCCTGAGATGGGGGGGAAGCCGAGAAG

GAAGAATCCTCAAGAAGGCCTGTACAACGAGCTTCAAAAAGACAAAATGG

CTGAGGCGTACTCTGAGATCGGCATGAAGGGCGAGCGGAGACGAGGCAAG

GGTCACGATGGCTTGTATCAGGGCCTGAGTACAGCCACAAAGGACACCTA

TGACGCCCTCCACATGCAGGCACTGCCCCCACGCTAG

Construct 6B2 CD28T AA (Signal Sequence in Bold)

(SEQ ID NO: 26)
MALPVTALLLPLALLLHAARPQVQLVQSGAEVKKPGASVKVSCKASGYTF

TGYYMHWVRQAPGQGLEWMGWINPNSGDTSYAQRFLGRVTMTRDTSINTV

HMELSRLGSDDTAVYYCAREDDSSWYGSFDYWGQGTLVTVSSGGGGSGGG

GSGGGGSDIQMTQSPSSLSASVGDRVTITCRASQGIRNYLGWYQQKPGKA

PKRLIYAASSLQSGVPSKFSGSGSGTEFTLTISSLQPEDFATYYCLQHDS

DLRTFGQGTKVEIKRAAALDNEKSNGTIIHVGKHLCPSPLFPGPSKPFW

VLVVVGGVLACYSLLVTVAFIIFWVRSKRSRLLHSDYMNMTPRRPGPTRK

HYQPYAPPRDFAAYRSRVKFSRSADAPAYQQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR

Construct 6B2 4-1BB DNA (Signal Sequence in Bold)

(SEQ ID NO: 27)
ATGGCACTCCCCGTAACTGCTCTGCTGCTGCCGTTGGCATTGCTCCTGCA
CGCCGCACGCCCGCAAGTGCAGTTGGTGCAGTCTGGAGCTGAAGTGAAGA

AACCAGGCGCTAGCGTCAAAGTGAGCTGTAAGGCCTCAGGTTACACGTTT

ACTGGGTACTATATGCATTGGGTCAGGCAAGCCCCTGGCCAGGGCCTCGA

GTGGATGGGCTGGATTAATCCTAACAGCGGGGACACAAGCTATGCCCAAC

GCTTCCTGGGCAGAGTAACAATGACACGGGATACAAGTATTAACACCGTC

CATATGGAACTCTCTCGGCTCGGCTCAGATGATACCGCGGTTTATTACTG

TGCTAGGGAGGACGACTCCTCTTGGTATGGCAGCTTCGATTATTGGGGC

AGGGAACCCTGGTGACAGTCTCATCTGGTGGAGGGGCTCCGGGGGTGGG

GGCAGCGGAGGGGAGGTTCTGATATACAGATGACTCAGAGTCCCTCAAG

CTTGAGTGCCAGTGTAGGCGACCGGGTGACGATAACCTGTAGGGCTTCAC

AGGGAATCAGAAATTATCTGGGTTGGTACCAGCAGAAGCCAGGAAAGGCA

CCTAAAAGACTTATTTACGCCGCATCCTCCTTGCAGTCCGGCGTGCCATC

AAAATTTTCTGGGAGCGGCTCTGGAACCGAGTTCACCCTCACGATCTCCA

GCCTCCAGCCCGAGGACTTTGCCACCTACTATTGCCTGCAGCACGATAGT

GATCTGCGAACTTTTGGGCAAGGCACTAAAGTGGAAATTAAGAGAGCCGC

TGCCCTTGATAATGAAAAGTCAAACGGAACAATCATTCACGTGAAGGGCA

AGCACCTCTGTCCGTCACCCTTGTTCCCTGGTCCATCCAAGCCATTCTGG

GTGTTGGTCGTAGTGGGTGGAGTCCTCGCTTGTTACTCTCTGCTCGTCAC

CGTGGCTTTTATAATCTTCTGGGTTCGCTTTTCCGTCGTTAAGCGGGGGA

GAAAAAAGCTGCTGTACATTTTCAAACAGCCGTTTATGAGGCCGGTCCAA

ACGACTCAGGAAGAAGACGGCTGCTCCTGCCGCTTTCCTGAGGAGGAGGA

GGGCGGGTGCGAACTGAGGGTGAAGTTTTCCAGATCGCAGATGCACCAG

CGTATCAGCAGGGCCAGAACCAACTGTATAACGAGCTCAACCTGGGACGC

AGGGAAGAGTATGACGTTTTGGACAAGCGCAGAGGACGGGACCCTGAGAT

GGGTGGCAAACCAAGACGAAAAAACCCCCAGGAGGGTCTCTATAATGAGC

TGCAGAAGGATAAGATGGCTGAAGCCTATTCTGAAATAGGCATGAAGGGA

GAGCGGAGAAGGGGAAAAGGGCACGACGGTTTGTACCAGGGACTCAGCAC

TGCTACGAAGGATACTTATGACGCTCTCCACATGCAAGCCCTGCCACCTA

GGTAA

Construct 6B2 4-1BB AA (Signal Sequence in Bold)

(SEQ ID NO: 28)
MALPVTALLLPLALLLHAARPQVQLVQSGAEVKKPGASVKVSCKASGYTF

TGYYMHWVRQAPGQGLEWMGWINPNSGDTSYAQRFLGRVTMTRDTSINTV

HMELSRLGSDDTAVYYCAREDDSSWYGSFDYWGQGTLVTVSSGGGGSGGG

GSGGGGSDIQMTQSPSSLSASVGDRVTITCRASQGIRNYLGWYQQKPGKA

PKRLIYAASSLQSGVPSKFSGSGSGTEFTLTISSLQPEDFATYYCLQHDS

DLRTFGQGTKVEIKRAAALDNEKSNGTIIHVGKHLCPSPLFPGPSKPFW

VLVVVGGVLACYSLLVTVAFIIFWVRFSVVKRGRKKLLYIFKQPFMRPVQ

TTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPR

Human DLL3 Isoform 1 NM_016941 AA (618 Amino Acids)

(SEQ ID NO: 29)
MVSPRMSGLLSQTVILALIFLPQTRPAGVFELQIHSFGPGPGPAPRSPC

SARLPCRLFFRVCLKPGLSEEAAESPCALGAALSARGPVYTEQPGAPAPD

LPLPDGLLQVPFRDAWPGTFSFIIETWREELGDQIGGPAWSLLARVAGRR

RLAAGGPWARDIQRAGAWELRFSYRARCEPPAVGTACTRLCRPRSAPSRC

GPGLRPCAPLEDECEAPLVCRAGCSPEHGFCEQPGECRCLEGWTGPLCTV

PVSTSSCLSPRGPSSATTGCLVPGPGPCDGNPCANGGSCSETPRSFECTC

PRGFYGLRCEVSGVTCADGPCFNGGLCVGGADPDSAYICHCPPGFQGSNC

EKRVDRCSLQPCRNGGLCLDLGHALRCRCRAGFAGPRCEHDLDDCAGRAC

-continued
ANGGTCVEGGGAHRCSCALGFGGRDCRERADPCAARPCAHGGRCYAHFSG

LVCACAPGYMGARCEFPVHPDGASALPAAPPGLRPGDPQRYLLPPALGLL

VAAGVAGAALLLVHVRRRGHSQDAGSRLLAGTPEPSVHALPDALNNLRTQ

EGSGDGPSSSVDWNRPEDVDPQGIYVISAPSIYAREVATPLFPPLHTGRA

GQRQHLLFPYPSSILSVK

Human DLL3 Isoform 2 NM_203486 AA (587 Amino Acids)

(SEQ ID NO: 30)
MVSPRMSGLLSQTVILALIFLPQTRPAGVFELQIHSFGPGPGPGAPRSPC

SARLPCRLFFRVCLKPGLSEEAAESPCALGAALSARGPVYTEQPGAPAPD

LPLPDGLLQVPFRDAWPGTFSFIIETWREELGDQIGGPAWSLLARVAGRR

RLAAGGPWARDIQRAGAWELRFSYRARCEPPAVGTACTRLCRPRSAPSRC

GPGLRPCAPLEDECEAPLVCRAGCSPEHGFCEQPGECRCLEGWTGPLCTV

PVSTSSCLSPRGPSSATTGCLVPGPGPCDGNPCANGGSCSETPRSFECTC

PRGFYGLRCEVSGVTCADGPCFNGGLCVGGADPDSAYICHCPPGFQGSNC

EKRVDRCSLQPCRNGGLCLDLGHALRCRCRAGFAGPRCEHDLDDCAGRAC

ANGGTCVEGGGAHRCSCALGFGGRDCRERADPCAARPCAHGGRCYAHFSG

LVCACAPGYMGARCEFPVHPDGASALPAAPPGLRPGDPQRYLLPPALGLL

VAAGVAGAALLLVHVRRRGHSQDAGSRLLAGTPEPSVHALPDALNNLRTQ

EGSGDGPSSSVDWNRPEDVDPQGIYVISAPSIYAREA

CAR Signal Peptide DNA (SEQ ID NO: 31)
ATGGCACTCCCCGTAACTGCTCTGCTGCTGCCGTTGGCATTGCTCCTGCA

CGCCGCACGCCCG

CAR Signal Peptide:

(SEQ ID NO: 32)
MALPVTALLLPLALLLHAARP scFv G45 Linker DNA (SEQ ID NO: 33)
GGCGGTGGAGGCTCCGGAGGGGGGGCTCTGGCGGAGGGGCTCC scFv G4s Linker:

(SEQ ID NO: 34)
GGGGSGGGGSGGGGS scFv Whitlow Linker DNA (SEQ ID NO: 35)
GGGTCTACATCCGGCTCCGGGAAGCCCGGAAGTGGCGAAGGTAGTACAAA

GGGG scFv Whitlow Linker:

(SEQ ID NO: 36)
GSTSGSGKPGSGEGSTKG 4-1BB Nucleic Acid Sequence (Intracellular Domain)

(SEQ ID NO: 37)
AAGCGGGGGAGAAAAAAGCTGCTGTACATTTTCAAACAGCCGTTTATGAG

GCCGGTCCAAACGACTCAGGAAGAAGACGGCTGCTCCTGCCGCTTTCCTG

AGGAGGAGGAGGGCGGGTGCGAACTG 4-1BB AA (Intracellular Domain)

(SEQ ID NO: 38)
KRGRKKLLYIFKQPFMRPVQTTQEEDGCSCRFPEEEEGGCEL

OX40 AA (SEQ ID NO: 39)
RRDQRLPPDAHKPPGGGSFRTPIQEEQADAHSTLAKI

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The following examples, including the experiments conducted and results achieved, are provided for illustrative purposes only and are not to be construed as limiting the present invention.

Example 1

Figure 1B:
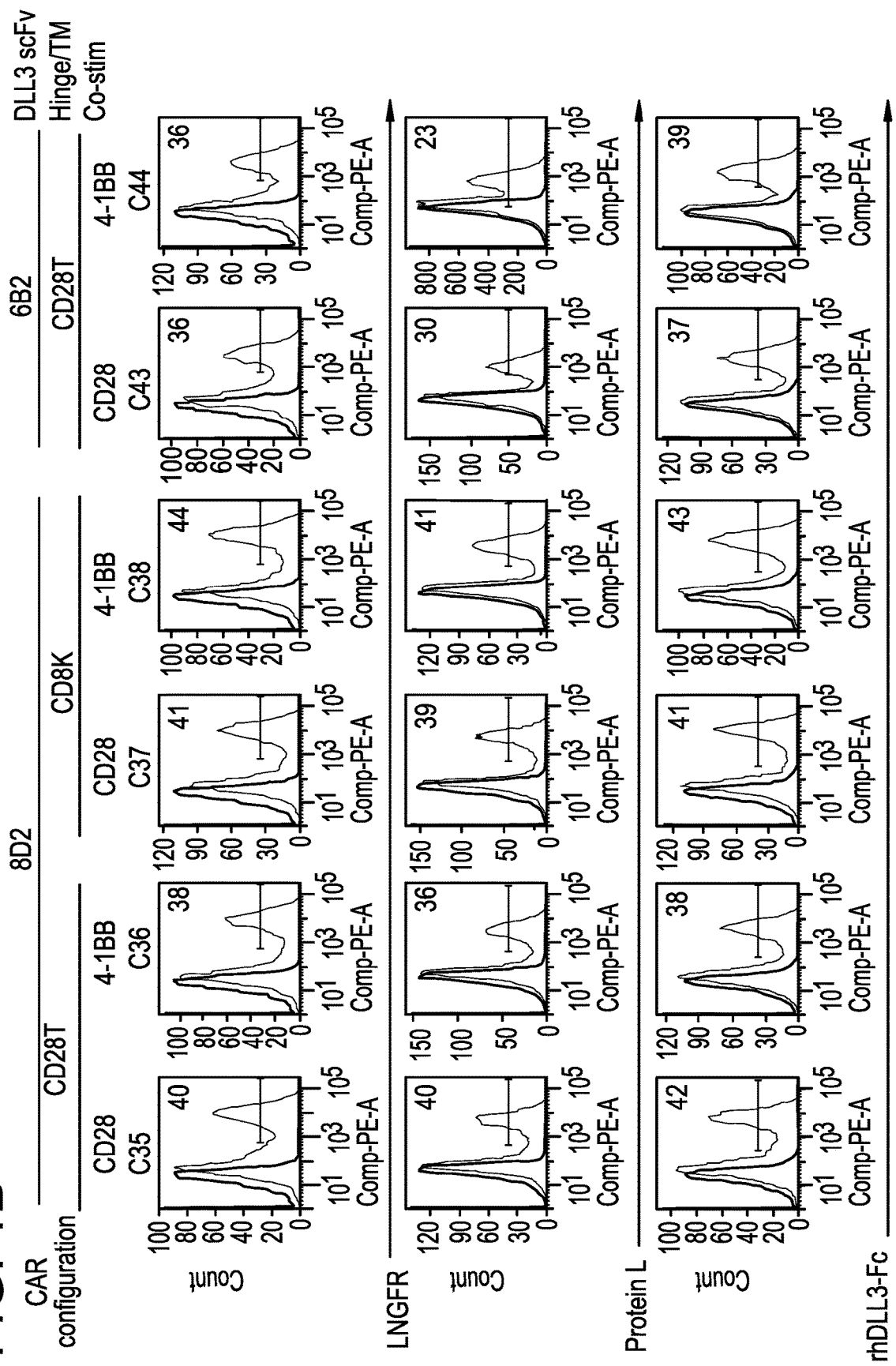

A third generation lentiviral transfer vector containing the different CAR constructs was used along with the ViraPower Lentiviral Packaging Mix (Life Technologies) to generate the lentiviral supernatants. Briefly, a transfection mix was generated by mixing 15 μg of DNA and 22.5 μl of polyethyleneimine (Polysciences, 1 mg/ml) in 600 μl of OptiMEM medium. The mix was incubated for 5 minutes at room temperature. Simultaneously, 293T cells (ATCC) were trypsinized, counted and a total of 10×106 total cells were plated in a T75 flask along the transfection mix. Three days after the transfection, supernatants were collected and filtered through a 0.45 μm filter and stored at −80° C. until used. PBMCs were isolated from healthy donor leukopaks (Hemacare) using ficoll-paque density centrifugation per manufacturer's instructions. PBMCs were stimulated using OKT3 (50 ng/ml, Miltenyi Biotec) in R10 medium+IL-2 (300 IU/ml, Proleukin®, Prometheus® Therapeutics and Diagnostics). Forty eight hours post-stimulation, cells were transduced using lentivirus at an MOI=10. Cells were maintained at 0.5-2.0×106 cells/ml prior to use in activity assays. To examine CAR expression, T cells were stained with DLL3-Fc detection reagent (Amgen, Inc.) or biotinylated Protein L (Thermo Scientific) in stain buffer (BD Pharmingen) for 30 minutes at 4° C. Cells were then washed and stained with anti-Fc-PE (Miltenyi Biotec) or PE Streptavidin (BD Pharmingen) in stain buffer for 30 minutes at 4° C. Cells were then washed and resuspended in stain buffer with propidium iodide (BD Pharmingen) prior to data acquisition. Expression of DLL3 CARs in T cells from a healthy donor is shown in FIGS. 1A and 1B. Numbers in each box indicate the percent positive population.

Example 2

Figure 3A:
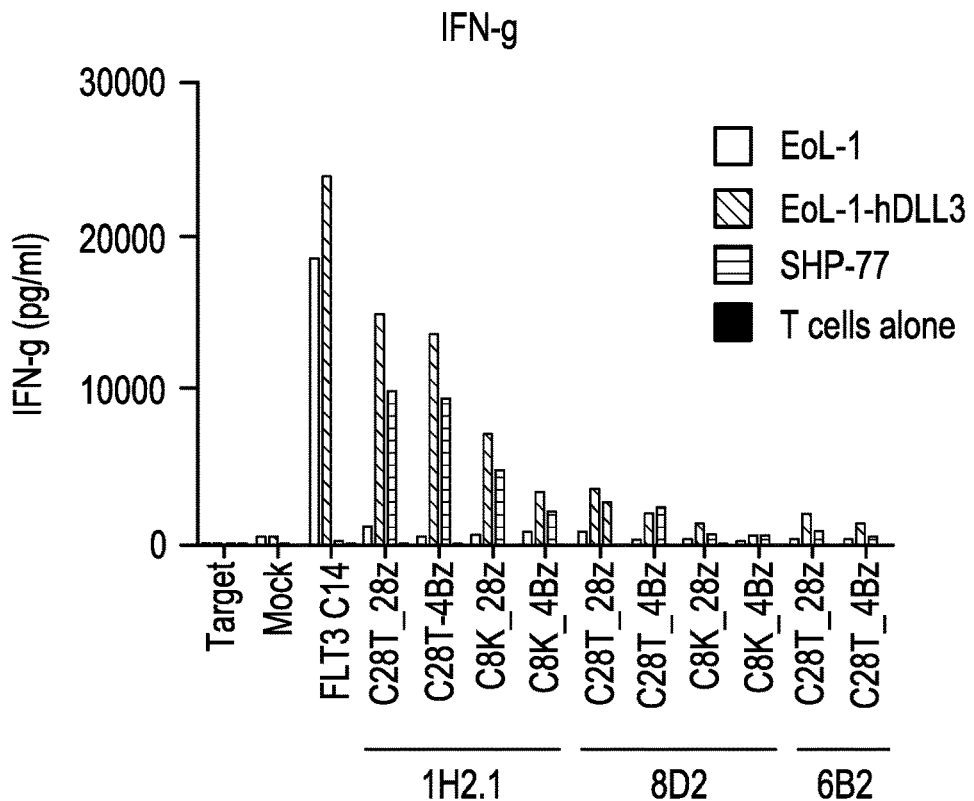
FIG. 3A-B, depicts cytokine production by CAR T cells from a healthy donor.
Figure 3B:
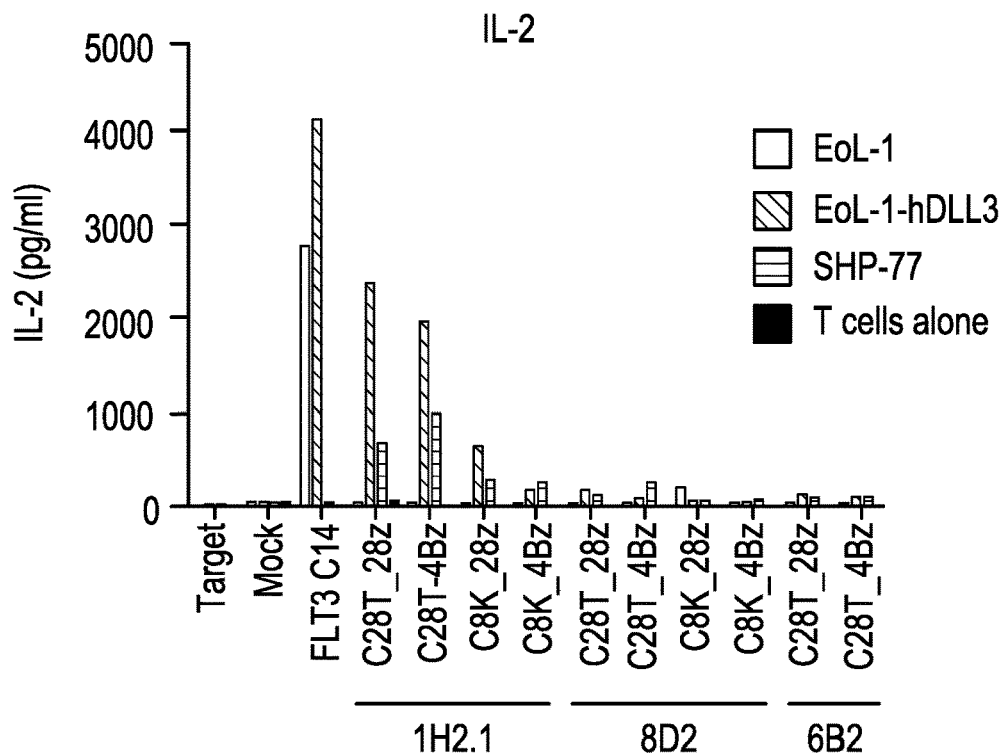
Figure 3C:
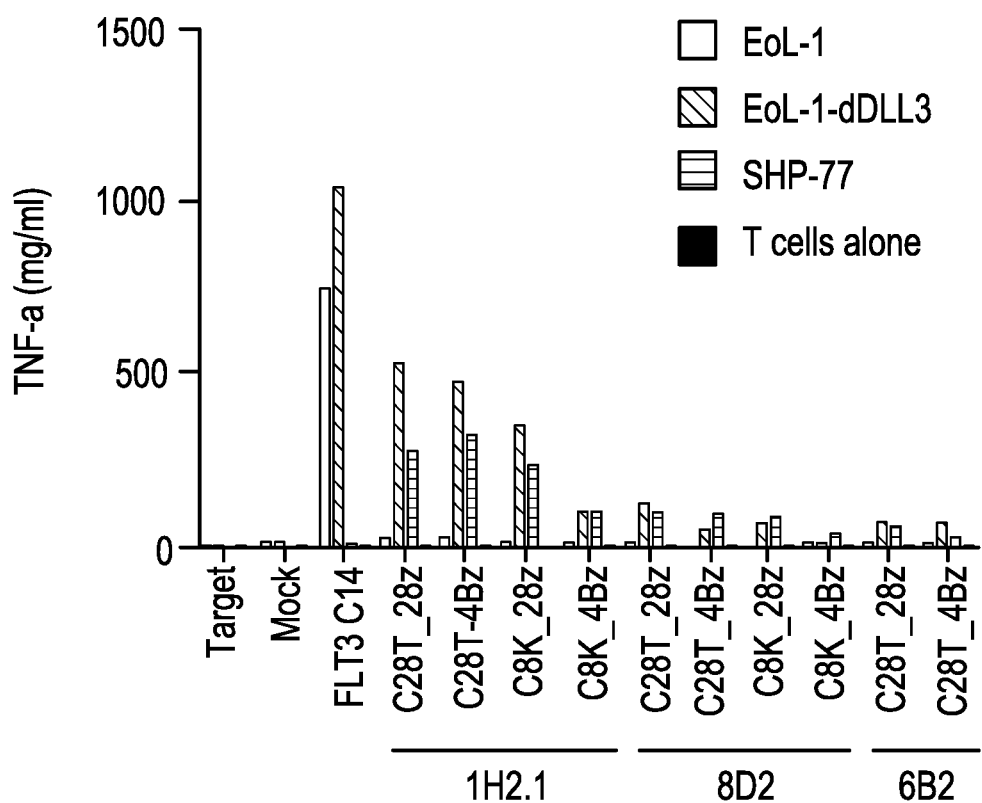

To examine cytolytic activity in lentivirus-transduced DLL3 CAR T cells, effector cells were cultured with target cells at a 1:1 E:T ratio in R10 medium. Sixteen and forty hours post-coculture, supernatants were analyzed by Luminex (EMD Millipore) and target cell viability was assessed by flow cytometric analysis of propidium iodide (PI) uptake by CD3-negative cells. Average cytolytic activity of lentivirus-transduced CAR T cells from healthy donors is shown in FIG. 2 (EoL1 cells are control (FIG. 2A), H82 (FIG. 2C) and EoL1-DLL3 (FIG. 2B) express DLL3 on the surface) and cytokine production by CAR T cells from a healthy donor is shown in FIG. 3A-C.

Example 3

Figure 4A:
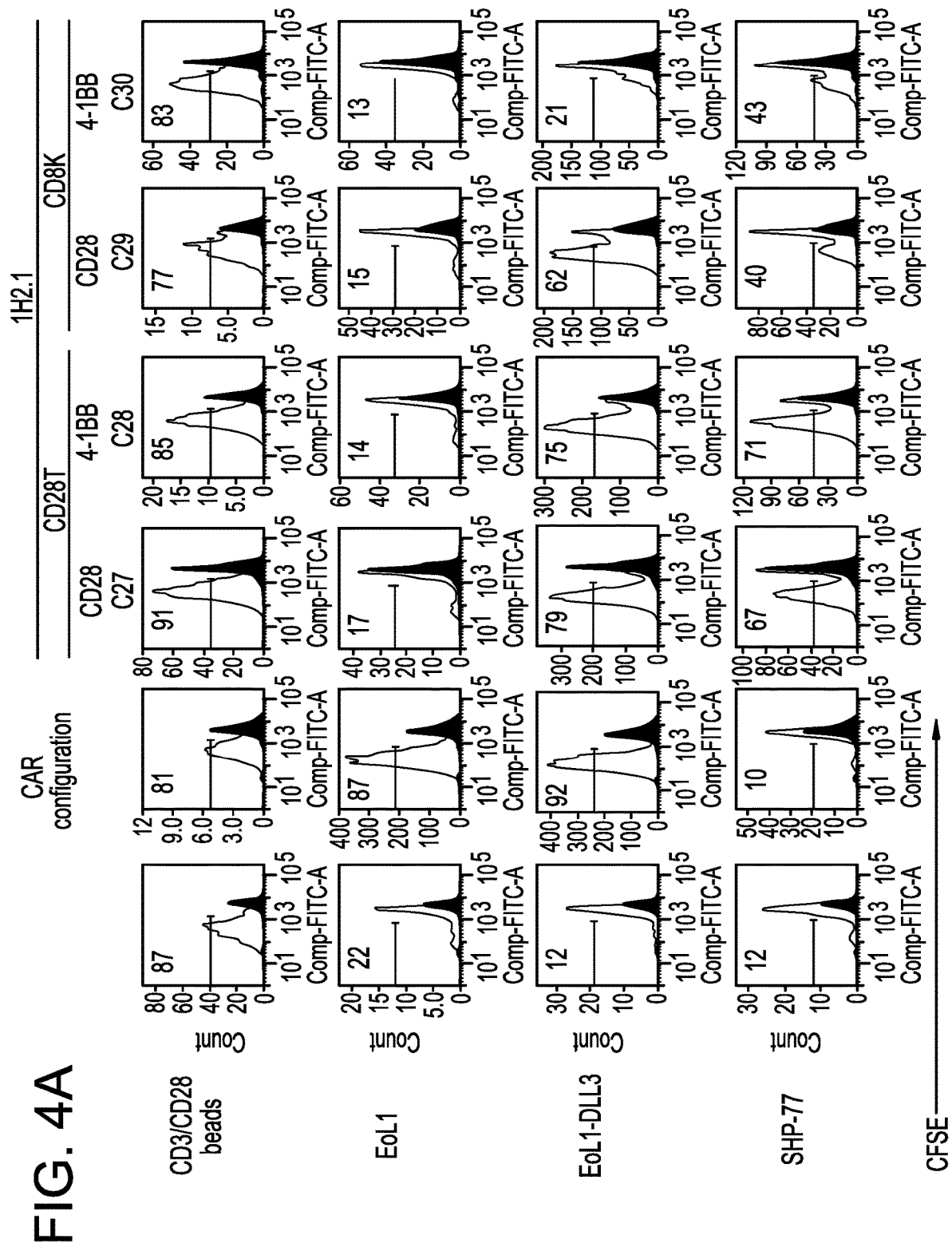
FIG. 4A-B depicts flow cytometric analysis of T cell proliferation in response to DLL3-expressing target cells.
Figure 4B:
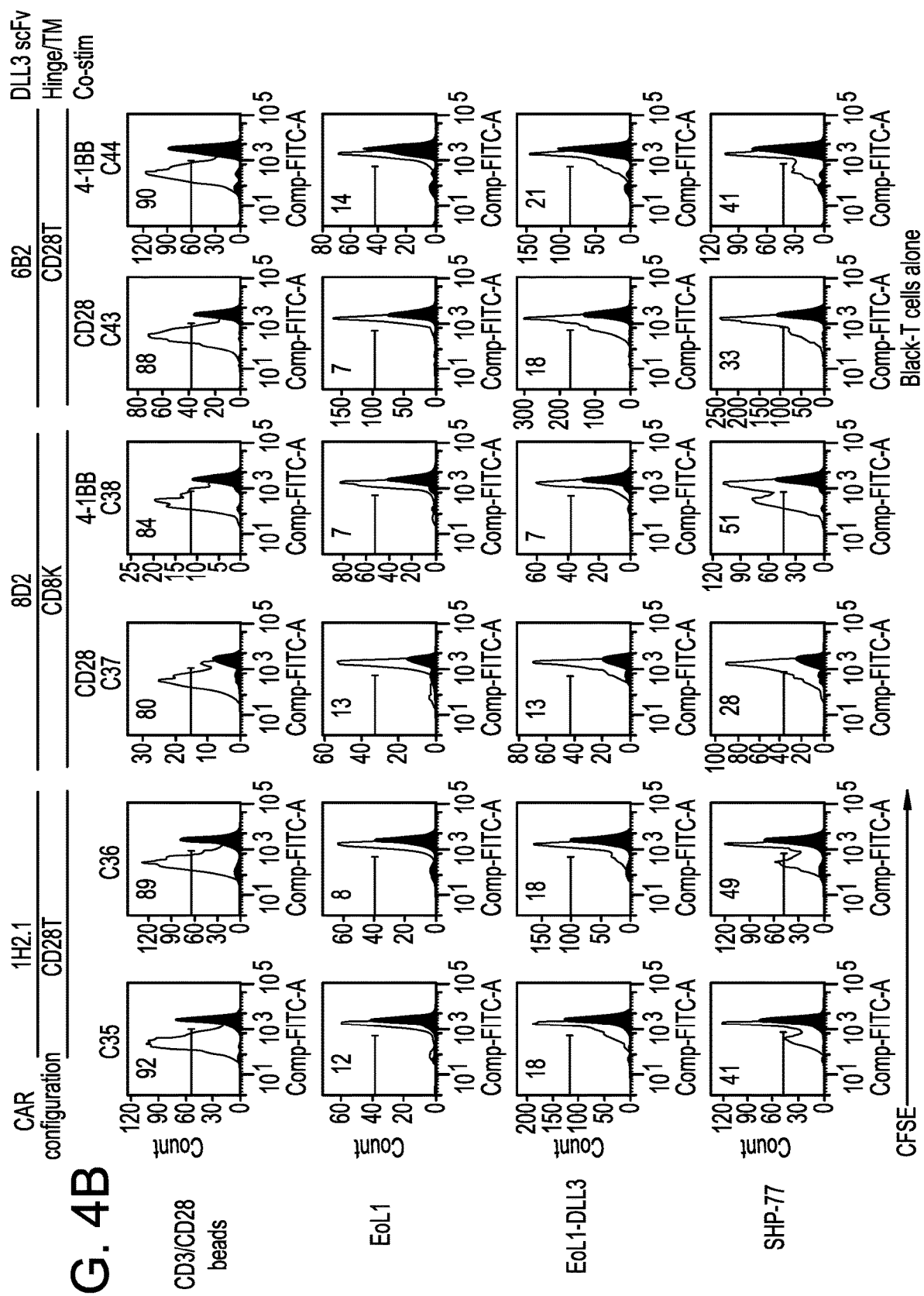
Figure 5:
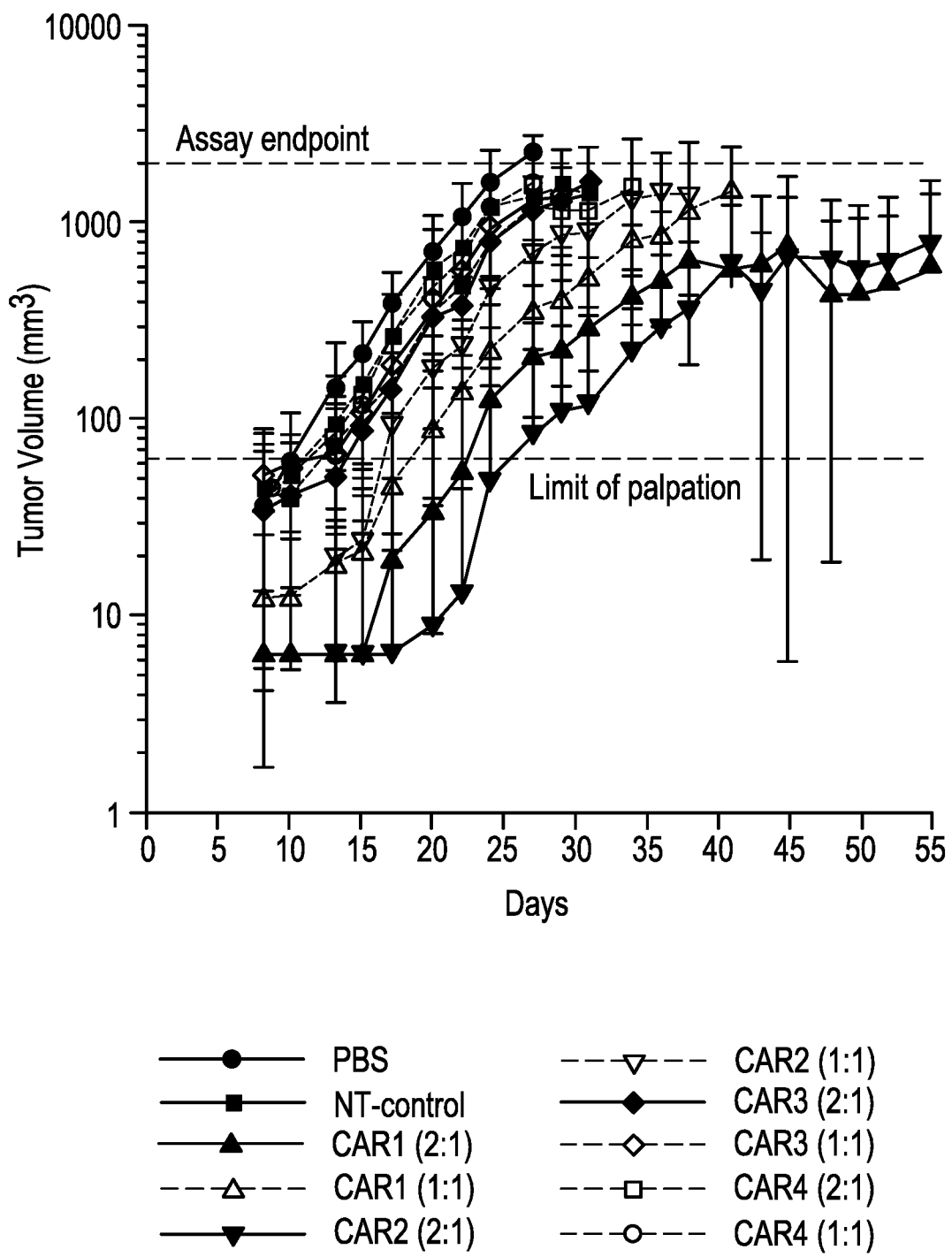
FIG. 5, depicts in vivo anti-tumor activity of DLL3 CAR T cells in mouse xenogeneic model of human SCLC.

To assess CAR T cell proliferation in response to DLL3-expressing target cells, T cells were labeled with CFSE prior to co-culture with target cells at a 1:1 ET ratio in R10 medium. Five days later, T cell proliferation was assessed by flow cytometric analysis of CFSE dilution (FIGS. 4A and 4B). Proliferation of DLL3 CAR T cells is shown in FIG. 5.

Example 4

Figure 6:
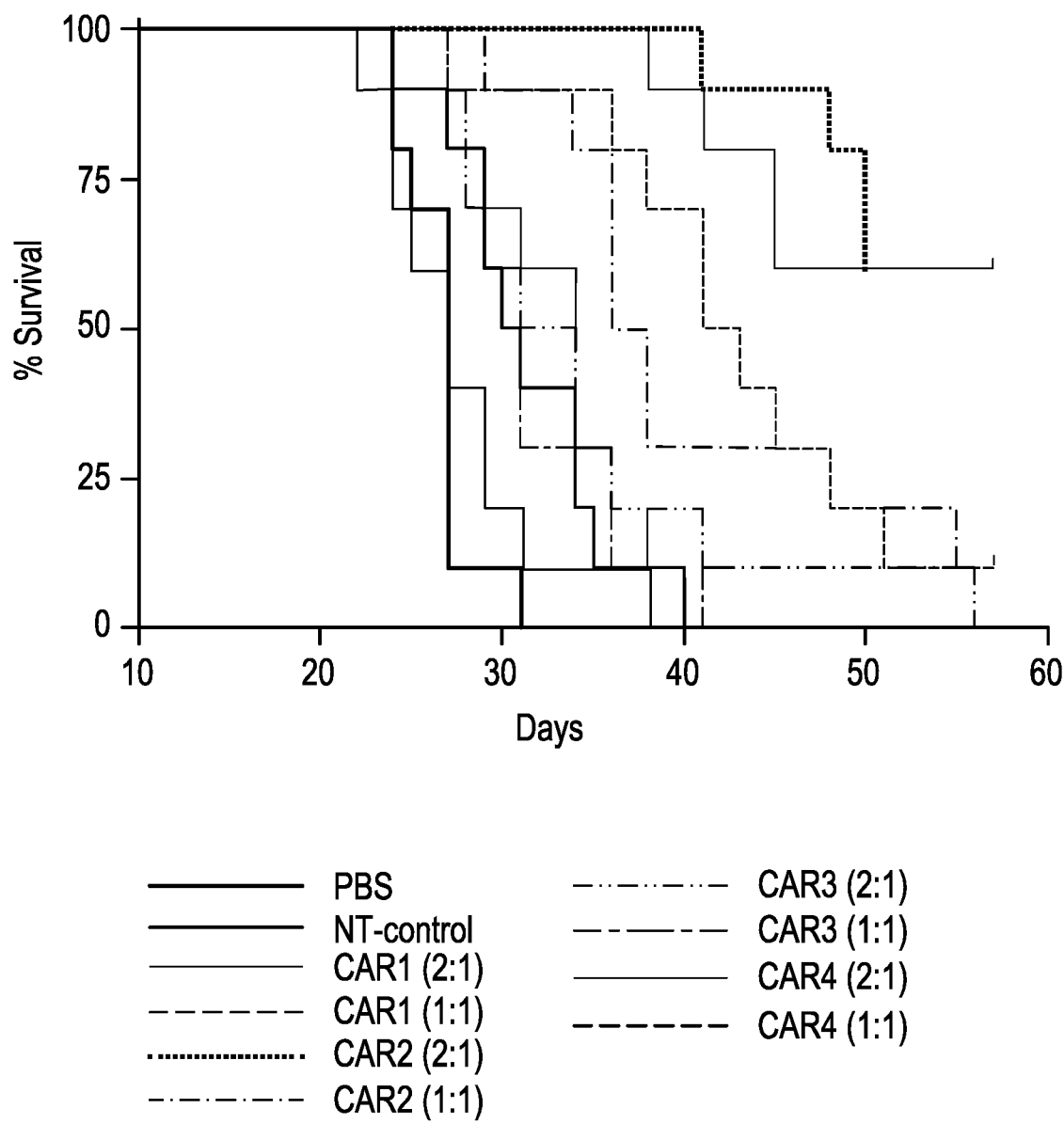
FIG. 6, depicts survival analysis of mouse SCLC xenogeneic model following DLL3 CAR T cell treatment.

To examine in vivo anti-tumor activity, DLL3 CAR T cells were generated for use in a xenogeneic model of human SCLC. Luciferase-labeled SHP-77 cells (2×106/animal) were injected intravenously into 5 to 6 week-old female NSG mice. After 6 days, 6×106 T cells (~50% CAR+) in 200 µl PBS were injected intravenously and the tumor burden of the animals was measured weekly using bioluminescence imaging. As shown in FIG. 6, injection of DLL3 CAR T cells significantly reduced the tumor burden at all time points examined (nt=non-transfected control; CAR1=1H2.1-C28T-CD28-CD3ζ; CAR2=1H2.1-C28T-4-1BB-CD3ζ; CAR3=1H2.1-C8k-CD28-CD3ζ; CAR4=1H2.1-C8k-4-1BB-CD3ζ). As shown in FIG. 6, this was further confirmed with survival analysis where injection of the 1H2-CD28T or 1H2-4-1BB expressing CAR T cells conferred a significant survival advantage over animals that received mock transduced cells.

What is claimed:

1. A chimeric antigen receptor comprising
   (i) an antigen binding molecule that specifically binds to DLL3, a costimulatory domain, and an activating domain that is a signaling domain of CD3 zeta, wherein the antigen binding molecule comprises:
   a variable heavy chain region comprising complementary determining regions ("CDRs") 1, 2, and 3 with amino acid sequences SEQ ID NO:42, SEQ ID NO:43, and SEQ ID NO:44, respectively, and a variable light chain region comprising CDRs 1, 2, and 3 with amino acid sequences SEQ ID NO:47, SEQ ID NO:48, and SEQ ID NO:49, respectively; or
   a variable heavy chain region comprising complementary determining regions ("CDRs") 1, 2, and 3 with amino acid sequences SEQ ID NO:52, SEQ ID NO:53, and SEQ ID NO:54, respectively, and a variable light chain region comprising CDRs 1, 2, and 3 with amino acid sequences SEQ ID NO:57, SEQ ID NO:58, and SEQ ID NO:59, respectively; or
   a variable heavy chain region comprising complementary determining regions ("CDRs") 1, 2, and 3 with amino acid sequences SEQ ID NO:62, SEQ ID NO:63, and SEQ ID NO:64, respectively, and a variable light chain region comprising CDRs 1, 2, and 3 with amino acid sequences SEQ ID NO:67, SEQ ID NO:68, and SEQ ID NO:69, respectively; or
   a VH region of SEQ ID NO:41 and a VL region of SEQ ID NO:46, or
   a VH region having at least 90% identity to the amino acid sequence of SEQ ID NO: 41 and a VL region having at least 90% identity to the amino acid sequence of SEQ ID NO:46, with the proviso that the VH region comprises a variable heavy chain CDR1 of SEQ ID NO: 42, a variable heavy chain CDR2 of SEQ ID NO: 43, and a variable heavy chain CDR3 of SEQ ID NO: 44, and the VL region comprises a variable light chain CDR1 of SEQ ID NO: 47, a variable light chain CDR2 of SEQ ID NO: 48, and a variable light chain CDR3 of SEQ ID NO: 49; or
   a VH region of SEQ ID NO:51 and a VL region of SEQ ID NO:56, or
   a VH region having at least 90% identity to the amino acid sequence of SEQ ID NO: 51 and a VL region having at least 90% identity to the amino acid sequence of SEQ ID NO:56, with the proviso that the VH region comprises a variable heavy chain CDR1 of SEQ ID NO: 52, a variable heavy chain CDR2 of SEQ ID NO: 53, and a variable heavy chain CDR3 of SEQ ID NO: 54, and the VL region comprises a variable light chain CDR1 of SEQ ID NO: 57, a variable light chain CDR2 of SEQ ID NO: 58, and a variable light chain CDR3 of SEQ ID NO: 59; or
   a VH region of SEQ ID NO:61 and a VL region of SEQ ID NO:66, or a VH region having at least 95% identity to the amino acid sequence of SEQ ID NO: 61 and a VL region having at least 90% identity to the amino acid sequence of SEQ ID NO:66, with the proviso that the VH region comprises a variable heavy chain CDR1 of SEQ ID NO: 62, a variable heavy chain CDR2 of SEQ ID NO: 63, and a variable heavy chain CDR3 of SEQ ID NO: 64, and the VL region comprises a variable light chain CDR1 of SEQ ID NO: 67, a variable light chain CDR2 of SEQ ID NO: 68, and a variable light chain CDR3 of SEQ ID NO: 69; and wherein the VH and VL region is linked by at least one linker to at least one costimulatory domain, wherein the costimulatory domain is a CD28 costimulatory domain which comprises a sequence that differs at no more than 10, 9, 8, 7, 6, 5, 4, 3, 2, 1, or 0 amino acid residues from the sequence of SEQ ID NO: 2, SEQ ID NO: 4, or SEQ ID NO: 4 in combination with SEQ ID NO: 6 or SEQ ID NO: 8, or a 4-1BB costimulatory domain which comprises a sequence that differs at no more than 10, 9, 8, 7, 6, 5, 4, 3, 2, 1, or 0 amino acid residues from the sequence of SEQ ID NO: 16, or SEQ ID NO: 16 in combination with SEQ ID NO: 8.

2. The chimeric antigen receptor according to claim 1 wherein the CD28 costimulatory domain comprises the sequence of SEQ ID NO:2, SEQ ID NO:4, SEQ ID NO:6, or SEQ ID NO:8; or wherein the 4-1BB costimulatory domain comprises a sequence of SEQ ID NO: 16, or SEQ ID NO: 16 in combination with SEQ ID NO: 8.

3. The chimeric antigen receptor according to claim 1 wherein the CD3 zeta comprises a sequence that differs at no more than 10, 9, 8, 7, 6, 5, 4, 3, 2, 1, or 0 amino acid residues from the sequence of SEQ ID NO:10.

4. The chimeric antigen receptor according to claim 1 wherein the costimulatory domain comprises the sequence of SEQ ID NO:2, SEQ ID NO:4, SEQ ID NO:6, or SEQ ID NO:8, or SEQ ID NO: 16, or SEQ ID NO: 16 in combination with SEQ ID NO: 8 and the activating domain comprises the sequence of SEQ ID NO:10.

5. A polynucleotide encoding the chimeric antigen receptor of claim 1.

6. A vector comprising the polynucleotide of claim 5, wherein the vector is a retroviral vector, a DNA vector, a plasmid, a RNA vector, an adenoviral vector, an adenovirus associated vector, a lentiviral vector, or any combination thereof.

7. An immune cell comprising the vector of claim 6, wherein the immune cell is a T cell, tumor infiltrating lymphocyte (TIL), NK cell, TCR-expressing cell, dendritic cell, or NK-T cell.

8. A pharmaceutical composition comprising an immune cell of claim 7.

9. The chimeric antigen receptor according to claim 1, wherein the linker comprises the scFv G4S linker or the scFv Whitlow linker.

10. An isolated polypeptide comprising the amino acid sequence of SEQ ID NO: 18, 20, 22, 24, 26, or 28.

11. An isolated polynucleotide encoding the polypeptide of claim 10.

12. A method of treating cancer in a subject in need thereof comprising administering to the subject the immune cell according to claim 7.

13. The method according to claim 12 wherein the cancer is adrenal, liver, kidney, bladder, breast, gastric, ovarian, cervical, uterine, esophageal, colorectal, prostate, pancreatic, lung, thyroid, carcinomas, sarcomas, glioblastomas, head and neck tumors, large cell neuroendocrine carcinoma (LCNEC), medullary thyroid cancer, glioblastoma, neuroendocrine prostate cancer, (NEPC), high-grade gastroenteropancreatic cancer (GEP) and malignant melanoma.

14. The lentiviral vector according to claim 6, wherein the lentiviral vector is a pGAR vector having the sequence of SEQ ID NO:70.

* * * * *